United States Patent
Lombard

(10) Patent No.: US 8,706,526 B2
(45) Date of Patent: *Apr. 22, 2014

(54) NEUROPSYCHIATRIC TEST REPORTS

(71) Applicant: GenOmind, LLC, Chalfont, PA (US)

(72) Inventor: Jay L. Lombard, New City, NY (US)

(73) Assignee: GenOmind, LLC, Chalfont, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/739,970

(22) Filed: Jan. 11, 2013

(65) Prior Publication Data

US 2013/0132114 A1 May 23, 2013

Related U.S. Application Data

(63) Continuation of application No. 13/371,227, filed on Feb. 10, 2012, now Pat. No. 8,355,927, which is a continuation-in-part of application No. 13/290,603, filed on Nov. 7, 2011, now abandoned.

(60) Provisional application No. 61/410,523, filed on Nov. 5, 2010, provisional application No. 61/528,583, filed on Aug. 29, 2011.

(51) Int. Cl.
| | |
|---|---|
| *G06Q 10/00* | (2012.01) |
| *G06Q 50/00* | (2012.01) |
| *G06Q 50/22* | (2012.01) |
| *G06Q 50/24* | (2012.01) |

(52) U.S. Cl.
CPC ............... *G06Q 50/22* (2013.01); *G06Q 50/24* (2013.01)
USPC .................................................. 705/2; 705/3

(58) Field of Classification Search
CPC ........ G06Q 50/22; G06Q 50/24; G06F 19/10; G06F 19/3431; C12Q 1/6897
USPC ......................................................... 705/2, 3
See application file for complete search history.

(56) References Cited

U.S. PATENT DOCUMENTS

| | | |
|---|---|---|
| 4,169,157 A | 9/1979 | Kijima et al. |
| 4,728,605 A | 3/1988 | Fudenberg et al. |

(Continued)

FOREIGN PATENT DOCUMENTS

| | | |
|---|---|---|
| EP | 1844769 A2 | 10/2007 |
| EP | 1438063 B1 | 5/2010 |

(Continued)

OTHER PUBLICATIONS

Cheng et al.; Association study between BDNF gene polymorphisms and autism by three-dimensional gel-based microarray; Int. J. Mol. Sci.; vol. 10; pp. 2487-2500; Jun. 2009.

(Continued)

*Primary Examiner* — Neha Patel
(74) *Attorney, Agent, or Firm* — Shay Glenn LLP

(57) ABSTRACT

Methods and reports for presenting genetic information that is patient-specific and relevant to treatment of neuropsychiatric disorders, including treatment resistant psychiatric disorders, to aid in patient treatment in a phenotype, genotype or biomarker-specific manner. The methods and reports examine biomarkers for dysfunction of three axes relevant to treating neuropsychiatric disorders and provide interpretive comments to aid in treatment. Combining biomarker information from each of the three axes (the autonomic arousal axis, the emotional valence, attention, reward and executive brain function axis, and the long-term potentiation and long-term depression (LTP-LTD) function axis) provides an unexpectedly comprehensive and effective means for directing treatment of neuropsychiatric disorders, including particularly treatment resistant disorders (TRD).

18 Claims, 42 Drawing Sheets

(56) References Cited

U.S. PATENT DOCUMENTS

| | | | |
|---|---|---|---|
| 4,822,816 A | 4/1989 | Markham | |
| 5,210,015 A | 5/1993 | Gelfand et al. | |
| 5,487,972 A | 1/1996 | Gelfand et al. | |
| 5,763,183 A | 6/1998 | Pesonen et al. | |
| 5,874,312 A | 2/1999 | Sredni et al. | |
| 5,888,542 A | 3/1999 | Huet de Barochez et al. | |
| 6,027,896 A | 2/2000 | Roses et al. | |
| 6,114,133 A | 9/2000 | Seubert et al. | |
| 6,130,048 A | 10/2000 | Nixon | |
| 6,165,716 A | 12/2000 | Battersby et al. | |
| 6,210,895 B1 | 4/2001 | Schipper et al. | |
| 6,228,875 B1 | 5/2001 | Tsai et al. | |
| 6,358,681 B2 | 3/2002 | Ginsberg et al. | |
| 6,451,547 B1 | 9/2002 | Jackowski et al. | |
| 6,461,831 B1 | 10/2002 | Small et al. | |
| 6,465,195 B1 | 10/2002 | Holtzman et al. | |
| 6,475,161 B2 | 11/2002 | Teicher et al. | |
| 6,495,335 B2 | 12/2002 | Chojkier et al. | |
| 6,582,908 B2 | 6/2003 | Fodor et al. | |
| 6,727,063 B1 | 4/2004 | Lander et al. | |
| 7,049,429 B1 | 5/2006 | Albert et al. | |
| 7,072,501 B2 | 7/2006 | Wood et al. | |
| 7,371,522 B2 | 5/2008 | Williams, Jr. | |
| 8,355,927 B2 | 1/2013 | Lombard | |
| 2002/0037828 A1 | 3/2002 | Wilson et al. | |
| 2002/0142312 A1 | 10/2002 | Cigler et al. | |
| 2002/0161016 A1 | 10/2002 | Tam et al. | |
| 2003/0100476 A1 | 5/2003 | Weinberger et al. | |
| 2003/0198970 A1 | 10/2003 | Roberts | |
| 2003/0233250 A1 | 12/2003 | Joffe et al. | |
| 2004/0171083 A1 | 9/2004 | Albert et al. | |
| 2005/0075543 A1 | 4/2005 | Calabrese | |
| 2005/0165115 A1 | 7/2005 | Murphy et al. | |
| 2005/0208527 A1 | 9/2005 | Stefansson et al. | |
| 2006/0135422 A1 | 6/2006 | Moskowitz | |
| 2006/0160119 A1 | 7/2006 | Turner et al. | |
| 2006/0228728 A1 | 10/2006 | Cox et al. | |
| 2006/0264769 A1 | 11/2006 | Satin et al. | |
| 2007/0042969 A1 | 2/2007 | Rauschkolb-Loffler et al. | |
| 2007/0122395 A1 | 5/2007 | Blakely et al. | |
| 2007/0128597 A1 | 6/2007 | Schwers et al. | |
| 2007/0130287 A1* | 6/2007 | Kumar et al. | 709/217 |
| 2007/0134664 A1 | 6/2007 | Hager et al. | |
| 2007/0135504 A1 | 6/2007 | Marshall | |
| 2007/0232691 A1 | 10/2007 | Goren et al. | |
| 2008/0051371 A1 | 2/2008 | Zerangue et al. | |
| 2008/0058344 A1 | 3/2008 | Gerdes et al. | |
| 2008/0108076 A1 | 5/2008 | Chissoe | |
| 2008/0118918 A1 | 5/2008 | Licinio et al. | |
| 2008/0125831 A1 | 5/2008 | Morrell | |
| 2008/0167291 A1 | 7/2008 | Barlow et al. | |
| 2008/0199866 A1 | 8/2008 | Akil et al. | |
| 2008/0226759 A1 | 9/2008 | Marshak | |
| 2008/0248470 A1 | 10/2008 | Kim et al. | |
| 2008/0268436 A1 | 10/2008 | Duan et al. | |
| 2008/0299125 A1 | 12/2008 | Hinds et al. | |
| 2009/0088403 A1 | 4/2009 | Blakely et al. | |
| 2009/0176257 A1 | 7/2009 | Bahn et al. | |
| 2009/0176715 A1 | 7/2009 | Javitt | |
| 2009/0220971 A1 | 9/2009 | Stein et al. | |
| 2010/0003681 A1 | 1/2010 | Azuma et al. | |
| 2010/0098659 A1 | 4/2010 | Watson et al. | |
| 2010/0100333 A1* | 4/2010 | Pi et al. | 702/19 |
| 2010/0115421 A1* | 5/2010 | Bejjani et al. | 715/751 |
| 2010/0281401 A1* | 11/2010 | Tebbs et al. | 715/760 |
| 2010/0304391 A1 | 12/2010 | Lombard | |
| 2011/0237537 A1* | 9/2011 | Lombard | 514/46 |
| 2012/0009125 A1 | 1/2012 | Lombard | |
| 2012/0041066 A1 | 2/2012 | Lombard | |
| 2012/0115147 A1 | 5/2012 | Lombard | |
| 2012/0195984 A1 | 8/2012 | Lombard | |

FOREIGN PATENT DOCUMENTS

| | | |
|---|---|---|
| FR | 2104728 A1 | 4/1972 |
| FR | 2635461 A1 | 2/1990 |
| FR | 2716623 A1 | 9/1995 |
| KR | 20090104845 | 10/2009 |
| WO | WO95/13399 A1 | 5/1995 |
| WO | WO96/09386 A2 | 3/1996 |
| WO | WO96/17081 A1 | 6/1996 |
| WO | WO97/11175 A1 | 3/1997 |
| WO | WO01/09161 A1 | 2/2001 |
| WO | WO02/22887 A1 | 3/2002 |
| WO | WO2004/044244 A1 | 5/2004 |
| WO | WO2005/040427 A2 | 5/2005 |
| WO | WO2007/047978 A2 | 4/2007 |
| WO | WO2007/095580 A2 | 8/2007 |
| WO | WO2008/093057 | 8/2007 |
| WO | WO2007/120480 A2 | 10/2007 |
| WO | WO2007/134136 A2 | 11/2007 |
| WO | WO2007/147514 A1 | 12/2007 |
| WO | WO2008/017002 A2 | 2/2008 |
| WO | WO2008/036846 A2 | 3/2008 |
| WO | WO2008/047365 A1 | 4/2008 |
| WO | WO2008/113051 A2 | 9/2008 |
| WO | WO2009/077763 A1 | 6/2009 |
| WO | WO2009/108837 A2 | 9/2009 |
| WO | WO2009/114627 A2 | 9/2009 |
| WO | WO2009/128057 A2 | 10/2009 |

OTHER PUBLICATIONS

Margoob et al.; Serotonin transporter gene polymorphism and treatment response to serotonin reuptake inhibitor (escitalopram) in depression: an open pilot study; Indian J. Psychiatry; vol. 50; No. 1; pp. 47-50; Jan. 2008.

Lotrich et al.; Serotonin transporter genotype interacts with paroxetine plasma levels to influence depression treatment response in geriatric patients; J. Psychiatry Neurosci.; vol. 33; No. 2; pp. 123-130; Mar. 2008.

Ozaki et al.; A naturally occurring amino acid substitution of the human serotonin 5-HT2A receptor influences amplitude and timing of intracellular calcium mobilization; J Neurochem.; 68(5):2186-93; May 1997.

Smeraldi et al.; Polymorphism within the promoter of the serotonin transporter gene and antidepressant efficacy of fluvoxamine; Mol Psychiatry; 3(6):508-11; Nov. 1998.

Yamanouchi et al.; Effect of DRD2, 5-HT2A, and COMT genes on antipsychotic response to risperidone; The Pharmacogenomics J.; 3(6): 356R361; Dec. 11, 2003.

XVII World Congress of Psychiatric Genetics: Surfing the Wave of Discovery (CME); Nov. 4-8, 2009; San Diego, CA; retrieved from the internet: <http://cme.ucsd.edu/psychiatricgenetics/>, abstracts S14. 5, 9 and 43.

Lombard, J., U.S. Pat. Appl. No. 13/937,168 entitled "Methods and Compositions for the Treatment of Neuropsychiatric Disorders," filed Jul. 8, 2013.

Ahern; Biochemical, Reagent Kits Offer Scientists Good Return on Investment; The Scientist; 9(15); 5 pgs.; Jul. 24, 1995 (downloaded from http://www.the-scientist.library.upenn.edu/yr1995/july/tools_950724.html on Dec. 22, 1998).

New England Biolabs, Inc. 1998/1999 Catalog; Random Primers; Transcription Promoter Primers, Nucleic Acid Date, The Genetic Code and Isotope Data; pp. 121 & 284 (year of pub. sufficiently earlier than effective US filed and any foreign priority date).

* cited by examiner

Neurotransmitter Diagnostic Assay

| Patient ID # | 001-01234 | GenOmind Order # | 123456 |
|---|---|---|---|
| Collection Date | **** | Ordering Physician | Dr. Jay Lombard |
| Received Date | **** | Facility Name | Bronx Lebanon Hospital |
| Report Date | **** | Facility Phone # | 212-555-1212 |

INTRODUCTION

SEROTONIN NEUROTRANSMISSION

Genes Tested:

Serotonin Transporter and SNP functional variant of a single-nucleotide polymorphism (rs25531) in 5-HTTLPR.

Interpretive Comments:

- The gene SLC6A4 encodes the 5-HTT, a membrane protein that transports serotonin from synaptic spaces into presynaptic neurons.
- Pharmacodynamic studies of the Serotonin transporter gene suggest that patients with the S/S genotype do not respond as well to SSRI antidepressants and may experience more side effects. {Reference 1}
- In SSRI non responders who exhibit the S/S allele, consideration should be given to use of a non-SSRI.

Gene Test Results:
- TBD

DOPAMINE/NOREPINEPHRINE NEUROTRANSMISSIONS

Genes Tested:

MTHFr - Catechol Methyl Transferase (COMT),

FIG. 1A

Interpretive Comments:
- Polymorphisms in the MTHFr-COMT result in genetic variations within the frontal cortex dopamine system. Functional variants of COMT may either increase or decrease dopamine degrading enzyme activity and impacts the efficiency of prefrontal dopamine. Prefrontal dopamine plays a critical role in cognition, executive function, working memory and attention. Significant epistasis (gene-gene interactions) has been demonstrated in MTHFR/ COMT genotypes.
- The MTHFr 677T and COMT 158val/val exacerbate prefrontal dopamine deficiency.
- MTHFr/COMT genotypes should be obtained in patients with cognitive symptoms associated with a mood disorder and in patients who are being considered for methylfolate treatment.
- Patients with either or both MTHFR/COMT val/val have higher COMT mediated dopamine degradation and may require augmentation with a methylation agent such as methylfolate.

Gene Test Results:
- TBD

Genes Tested:
DRD2

Interpretive Comments:
- This gene encodes the D2 receptor. Insertion/deletions of the promoter strongly influence striatal dopamine binding and may influence anti psychotic drug response. {Reference 2}
- Individuals who demonstrate a deletion allele demonstrate poorer antipsychotic response compared to insertion genotype. {Reference 3}
- Individuals with the deletion allele are at higher risk of atypical neuroleptic-induced weight gain. {Reference 4}
- DRD2 gene variants should be obtained in patients who are prescribed atypical neuroleptics.

Gene Test Results:
- TBD

GLUTAMATE NEUROTRANSMISSION

Genes Tested
CACNA1C

FIG. 1B

Interpretive Comments:
- This gene encodes the L type voltage gated calcium channel which mediates intracellular calcium homeostasis and neuronal depolarization. CACNA1C polymorphisms have been associated as a risk factor gene for bipolar disease, schizophrenia and recurrent major depression. Risk allele carriers with polymorphisms in rs 1086737, rs 10848634 exhibit reduced activation of the anterior cingulate cortex, a region associated with mood regulation and stress related responses.
- CACNA1C gene polymorphisms should be obtained in patients with a family history of bipolar disorder, SSRI-induced mania or suicidal ideation, and in cases of depression associated with psychotic features.
- Patients with rs 10848634, etc. have increased risk of SSRI treatment emergent suicidality and a mood stabilizer may be considered in these patients {Reference 5}

Gene Test Results:
- TBD

PHARMACOKINETIC ANALYSIS

Genes Tested:
2D6 (and Alleles)

Interpretive Comments:
- Polymorphisms in p450 enzymes account for significant variations in drug metabolism and the majority of psychotropic agents are metabolized by these pathways. Variance in the activity of cytochrome p450 can lead to abnormal drug metabolism and are associated with potential drug-drug interactions and treatment emergent side effects.
- Abilify, Strattera, Remeron, Effexor, Paxil, Prozac and Cymbalta are examples of drugs primarily metabolized by the 2D6 enzyme.
- Poor metabolizers (2D6 PM) are at risk of Abilify-induced akathisia and dosage reductions of approximately 30-40% are recommended.
- Poor metabolizers taking Strattera are at risk of Atomoxetine-induced side effects and an alternate agent is recommended. {Reference}
- Poor metabolizers taking Cymbalta should be cautioned or avoid using with concurrent 2D6 metabolized drugs such as Metoprolol.
- Ultrametabolizers of 2D6 may have decreased drug concentrations and efficacy of Effexor, Morphine and Tramadol. Obtaining serum levels should be considered in incomplete or non responders using these agents.

Gene Test Results:
- TBD

FIG. 1C

Glossary/Key Terms

- Pharmacokinetics - the study of the action of drugs within the body, which can, in many respects, be envisioned more accurately as the actions of the body on an administered drug. It includes studies of the mechanisms of drug absorption, distribution, metabolism, and excretion; onset of action; duration of effect; biotransformation; and effects and routes of excretion of the metabolites of the drug.

- Pharmacodynamics - the study of how a drug acts on a living organism, including the pharmacologic response and the duration and magnitude of response observed relative to the concentration of the drug at an active site in the organism.

- Psychopharmacology – the study of the action of drugs on psychological functions and mental states.

Testing Limitations
Neurotransmitter based genotyping can provide useful information regarding the relationship of genetic factors to mood disturbances and specific reactions to psychotropic drugs. However, genotyping alone is not predictive or diagnostic of a specific psychiatric diagnosis and should not be used as a primary means of treatment decision making.

Physician Support & Customer Care
Physicians may contact us at (877) 555-1212 during the hours of 8am – 5pm EDT to speak directly with a Customer Care Representative or send an email to Support@***.com.

CLIA Lab Certification
Genotyping is provided in association with ***.

FIG. 1D

Neurotransmitter Diagnostic Report

| Patient ID # | 001-01234 | Order # | 123456 |
|---|---|---|---|
| Collection Date | ****** | Ordering Physician | Dr Jay Lombard |
| Received Date | ****** | Facility Name | Bronx Lebanon Hospital |
| Report Date | ****** | Facility Phone # | 212-555-1212 |

GENOTYPE TEST RESULTS

| NEUROTRANSMITTER GENE | TEST RESULTS |
|---|---|
| SEROTONIN | |
| SERT | There are no genomic polymorphisms noted in the serotonin transporter. |
| DOPAMINE | |
| COMT | There are no genomic polymorphisms noted in the COMT genes. |
| DrD2 | There are no genomic polymorphisms noted in the DrD2 genes. |
| MTHF | There are no genomic polymorphisms noted in the MTHF genes. |
| GLUTAMATE/IONIC | |
| CACNA1C | Genomic polymorphisms are noted in the CACNA1C gene with heterozygous expression of the A allele (indicating potentially excess neuronal excitability, calcium ion channel disturbances and excess glutamate). |
| TREK | There are no genomic polymorphisms noted in the TREK genes. |

REPORT GUIDE

This Neurotransmitter Diagnostic Report is designed as a tool for physicians to refine their clinical acumen in order to determine optimal treatment for patients with Treatment Resistant Depression (TRD).

STEP ONE: Pharmacokinetic
Obtain pharmacokinetic data for the patient types indicated.

STEP TWO: Pharmacodynamic
Review the Phenotype/Genotype and corresponding Treatment Recommendations.

STEP THREE: Treatment Recommendation
Determine the SCORE based on comparison of Phenotype/Genotype; this will yield the certitude of the Treatment Recommendation.

STEP FOUR: Genotype Analytical Information
Review additional genotype analysis.

Page 1

FIG. 2A

STEP ONE: Pharmacokinetic

Obtain pharmacokinetic data (2D6, 2C19) for the following patients:
- Patients on multiple medications
- Patients under 18 or over 65

NOTES:
- Patients taking Paroxetine, Fluoxetine, Duloxetine, Venlafaxine (additional criterion to assess 2D6)
- Patients taking Citalopram, Escitalopram (additional criterion to assess 2C19)

STEP TWO: Pharmacodynamic

SSRI NON-RESPONDER

Patients with incomplete or no remission, WITHOUT treatment emergent side effects.

| Phenotype | Genotype | Treatment Recommendation |
|---|---|---|
| | | *Consider dose adjustment with current agent* |
| • Cognitive symptoms associated with depression | MTHF | ✓ Continue SSRI treatment, AUGMENT with Methyfolate Acid (Deplin) |
| • History of bipolar disease<br>• Recurrent episodes of mood decompensation or agitation<br>• Consider bipolar diagnosis | CACNA1C polymorphism | ✓ Continue SSRI treatment, AUGMENT with Lamotrigine (Lamictal) |
| • Multiple prior anti depressant treatment failures<br>• SSRI- induced sexual dysfunction | TREK polymorphism | ✓ Continue SSRI treatment, AUGMENT with Buprorion (Wellbutrin) |
| • Depression associated with obsessionality or ruminations | DrD2 141 c/ins | ✓ Continue SSRI treatment, AUGMENT with Abilify |

SSRI NON-RESPONDER

Patients with incomplete or no remission, WITH treatment emergent side effects.

| Phenotype | Genotype | Treatment Recommendation |
|---|---|---|
| • Poor SSRI efficacy or SSRI-related side effects<br>• Insomnia, panic, anxiety symptoms | SERT ss | ✓ Switch SSRI treatment, CHANGE to Mirtazepine (Remeron) |
| • Depression associated with addictions, substance abuse<br>• Co morbid ADHD | COMT | ✓ Switch SSRI treatment, CHANGE to Buprorion (Wellbutrin), *except in individuals with a history of a seizure disorder.* |
| • Depression associated with physical or mental fatigue | DrD2 TT/del | ✓ Modafinil |

Page 2

FIG. 2B

STEP THREE: Treatment Recommendation

Determine SCORE based on patient Phenotype and Genotype, review corresponding Treatment Recommendation.

| SCORE | | Certitude of Treatment Recommendation |
|---|---|---|
| 0 | Patient exhibits NEITHER the Phenotype nor the Genotype | None |
| 1 | Patient exhibits EITHER the Phenotype or the Genotype | Reasonable |
| 2 | Patient exhibits BOTH the Phenotype AND the Genotype | Strong |

STEP FOUR: GENOTYPE ANALYTICAL INFORMATION

SEROTONIN NEUROTRANSMISSION

Genes Tested:
Serotonin Transporter and SNP functional variant of a single-nucleotide polymorphism (rs25531) in 5-HTTLPR.

Analytical Results:
- The short allele is associated with less efficient presynaptic reuptake resulting in higher tonic synaptic serotonin.

DOPAMINE NEUROTRANSMISSION

Genes Tested:
Catechol Methyl Transferase, DrD2

Analytical Results:
- Patients with the COMT val/val variant have higher levels of dopamine degradation in the prefrontal cortex
- Neuropsychiatric symptoms may include cognitive symptoms associated with depression

GLUTAMATE/IONIC CHANNELS

Genes Tested:
CACNA1C, KCNK2

Analytical Results:
- Alterations in voltage gated calcium ion channels may lead to abnormal depolarization of selective limbic regions associated with mood and perception.
- CACNA1 polymorphisms have been associated with bipolar disease, schizophrenia and treatment resistant depression.
- KCNK2 refers to a specific heat sensitive, brain potassium channel which determines cellular membrane excitability. TREK-1 regulates the endocrine stress response of the HPA axis via ACTH mediated cortisol secretion. Stress activates the hypothalamic-pituitary-adrenal (HPA) axis, releasing ACTH from the anterior pituitary gland and cortisol from the adrenal cortex.
- The importance of the KCNK2 gene in this activity is supported by research which demonstrates that TREK-1-deficient mice show a reduced elevation of cortisol level under stress and display a remarkable depression-resistant phenotype.
- Genomic polymorphisms of the KCNK2 potassium channel have been associated with increased vulnerability to depression.
- KCNK2 gene variants have been associated with resistance to multiple classes of antidepressants and may identify individuals at risk for treatment resistant depression.

Page 3

FIG. 2C

GLOSSARY OF KEY TERMS

- Genotype – refers to the genetic traits in an organism. Such coding is *inheritable*. The genotype is the genetic load that is copied every time a cell divides, and therefore is *inherited* down to the next generation.
- Phenotype - refers to observable, physical manifestations of an organism. The phenotype includes physical characteristics, behaviors corresponding to such species, structures, organs, behaviors, reflexes, etc.
- Pharmacokinetics - the study of the action of drugs within the body, which can, in many respects, be envisioned more accurately as the actions of the body on an administered drug. It includes studies of the mechanisms of drug absorption, distribution, metabolism, and excretion; onset of action; duration of effect; biotransformation; and effects and routes of excretion of the metabolites of the drug.
- Pharmacodynamics - the study of how a drug acts on a living organism, including the pharmacologic response and the duration and magnitude of response observed relative to the concentration of the drug at an active site in the organism.

TESTING LIMITATIONS

Neurotransmitter based genotyping can provide useful information regarding the relationship of genetic factors to mood disturbances. However, genotyping alone is not predictive or diagnostic of a specific psychiatric diagnosis and should not be used as a primary means of treatment decision making.

PHYSICIAN SUPPORT & CUSTOMER CARE

Physicians may CALL us at (877) 555-1212 during the hours of 8am – 5pm EDT to speak directly with a Customer Care Representative or EMAIL us at: Support@***.com.

CLIA Lab Certification

Genotyping is provided in association with ***

Page 4

FIG. 2D

Neuropsychiatric Assay Report

October 21, 2011

| | | | |
|---|---|---|---|
| Patient | Mary Smith | Patient ID | PG-xxxx GM xxx-xxx |
| Ordering Clinician | Samuel Faust, MD | Chief Complaint | Anxiety, Bipolar symptoms |
| Sample Type | Saliva | DSM IV | |
| Received Date | October 13, 2011 | Results Reviewed By | Kristen K. Reynolds, PhD |

*How to read this report: We indicate the appropriateness of Gene Response Association Studies to support the Physiological Significance of genetic results. We use this following key:*
- A = multiple studies reporting association at least one prospective study
- B = meta-analysis of GWAS results supports association
- C = multiple studies reporting association
- D = single study reporting association

Summary of Results

Gene and Result    SLC6A4    S/S
Serotonin Transporter

Physiological Significance    The short or S allele has been associated with decreased transcription of the serotonin transporter. This polymorphism has been associated with reduced stress resilience and higher rates of stress mediated psychological dysfunction as well as amygdala hyperactivity.

Gene Response Association Studies    Based upon existing published data, homozygote short allele variants are less likely to achieve remission of depression when treated with a SSRI(1) [D], and are more likely to have a higher number of anti depressant trials(2) [D], and in geriatric patients are more likely to discontinue treatment with a SSRI (but not mirtazapine) due to adverse effects(4) [D].

Gene and Result    CACNA1C    A/A
Calcium Channel

Physiological Significance    CACNA1C encodes the L type voltage gated calcium channel. Gene polymorphisms of the A allele has been associated with altered cerebral calcium gating and excessive neuronal depolarization in the hippocampus during emotional processing.

Gene Response Association Studies    In very large meta-analysis of GWAS studies, the CACNA1C variant has been associated with modest increase in liability for bipolar disease and schizophrenia(8,9) [B]. One study also suggested CACNA1C A allele variants are more likely to experience increased risk of citalopram emergent suicidality(7) [D].

Gene and Result    DRD2    Del/Del
Dopamine D2 Receptor

Physiological Significance    The D2 receptor plays a central role for neuroleptic receptor occupancy and anti-psychotic drug efficacy. Deletion allele variants have been associated with alterations of subcortical D2 receptor expression.

Gene Response Association Studies    Based upon existing published data, individuals with DRD2 deletion alleles are significantly less likely to respond to neuroleptic treatment(11) [C] and experience more adverse treatment effects compared to Insertion alleles(14) [C].

*Summary continued on page 2*

FIG. 3A

| | | |
|---|---|---|
| Gene and Result | COMT Val/Val<br>Catechol-O-Methyltransferase | |
| Physiological Significance | COMT is a methylation enzyme which converts dopamine and norepinephrine to inactive metabolites, primarily in the prefrontal cortex. The Val allele has approx 40% greater enzyme activity and higher dopamine degradation. Clinically, this may be associated with reduced prefrontal working memory. | |
| Gene Response Association Studies | Based upon existing published data, individuals who are COMT Val/Val homozygotes less likely to achieve remission of depression when treated with antidepressants(12) [D]. Conversely, individuals diagnosed with ADHD with COMT Val/Val are more likely to respond to psychostimulant treatment compared to COMT Met/Met(13) [D]. | |
| Gene and Result | MTHFR T/T<br>Methylenetetrahy-drofolate Reductase | |
| Physiological Significance | MTHFR is an important enzyme in the generation of methyl groups for DNA methylation. The common TT variant results in reduced enzyme activity and potential impairments in methyl dependent reactions involved in catecholamine synthesis and degradation. T allele carriers have been associated with reduced anterior cingulate activity on fMRI, a region of the brain critical in mood and memory. | |
| Gene Response Association Studies | Based upon multiple studies, individuals homozygous for the MTHF TT allele, have a greater odds ratio for the diagnosis of depression, bipolar disease and schizophrenia. (15) [C]. Preliminary data also suggests a more favorable trend of methylfolate treatment in individuals with TT variants [suggest we not include if not in press, unfortunately.] | |
| Gene and Result | CYP2D6 PM<br>Cytochrome P450 2D6 | |
| Physiological Significance | Cytochrome p450 enzymes, including 2D6, are involved in hepatic metabolism of drugs, including many psychotropic agents. Drug clearance is impacted by genetic variants in these enzymes. | |
| Gene Response Association Studies | Based upon existing published data, in individuals who are 2D6 poor metabolizers, metabolism of certain 2D6 drugs, including Risperdone, Venlafaxine, and Atomoxetine, may lead to significantly higher plasma levels(16) [B] and a trend toward a higher number of adverse drug effects when using these agents(15,16,17,18) [C]. | |
| Gene and Result | CYP2C19 PM<br>Cytochrome P450 2C19 | |
| Physiological Significance | Cytochrome p450 enzymes, including 2C19, are involved in hepatic metabolism of drugs, including many psychotropic agents. Drug clearance is impacted by genetic variants in these enzymes. | |
| Gene Response Association Studies | Based upon existing published data, in individuals who are 2C19 poor metabolizers, metabolism of certain 2C19 drugs, including Risperdone, Venlafaxine, and Atomoxetine, may lead to significantly higher plasma levels(16) [B] and a trend toward a higher number of adverse drug effects when using these agents(15,16,17,18) [C]. | |

FIG. 3B

SEROTONIN NEUROTRANSMISSION

Gene Tested:
Serotonin Transporter (SLC6A4), 5-HTTLPR Long(L)/Short(S) promoter insertion/deletion (rs63749047) and L(A)/L(G) (rs25531) polymorphism.

Indication for Genotyping:
Individuals who exhibited unsatisfactory or no response to previous SSRI treatment or who have developed treatment-emergent side effects.

Gene Test Results:
*This patient is homozygous for the Short promoter alleles, S/S.*

Regions Affected:

Coronal view                    Sagittal view

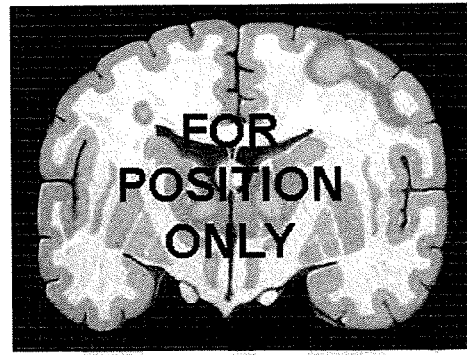 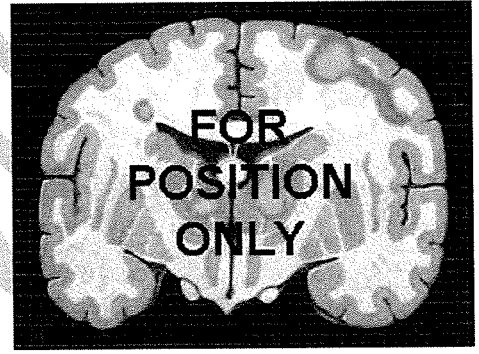

Interpretive Comments:
- Compared to patients with the Long (L) allele, the Short (S) allele results in decreased serotonin transporter expression, decreased presynaptic serotonin reuptake, and higher synaptic serotonin.
- Patients found to possess the Long (L) allele are also tested for the A>G polymorphism within the Long allele. Compared to the L(A) allele, the L(G) variant allele results in decreased expression of the serotonin transporter, and a phenotype similar to that of the Short(S) allele.
- Individuals with the Short (S) or L(G) alleles may be less likely to respond to SSRI-based antidepressant therapy, may be more likely to experience adverse effects from SSRIs, and may respond to SSRI therapy more slowly.
- In individuals with unsatisfactory response to SSRI therapy and who possess the Short (S) or L(G) alleles, treatment with an alternative antidepressant mechanism may be considered. Greater caution is recommended when initiating or discontinuing SSRIs in individuals with the Short (S) or L(G) alleles. Clinical correlation is suggested.

FIG. 3C

CALCIUM CHANNEL NEUROTRANSMISSION

Gene Tested:
Voltage-dependent calcium channel L-type, alpha 1c subunit (CACNA1C), G>A rs1006737

Indication for Genotyping:
Individuals with mood disorders who experience frequent relapses and recurrences.

Gene Test Results:
*This patient is homozygous for the CACNA1C rs1006737 G allele (A/A).*

Regions Affected:
Coronal view          Orbital view

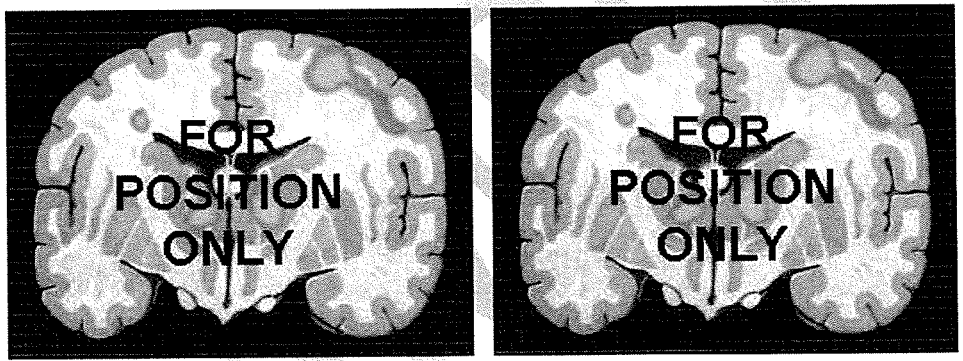

Interpretive Comments:
- CACNA1C gene alterations may lead to calcium channel disturbances, excess neuronal excitability, and excess glutamate. These alterations may lead to increased depolarization of selective limbic regions associated with mood and perception. Dysregulated calcium channels may lead to paroxysmal decompensations with increased risk of relapse in patients with mood disorders.
- The CACNA1C rs1006737 A allele has been associated with elevated rates of mood disorder recurrence.
- In individuals with the CACNA1C rs1006737 A allele and other clinical features such as family history which increase concern for bipolar disorder, particularly careful screening for other symptoms suggestive of bipolar disorder should be considered. After remission is achieved, close follow-up is warranted as recurrence risk may be elevated in these individuals.
- Membrane stabilizing agents such as mood stabilizers may be considered. Clinical correlation is suggested

FIG. 3D

DOPAMINE NEUROTRANSMISSION

Gene Tested:
Dopamine receptor D2 (DRD2), -141C insertion/deletion (rs1799732)

Indication for Genotyping:
Individuals with incomplete or no remission in symptoms of depression despite an adequate antidepressant trial who are being considered for augmentation with an atypical neuroleptic agent.

Gene Test Results:
*This patient is homozygous for the -141C Deletion allele (Del/Del).*

Regions Affected:
Orbital view                                      Sagittal view

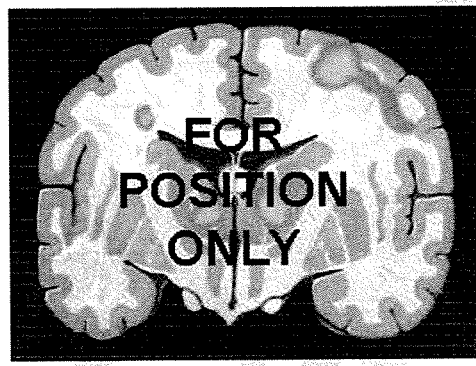 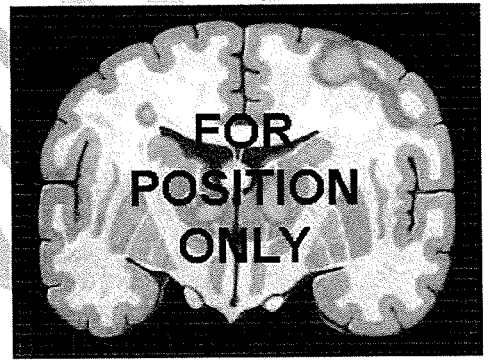

Interpretive Comments:
- Insertion/deletions of -141C in the DRD2 gene promoter may influence striatal dopamine binding and antipsychotic drug response.
- Individuals who carry the Del allele (Ins/Del or Del/Del) demonstrate less satisfactory antipsychotic drug response compared to patients with the homozygous Ins/Ins genotype. Del allele carriers also may be at higher risk of atypical neuroleptic-induced weight gain. Clinical correlation is suggested.

Gene Tested:
Catechol-O-Methyltransferase (COMT), 158 Val>Met (472 G>A, rs4680)

Indication for Genotyping:
Individuals with depression who also experience associated cognitive symptoms.

FIG. 3E

Gene Test Results:
*This patient is heterozygous for the 158 Valine and Methionine alleles (158 Val/Met, 472 G/A).*

Regions Affected:

Coronal view

Sagittal view

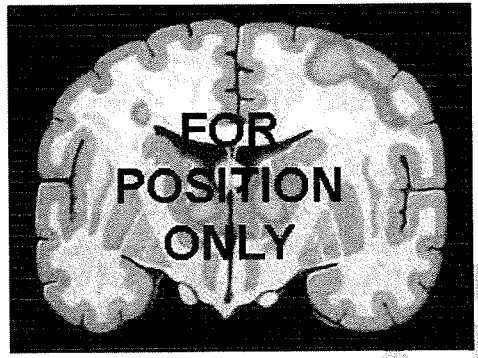 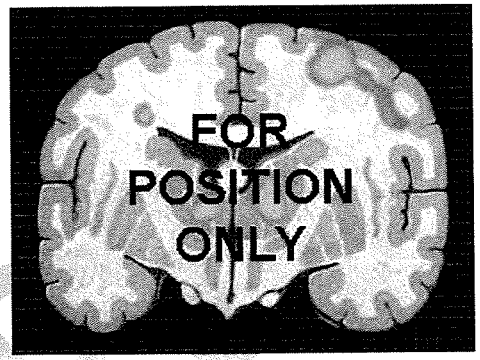

Interpretive Comments:
- COMT normally degrades dopamine and norepinephrine.
- The COMT 158 Val allele is a high-activity allele, leading to increased COMT activity and decreased dopamine in the prefrontal cortex. This effect may lead to reduced executive brain function, including cognitive and working memory deficits.
- Patients with the homozygous Val/Val genotype may be less likely respond to SSRI treatments. These differences may be related to reduced dopamine and/or norepinephrine availability in these individuals.
- Individuals with cognitive symptoms who possess the COMT Val allele may potentially benefit from agents which increase dopamine availability; however this has not been conclusively demonstrated in prospective studies. Clinical correlation is suggested.

METABOLISM ANALYSIS

Gene Tested:
Methylenetetrahydrafolate Reductase (MTHFR), 677 C>T

Indication for Genotyping:
Individuals with depression who also experience associated cognitive symptoms.

Gene Test Results:
*This patient is homozygous for the 677 T allele (677 T/T).*

FIG. 3F

Interpretive Comments:

- MTHFR is the predominant enzyme which converts inactive folic acid to an active form of folate. The 677 T allele is associated with decreased MTHFR activity, and may lead to increased homocysteine and decreased methylation capacity
- Elevated homocysteine and the MTHFR 677 TT genotype have been associated with increased risk of schizophrenia in men, as well as an increased risk of thrombosis.

NOTE: An epigenetic interaction between COMT and MTHFR alleles exists:

Epigenetic interactions refer to changes in gene expression as a result of non-genetic factors. DNA methylation processes account for one mechanism by which the expression of DNA is regulated by our environment. Impairments in methylation may result in an inability to suppress certain genes associated with cognitive and emotional states.

Decreased methylation of COMT, caused by the decreased function MTHFR 677T variant, results in decreased dopamine signaling and may ultimately lead to impairments in frontal lobe function. This effect may be exacerbated in patients who carry both the MTHFR 677T allele and the high-activity COMT 158 ValVal genotype. This effect has been demonstrated in schizophrenic patients but not healthy controls.

Conversely, the combination of the reduced activity COMT 158Met/Met and the MTHFR 677CC genotypes in schizophrenic patients results in decreased dopamine degradation and excessive dopamine signaling. This may also result in impaired prefrontal function, but with an increased risk of hyper-reactivity, although this effect has not been well-studied.

---

Gene Tested:

Cytochrome P450 2D6 (CYP2D6): Active alleles *1, *2; Partially active alleles *9, *10, *17, *41; Inactive alleles *3, *4, *5 (deletion), *6, *7, *8, *11, *12, *14, *15; Gene Duplication *1, *2, *4 (inactive), *10, or *41.

Indication for Genotyping:

- Patients on or being considered for medications metabolized by CYP2D6, or who have experienced significant side effects from previous medications metabolized by CYP2D6.

Gene Test Results:
*CYP2D6 genotype: *2/*4*
*CYP2D6 phenotype: Poor Metabolizer (PM)*

Interpretive Comments:

- Polymorphisms in cytochrome P450 enzymes account for significant variations in drug metabolism and the majority of psychotropic agents are metabolized by one or more of these pathways. Variable cytochrome P450 activity can result in

FIG. 3G abnormal drug metabolism leading to potential drug-drug interactions and treatment-emergent side effects.
- In addition to genetic variability, CYP2D6 may be affected by inhibitors such as fluoxetine, paroxetine, duloxetine, bupropion, and quinidine. Caution is advised when a medication metabolized by CYP2D6 is co-administered with a CYP2D6 inhibitor.
- CYP2D6 metabolizes nearly 25% of all medications including aripiprazole, atomoxetine, mirtazepine, risperidone, venlafaxine, paroxetine, fluoxetine, and duloxetine.
- General phenotype characteristics:
  - Extensive metabolizers (EM) represent the norm for metabolic capacity. Genotypes consistent with the EM phenotype include two active CYP2D6 alleles or one active and one partially active CYP2D6 allele. In general extensive metabolizers can be administered drugs which are substrates of CYP2D6 following standard dosing practices. Increased caution may be appropriate for individuals having one partially active allele.

Gene Tested:
Cytochrome P450 2C19 (CYP2C19): Active allele *1; Inactive alleles *2, *3, *4, *5, *6, *7, *8.

Indication for Genotyping:
- Patients on or being considered for medications metabolized by CYP2C19, or who have experienced significant side effects from previous medications metabolized by CYP2C19.

Gene Test Results:
*CYP2C19 genotype: *1/*2*
*CYP2C19 phenotype: Poor Metabolizer (PM)*

Interpretive Comments:
- Polymorphisms in cytochrome P450 enzymes account for significant variations in drug metabolism and the majority of psychotropic agents are metabolized by one or more of these pathways. Variable cytochrome P450 activity can result in abnormal drug metabolism leading to potential drug-drug interactions and treatment-emergent side effects.
- In addition to genetic variability, CYP2C19 may be affected by inhibitors such as fluconazole, ketoconazole, and proton pump inhibitors. Caution is advised when a medication metabolized by CYP2C19 is co-administered with a CYP2C19 inhibitor.
- CYP2C19 metabolizes many medications including diazepam, citalopram, and escitalopram.
- General phenotype characteristics:
  - Extensive metabolizers (EM) represent the norm for metabolic capacity. Genotypes consistent with the EM phenotype include two active CYP2C19

FIG. 3H alleles. In general extensive metabolizers can be administered drugs which are substrates of CYP2C19 following standard dosing practices.

Test Limitations
The Neuropsychiatric Assay alone is not predictive or diagnostic of a specific psychiatric diagnosis and should not be used as the primary or sole means of treatment decision making. These results should be regarded by the ordering physician as adjunctive to the overall patient management strategy.

Physician Support & Customer Care
Physicians may contact us at (877) 555-5555 during the hours of 8am – 5pm EDT to speak directly with a Customer Care Representative or email customerservice@***.com.

Methodology
Laboratory specimens were analyzed by a method developed by ****

References

1. Heils A, et al. Allelic variation of human serotonin transporter gene expression. J Neurochemistry 1996;66:2621-2624.
2. Popp J, Leucht S, Heres S and Steimer W. Serotonin transporter polymorphisms and side effects in antidepressant therapy – a pilot study. Pharmacogenetics 2006;7(2):159-166.
3. Gelernter J, Cubells JF, Kidd JR, Pakstis AJ, Kidd KK. Population studies of polymorphisms of the serotonin transporter protein gene. Am J Med Genet 1999;88(1):61-66.
4. Kato M and Serretti A. Review and meta-analysis of antidepressant pharmacogenetic findings in major depressive disorder. Molecular Psychiatry 2010;15, 473-500
5. Zhang J-P, Lencz T, and Malhotra AK. Dopamine D2 receptor genetic variation and clinical response to antipsychotic drug treatment: A meta-analysis. Am J Psychiatry 2010;167(7):763-772
6. Jönsson EG, et al. Polymorphisms in the dopamine D2 receptor gene and their relationships to striatal dopamine receptor density of healthy volunteers. Mol Psychiatry 1999;4(3):290-6.
7. Arinami T, Gao M, Hamaguchi H, Toru M. A functional polymorphism in the promoter region of the dopamine D2 receptor gene is associated with schizophrenia. Hum Mol Genet. 1997 Apr;6(4):577-82.
8. Baune B, et al. Association of the COMT val158met Variant with Antidepressant Treatment Response in Major Depression. Neuropsychopharmacology 2008;33:924–932.
9. Tsai SJ, et al. Sexually dimorphic effect of catechol-O-methyltransferase val158met polymorphism on clinical response to fluoxetine in major depressive patients. J Affect Disord. 2009;113(1-2):183-7.
10. Kocabas NA, et al. The impact of catechol-O-methyltransferase SNPs and haplotypes on treatment response phenotypes in major depressive disorder: a case-control association study. Int Clin Psychopharmacol. 2010;25(4):218-27.
11. Sazci A, et al. Association of the C677T and A1298C polymorphisms of methylenetetrahydrofolate reductase gene with schizophrenia: association is

FIG. 31 significant in men but not in women. Prog. Neuropsychopharmacol. Biol. Psychiatry 2005;29:1113-23.
12. Roffman JL, et al. MTHFR 677C>T genotype disrupts prefrontal function in schizophrenia through an interaction with COMT 158Val>Met. PNAS 2008;105(45):17573-8.
13. Ferreira MA, et al. Wellcome Trust Case Control Consortium. Collaborative genome-wide association analysis supports a role for ANK3 and CACNA1C in bipolar disorder. Nat Genet. 2008;40(9):1056-8.
14. Casamassima F, et al. Phenotypic effects of a bipolar liability gene among individuals with major depressive disorder. Am J Med Genet B Neuropsychiatr Genet. 2010;153B(1):303-9.
15. Kirchheiner J, et al. Pharmacogenetics of antidepressants and antipsychotics: the contribution of allelic variations to the phenotype of drug response. Mol Psychiatry. 2004;9:442-473.
16. http://www.cypalleles.ki.se/cyp2d6.htm

FIG. 3J

Catechol-O-Methyltransferase (COMT)

Return to top

Gene Tested     Catechol-O-Methyltransferase (COMT), 158 Val>Met (472 G>A, rs4680)

Gene Result     Val/Val

Physiological Significance     COMT is a methylation enzyme which converts dopamine and norepinephrine to inactive metabolites, primarily in the prefrontal cortex. The val allele has approx 40% greater enzyme activity and higher dopamine degradation. Clinically, this may be associated with reduced prefrontal working memory.

View     Coronal     Select Orbital

Gene Response Association Studies     Based upon existing published data, individuals who are COMT val/val homozygotes are less likely to achieve remission of depression when treated with antidepressants (12).* Conversely, individuals diagnosed with ADHD with comt val/val are more likely to respond to psychostimulant treatment compared to COMT met/met (13).*

Heils A, et al. Allelic variation of human serotonin transporter gene expression. J Neurochemistry 1996;66:2621-2624.

FIG. 4

Neuropsychiatric Assay Report          DATE

| Patient | M. Smith | Patient ID | PG-xxxx GM xxx-xxx |
|---|---|---|---|
| Ordering Clinician | Samuel Faust, MD | Received Date | November 17, 2011 |
| Sample Type | Saliva | Results Reviewed By | |

*How to read this report: Results for each genetic variation are provided and cover impacts, potential associations, and information regarding data and research results. Images are for illustrative purposes only.*

Summary of Results

SLC6A4
Serotonin Transporter

- The patient exhibits a variant of the serotonin transporter gene which results in reduced reuptake of serotonin and less satisfactory response to SSRI-based treatment compared to patients without this variant.

- The short variant has been associated with higher rates of PTSD and anxiety disorders. This increased vulnerability has been theorized to relate to excessive limbic amygdyla activation (see figure at right).

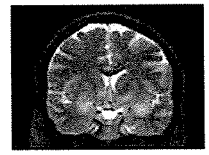

- There is limited pharmacogenomic data that supports non-SSRI-based interventions in individuals with this variant, including lithium and noradrenergic treatments; further prospective clinical trials, however, are indicated.

5HT2C
Serotonin Receptor

- This patient exhibits a polymorphism in the promoter of the 5HT2C gene, an important modulator of hypothalamic feeding behavior (see figure at right).

- Clinically, pharmacogenomic studies associated with this variant have been associated with antipsychotic-induced weight gain and metabolic syndrome.

- Greater pharmacovigilance related to weight gain and metabolic syndrome may be indicated for individuals with this variant.

CACNA1C
Calcium Channel

- The patient exhibits a calcium-channel variant that is associated with dysregulation of voltage-gated calcium ion channels. Dysregulation of this channel has been associated with excessive neuronal depolarization and potentially with glutamate-mediated imbalance (see figure at right).

- Clinically, higher rates of variations in this channel have been found in patients with TRD, autism, bipolar disease, and schizophrenia.

- Higher use of mood stabilizers have been reported in patients with this variant, however, limited prospective studies have been performed that demonstrate improved efficacy of these agents in patients with this variant.

FIG. 5A

ANK3
Sodium Channel
- This patient exhibits the a variant of the ankyrin 3 gene, which regulates voltage-gated sodium channels in axons and the nodes of ranvier of neurons. This variant may result in reduced white matter integrity in the anterior limb of the internal capsule (see figure at right).

- Clinically, higher rates of variation in this channel have been associated with schizophrenia and nonpsychotic bipolar disease. Reduced white-matter integrity has been associated with a cyclothymic subendophenotype.
- Currently, there are no prospective clinical trials or retrospective clinical data associated with sodium channel modulators associated with this variant.

DRD2
Dopamine D2 Receptor
- This patient exhibits a variant of the dopamine D2 receptor gene associated with reduced D2 receptor binding and inhibitory capacity (see figure at right).

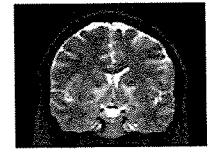

- Clinically, individuals with this variant have been associated with reduced anti-psychotic efficacy and higher rates of antipsychotic-induced metabolic syndrome.
- No prospective studies exist to date regarding alternative management in patients with this variant. Higher clinical vigilance should be considered in patients with this variant who have been prescribed antipsychotics.

DAT1
Dopamine Transporter
- This patient exhibits the a polymorphism in the DAT1 gene, the main regulator of dopamine signaling in the brain. This variant may interact with other dopamine genetic variants, including COMT and DRD2, to impact dopamine signaling in the reward-related ventral stritium area of the brain (see figure at right). This area related to motivational behavior, attention and addiction.

- Individuals with this variant of the DAT1 gene have been associated with Adult ADHD and bipolar disorder, however this data remains inconclusive.
- Individuals with the 9 repeat allele show higher striatal dopamine transport.
- Currently, there are no prospective studies and limited data associated with the use of dopamine agonists in individuals with this variant.

COMT
Catechol-O-Methyltransferase
- This patient exhibits the Val/Val variant of the Catechol-O-Methyltransferase gene. This variant results in higher dopamine degradation in frontal-cortical brain regions (see figure at right).

- Clinically, individuals with this variant have been associated with reduced working memory and other measures of executive brain function.
- There is limited data to support dopamine agonists in these individuals, but further prospective clinical studies are warranted.
- This patient exhibits the Met/Met variant of the Catechol-O-Methyltransferase gene. This variant results in reduced dopamine degradation in frontal-cortical brain regions (see figure at right).

- Clinically, individuals with this variant have been associated with higher risk of addictive disorders.
- Prospective studies which enhance COMT activity such as S-Adenosyl methionine are limited.

FIG. 5B

MTHFR
Methylenetetrahydrofolate Reductase
- This patient exhibits a variant of the Methylenetetrahy-drofolate Reductase gene, which may result in impaired folic acid metabolism (see figure at right). Folic acid and other B vitamins are required for normal neurotransmitter metabolism.

- Clinically, individuals with MTHFR variants have been associated with increased risk of depression, bipolar disorder, negative symptoms of schizophrenia, and autism.
- Limited, but preliminarily positive, prospective data exists regarding folic acid-based interventions in individuals with this variant.

CYP2D6
Cytochrome P450 2D6
- This patient exhibits the Poor Metabolizer variant of the CYP2D6 gene. This variant may result in reduced hepatic degradation of drugs that use this enzyme as a substrate, including but not limited to risperadone, olanzapine, venlafaxine and peroxeteine.
- Clinically, individuals with this variant may be more likely to experience dose-related adverse side-effects when prescribed these agents.
- There are limited prospective studies assessing the correlation of abnormal blood-levels of these drugs with this variant.
- This patient exhibits the Ultra Rapid Metabolizer variant of the CYP2D6 gene. This variant may result in heightened hepatic degradation of drugs that use this enzyme as a substrate, including but not limited to risperadone, olanzapine, and peroxeteine.
- Clinically, individuals with this variant may be more likely to experience dose-related reduced efficacy when prescribed these agents.
- There are limited prospective studies assessing the correlation of abnormal blood-levels of these drugs with this variant.

CYP2C19
Cytochrome P450 2C19
- This patient exhibits the Poor Metabolizer variant of the CYP2C19 gene. This variant results in reduced hepatic degradation of drugs that use this enzyme as a substrate, including but not limited to citalopram and s-citalopram.
- Clinically, individuals with this variant are more likely to experience dose-related adverse side-effects when prescribed these agents.
- There are limited prospective studies assessing the correlation of abnormal blood-levels of these drugs with this variant.
- This patient exhibits the Ultra Rapid Metabolizer variant of the CYP2C19 gene. This variant results in heightened hepatic degradation of drugs that use this enzyme as a substrate, including but not limited to risperadone, olanzapine, and peroxeteine.
- Clinically, individuals with this variant are more likely to experience dose-related reduced efficacy when prescribed these agents.
- There are limited prospective studies assessing the correlation of abnormal blood-levels of these drugs with this variant.

FIG. 5C

CYP3A5
Cytochrome P450 3A5
- This patient exhibits the Poor Metabolizer variant of the CYP3A5 gene. This variant results in reduced hepatic degradation of drugs that use this enzyme as a substrate, including but not limited to olazapine.
- Clinically, individuals with this variant are more likely to experience dose-related adverse side-effects when prescribed these agents.
- There are limited prospective studies assessing the correlation of abnormal blood-levels of these drugs with this variant.

FIG. 5D

SEROTONIN NEUROTRANSMISSION

Gene Tested:
Serotonin Transporter (SLC6A4), 5-HTTLPR Long(L)/Short(S) promoter insertion/deletion (rs63749047) and L(A)/L(G) (rs25531) polymorphism.

Indication for Genotyping:
Individuals who exhibited unsatisfactory or no response to previous SSRI treatment or who have developed treatment-emergent side effects.

Gene Test Results:
*This patient is homozygous for the Short promoter alleles, S/S.*

Regions Affected:

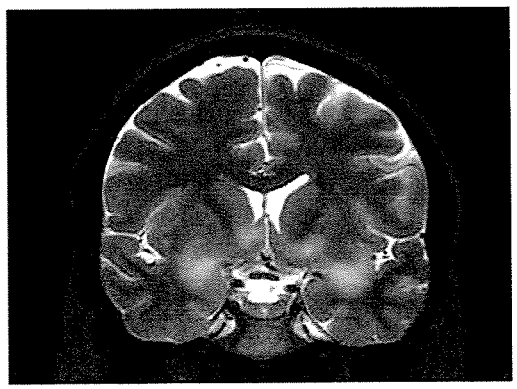

Interpretive Comments:
- Compared to patients with the Long (L) allele, the Short (S) allele results in decreased serotonin transporter expression, decreased presynaptic serotonin reuptake, and higher synaptic serotonin.
- Patients found to possess the Long (L) allele are also tested for the A>G polymorphism within the Long allele. Compared to the L(A) allele, the L(G) variant allele results in decreased expression of the serotonin transporter, and a phenotype similar to that of the Short(S) allele.
- Individuals with the Short (S) or L(G) alleles may be less likely to respond to SSRI-based antidepressant therapy, may be more likely to experience adverse effects from SSRIs, and may respond to SSRI therapy more slowly.
- In individuals with unsatisfactory response to SSRI therapy and who possess the Short (S) or L(G) alleles, treatment with an alternative antidepressant mechanism may be considered. Greater caution is recommended when initiating or discontinuing SSRIs in individuals with the Short (S) or L(G) alleles. Clinical correlation is suggested.

FIG. 5E

CALCIUM CHANNEL NEUROTRANSMISSION

Gene Tested:
Voltage-dependent calcium channel L-type, alpha 1c subunit (CACNA1C), G>A rs1006737

Indication for Genotyping:
Individuals with mood disorders who experience frequent relapses and recurrences.

Gene Test Results:
*This patient is homozygous for the CACNA1C rs1006737 G allele (A/A).*

Regions Affected:

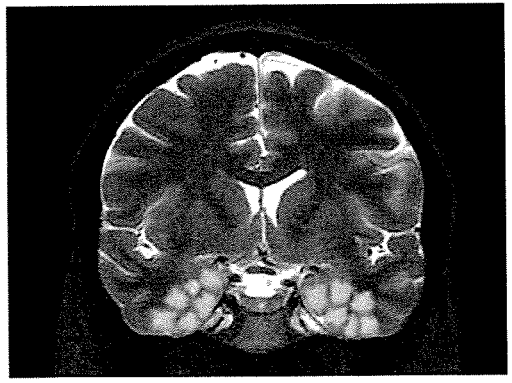

Interpretive Comments:
- CACNA1C gene alterations may lead to calcium channel disturbances, excess neuronal excitability, and excess glutamate. These alterations may lead to increased depolarization of selective limbic regions associated with mood and perception. Dysregulated calcium channels may lead to paroxysmal decompensations with increased risk of relapse in patients with mood disorders.
- The CACNA1C rs1006737 A allele has been associated with elevated rates of mood disorder recurrence.
- In individuals with the CACNA1C rs1006737 A allele and other clinical features such as family history which increase concern for bipolar disorder, particularly careful screening for other symptoms suggestive of bipolar disorder should be considered. After remission is achieved, close follow-up is warranted as recurrence risk may be elevated in these individuals.
- Membrane stabilizing agents such as mood stabilizers may be considered. Clinical correlation is suggested

FIG. 5F

DOPAMINE NEUROTRANSMISSION

Gene Tested:
Dopamine receptor D2 (DRD2), -141C insertion/deletion (rs1799732)

Indication for Genotyping:
Individuals with incomplete or no remission in symptoms of depression despite an adequate antidepressant trial who are being considered for augmentation with an atypical neuroleptic agent.

Gene Test Results:
*This patient is homozygous for the -141C Deletion allele (Del/Del).*

Regions Affected:

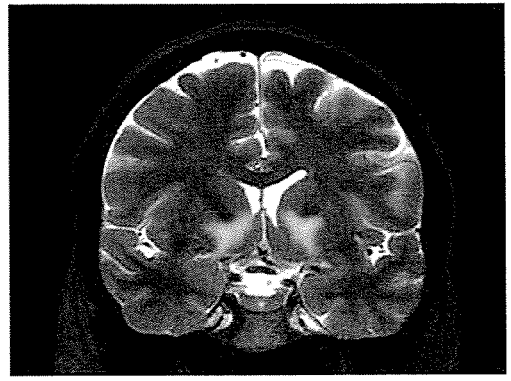

Interpretive Comments:
- Insertion/deletions of -141C in the DRD2 gene promoter may influence striatal dopamine binding and antipsychotic drug response.
- Individuals who carry the Del allele (Ins/Del or Del/Del) demonstrate less satisfactory antipsychotic drug response compared to patients with the homozygous Ins/Ins genotype. Del allele carriers also may be at higher risk of atypical neuroleptic-induced weight gain. Clinical correlation is suggested.

---

Gene Tested:
Catechol-O-Methyltransferase (COMT), 158 Val>Met (472 G>A, rs4680)

Indication for Genotyping:
Individuals with depression who also experience associated cognitive symptoms.

FIG. 5G

Gene Test Results:
*This patient is heterozygous for the 158 Valine and Methionine alleles (158 Val/Met, 472 G/A).*

Regions Affected:

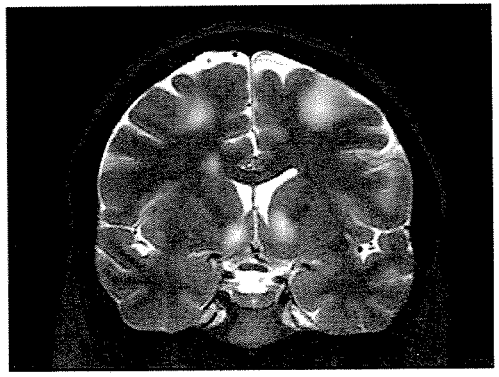

Interpretive Comments:
- COMT normally degrades dopamine and norepinephrine.
- The COMT 158 Val allele is a high-activity allele, leading to increased COMT activity and decreased dopamine in the prefrontal cortex. This effect may lead to reduced executive brain function, including cognitive and working memory deficits.
- Patients with the homozygous Val/Val genotype may be less likely respond to SSRI treatments. These differences may be related to reduced dopamine and/or norepinephrine availability in these individuals.
- Individuals with cognitive symptoms who possess the COMT Val allele may potentially benefit from agents which increase dopamine availability; however this has not been conclusively demonstrated in prospective studies. Clinical correlation is suggested.

FIG. 5H

METABOLISM ANALYSIS

Gene Tested:
Methylenetetrahydrafolate Reductase (MTHFR), 677 C>T

Indication for Genotyping:
Individuals with depression who also experience associated cognitive symptoms.

Gene Test Results:
This patient is homozygous for the 677 T allele (677 T/T).

Regions Affected:

Interpretive Comments:
- MTHFR is the predominant enzyme which converts inactive folic acid to an active form of folate. The 677 T allele is associated with decreased MTHFR activity, and may lead to increased homocysteine and decreased methylation capacity
- Elevated homocysteine and the MTHFR 677 TT genotype have been associated with increased risk of schizophrenia in men, as well as an increased risk of thrombosis.

NOTE: An epigenetic interaction between COMT and MTHFR alleles exists:
Epigenetic interactions refer to changes in gene expression as a result of non-genetic factors. DNA methylation processes account for one mechanism by which the expression of DNA is regulated by our environment. Impairments in methylation may result in an inability to suppress certain genes associated with cognitive and emotional states.

Decreased methylation of COMT, caused by the decreased function MTHFR 677T variant, results in decreased dopamine signaling and may ultimately lead to impairments in frontal lobe function. This effect may be exacerbated in patients who carry both the MTHFR 677T allele and the high-activity COMT 158 Val/Val genotype. This effect has been demonstrated in schizophrenic patients but not healthy controls.

FIG. 5I

Conversely, the combination of the reduced activity COMT 158Met/Met and the MTHFR 677CC genotypes in schizophrenic patients results in decreased dopamine degradation and excessive dopamine signaling. This may also result in impaired prefrontal function, but with an increased risk of hyper-reactivity, although this effect has not been well-studied.

Gene Tested:
Cytochrome P450 2D6 (CYP2D6): Active alleles *1, *2; Partially active alleles *9, *10, *17, *41; Inactive alleles *3, *4, *5 (deletion), *6, *7, *8, *11, *12, *14, *15; Gene Duplication *1, *2, *4 (inactive), *10, or *41.

Indication for Genotyping:
- Patients on or being considered for medications metabolized by CYP2D6, or who have experienced significant side effects from previous medications metabolized by CYP2D6.

Gene Test Results:
*CYP2D6 genotype: \*2/\*4*
*CYP2D6 phenotype: Poor Metabolizer (PM)*

Interpretive Comments:
- Polymorphisms in cytochrome P450 enzymes account for significant variations in drug metabolism and the majority of psychotropic agents are metabolized by one or more of these pathways. Variable cytochrome P450 activity can result in abnormal drug metabolism leading to potential drug-drug interactions and treatment-emergent side effects.
- In addition to genetic variability, CYP2D6 may be affected by inhibitors such as fluoxetine, paroxetine, duloxetine, bupropion, and quinidine. Caution is advised when a medication metabolized by CYP2D6 is co-administered with a CYP2D6 inhibitor.
- CYP2D6 metabolizes nearly 25% of all medications including aripiprazole, atomoxetine, mirtazepine, risperidone, venlafaxine, paroxetine, fluoxetine, and duloxetine.
- General phenotype characteristics:
  - Extensive metabolizers (EM) represent the norm for metabolic capacity. Genotypes consistent with the EM phenotype include two active CYP2D6 alleles or one active and one partially active CYP2D6 allele. In general extensive metabolizers can be administered drugs which are substrates of CYP2D6 following standard dosing practices. Increased caution may be appropriate for individuals having one partially active allele.

Gene Tested:
Cytochrome P450 2C19 (CYP2C19): Active allele *1; Inactive alleles *2, *3, *4, *5, *6, *7, *8.

FIG. 5J

Indication for Genotyping:
- Patients on or being considered for medications metabolized by CYP2C19, or who have experienced significant side effects from previous medications metabolized by CYP2C19.

Gene Test Results:
*CYP2C19 genotype: \*1/\*2*
*CYP2C19 phenotype: Poor Metabolizer (PM)*

Interpretive Comments:
- Polymorphisms in cytochrome P450 enzymes account for significant variations in drug metabolism and the majority of psychotropic agents are metabolized by one or more of these pathways. Variable cytochrome P450 activity can result in abnormal drug metabolism leading to potential drug-drug interactions and treatment-emergent side effects.
- In addition to genetic variability, CYP2C19 may be affected by inhibitors such as fluconazole, ketoconazole, and proton pump inhibitors. Caution is advised when a medication metabolized by CYP2C19 is co-administered with a CYP2C19 inhibitor.
- CYP2C19 metabolizes many medications including diazepam, citalopram, and escitalopram.
- General phenotype characteristics:
  - Extensive metabolizers (EM) represent the norm for metabolic capacity. Genotypes consistent with the EM phenotype include two active CYP2C19 alleles. In general extensive metabolizers can be administered drugs which are substrates of CYP2C19 following standard dosing practices.

FIG. 5K

Test Limitations
The Genecept™ Assay alone is not predictive or diagnostic of a specific psychiatric diagnosis and should not be used as the primary or sole means of treatment decision making. These results should be regarded by the ordering physician as adjunctive to the overall patient management strategy.

Physician Support & Customer Care
Physicians may contact Genomind at (877) 895-8658 during the hours of 8am – 5pm EDT to speak directly with a Customer Care Representative or email customerservice@genomind.com.

Methodology
Laboratory specimens were analyzed by a method developed by Pharmacogenetics Diagnostic Laboratories, LLC (PGXL Laboratories, CLIA No. 18D0983143, KY State License No. 200251) using the Luminex xMAP™ tag sorting system which detects 4 nucleotide variants in a multiplex PCR and allele-specific primer extension format. Testing for the serotonin transporter 5-HTTLPR and L(A>G) polymorphisms was performed by a method developed by PGXL Laboratories using PCR-RFLP and agarose gel analysis. Testing for CYP2D6 and CYP2C19 was performed using the xTAG™ Mutation Detection system for P450-2D6 and P450-2C19 (Luminex Molecular Diagnostics). The CYP2D6 assay detects 17 nucleotide variants plus two gene rearrangements and the CYP2C19 assay detects 7 nucleotide variants, both in a multiplex polymerase chain reaction and allele-specific primer extension format. Performance characteristics of all methods were validated by PGXL Laboratories. Analytical specificity and sensitivity for detection of all variants tested are >99%. Other known variants not listed are not detected. These methods have not been cleared or approved by the U.S. Food and Drug Administration, however, the FDA has determined that such clearance or approval is not necessary. This test is used for clinical purposes, and should not be regarded as investigational or for research. All testing was performed at PGXL Laboratories, 201 E. Jefferson Street, Suite 309, Louisville, KY 40202, (502)569-1584. Laboratory Directors: Mark W. Linder, PhD and Kristen K. Reynolds, PhD. This laboratory is certified under the Clinical Laboratory Improvement Amendment of 1988 (CLIA-88) as qualified to perform high complexity clinical laboratory testing.

References

1. Heils A, *et al*. Allelic variation of human serotonin transporter gene expression. J Neurochemistry 1996;66:2621-2624.
2. Popp J, Leucht S, Heres S and Steimer W. Serotonin transporter polymorphisms and side effects in antidepressant therapy – a pilot study. Pharmacogenetics 2006;7(2):159-166.
3. Gelernter J, Cubells JF, Kidd JR, Pakstis AJ, Kidd KK. Population studies of polymorphisms of the serotonin transporter protein gene. Am J Med Genet 1999;88(1):61-66.
4. Kato M and Serretti A. Review and meta-analysis of antidepressant pharmacogenetic findings in major depressive disorder. Molecular Psychiatry 2010;15, 473-500
5. Zhang J-P, Lencz T, and Malhotra AK. Dopamine D2 receptor genetic variation and clinical response to antipsychotic drug treatment: A meta-analysis. Am J Psychiatry 2010;167(7):763-772

FIG. 5L

6. Jönsson EG, et al. Polymorphisms in the dopamine D2 receptor gene and their relationships to striatal dopamine receptor density of healthy volunteers. Mol Psychiatry 1999;4(3):290-6.
7. Arinami T, Gao M, Hamaguchi H, Toru M. A functional polymorphism in the promoter region of the dopamine D2 receptor gene is associated with schizophrenia. Hum Mol Genet. 1997 Apr;6(4):577-82.
8. Baune B, et al. Association of the COMT val158met Variant with Antidepressant Treatment Response in Major Depression. Neuropsychopharmacology 2008;33:924–932.
9. Tsai SJ, et al. Sexually dimorphic effect of catechol-O-methyltransferase val158met polymorphism on clinical response to fluoxetine in major depressive patients. J Affect Disord. 2009;113(1-2):183-7.
10. Kocabas NA, et al. The impact of catechol-O-methyltransferase SNPs and haplotypes on treatment response phenotypes in major depressive disorder: a case-control association study. Int Clin Psychopharmacol. 2010;25(4):218-27.
11. Sazci A, et al. Association of the C677T and A1298C polymorphisms of methylenetetrahydrofolate reductase gene with schizophrenia: association is significant in men but not in women. Prog. Neuropsychopharmacol. Biol. Psychiatry 2005;29:1113-23.
12. Roffman JL, et al. MTHFR 677C>T genotype disrupts prefrontal function in schizophrenia through an interaction with COMT 158Val>Met. PNAS 2008;105(45):17573-8.
13. Ferreira MA, et al. Wellcome Trust Case Control Consortium. Collaborative genome-wide association analysis supports a role for ANK3 and CACNA1C in bipolar disorder. Nat Genet. 2008;40(9):1056-8.
14. Casamassima F, et al. Phenotypic effects of a bipolar liability gene among individuals with major depressive disorder. Am J Med Genet B Neuropsychiatr Genet. 2010;153B(1):303-9.
15. Kirchheiner J, et al. Pharmacogenetics of antidepressants and antipsychotics: the contribution of allelic variations to the phenotype of drug response. Mol Psychiatry. 2004;9:442-473.
16. http://www.cypalleles.ki.se/cyp2d6.htm

FIG. 5M

Neuropsychiatric Assay Report            DATE

Patient   A. Smith       Patient ID   PG-xxxx GM xxx-xxx

Ordering Clinician   John Smith, MD       Received Date
Sample Type          Saliva                Results Reviewed By

*How to read this report:*
*This information is based upon research data related to common genetic polymorphisms and their influence on behavior, psychiatric states and drug response. These results are not intended to diagnose or make specific treatment recommendations.* *All images are for illustrative purposes only and depict areas of the brain implicated in neuropsychiatric disturbances associated with a specific genetic variant. The medications and treatments within the report and are not intended to be comprehensive or prescriptive.*

Summary of Results

*Genes tested in the Assay include: SLC6A4, 5HT2C, CACNA1C, ANK3, DRD2, COMT, MTHFR and CYP 2D6, 2C19, 3A4/5.*

*Clinically significant variations were detected in the following: CYP 2D6, 2C19, 3A4/5, SLC6A4, 5HT2C, CACNA1C, ANK3, DRD2, COMT and MTHFR.*

SLC6A4

Serotonin Transporter

- The patient exhibits a variant of the serotonin transporter gene which may result in reduced reuptake of serotonin, less satisfactory response to SSRI-based treatments, and potentially a greater risk of adverse effects, compared to patients without this variant.

- This variant has been associated with lower rates of stress resilience and higher rates of PTSD. This increased vulnerability has been postulated to relate to excessive limbic amygdala reactivity (see figure at right)

- Alternative interventions that do not primarily target the serotonin transporter protein may be considered. Examples of alternative strategies include venlafaxine, duloxetine, , mirtazapine, lithium and cognitive behavioral therapy. The efficacy of these interventions has not been established in a genotype specific manner.

Serotonin Receptor

- This patient exhibits a variant of the 5HT2C receptor, which has been associated with satiety signaling in the hypothalamus (see figure at right).

- Pharmacogenomic studies have revealed reduced efficacy and increased incidence of atypical antipsychotic-induced side effects associated with this variant.

- Use caution with atypical antipsychotic medications such as:

| | |
|---|---|
| Aripiprazole | Paliperidone |
| Asenapine | Quetiapine |
| Clozapine | Risperidone |
| Iloperidone | Ziprasidone |
| Olanzapine | |

DRD2

Dopamine D2 Receptor

- This patient exhibits a variant of the dopamine D2 receptor gene, which has been associated with abnormal binding of dopamine and antipsychotics (see figure at right).

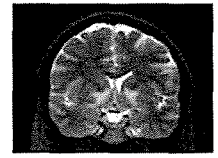

- Clinically, this variant has been associated with reduced efficacy of antipsychotic drugs and higher rates of antipsychotic-induced side effects.

- Use caution with atypical antipsychotic medications:

| | |
|---|---|
| Aripiprazole | Paliperidone |
| Asenapine | Quetiapine |
| Clozapine | Risperidone |
| Iloperidone | Ziprasidone |
| Olanzapine | |

CACNA1C

Calcium Channel

- The patient exhibits a calcium-channel variant that affects L-type voltage-gated calcium channels. Dysregulation of this channel has been associated with changes in neuronal depolarization and potentially with glutamate signaling (see figure at right).

- Clinically, higher rates of bipolar disorder and/or schizophrenia have been found in patients with variations in this gene. However, variations are not diagnostic of these disorders.

- Mood stabilizers approved for management of bipolar disorder, including lithium, valproic acid and lamotrigine, as well as atypical antipsychotic medications reduce neuronal excitability by moderating calcium mobilization. The efficacy of these agents has not been established in a genotype specific manner.

FIG. 7B

ANK3

- The patient exhibits a variant of the ANK3 gene, which may result in dysregulation of sodium channels, and reduced white matter axonal integrity (see figure at right).

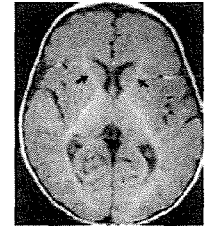

- Clinically, variants in this gene have been associated with schizophrenia, bipolar disorder and cyclothymic disorders. These variations indicate an increased relative risk, but are not diagnostic of these disorders.

- The mood stabilizer, lamotrigine, moderates ion channels and reduces neuronal excitability by modulating sodium channel activity. While this agent is approved for management of certain forms of epilepsy and bipolar disorders, efficacy has not been established in a genotype specific manner.

COMT

Catechol-O-Methyltransferase

- This patient exhibits the Val/Val variant of the Catechol-O-Methyltransferase gene. This variant may result in higher dopamine degradation and lower activation in the prefrontal cortex (see figure at right).

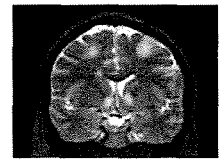

- Clinically, this variant has been associated with reduced working memory and other measures of executive function associated with psychiatric disorders.

- fMRI results indicate that antidepressants with different mechanisms of action have different effects on brain function. Repetitive transcranial magnetic stimulation (rTMS) of the dorsolateral prefrontal cortex (DLPFC) likely contributes to its therapeutic effects via activation of the dorsolateral prefrontal cortex. However, the efficacy of this intervention has not been established in a genotype specific manner.

MTHFR

Methylenetetrahydrofolate Reductase

- This patient exhibits a variant of the Methylenetetrahydrofolate Reductase (MTHFR) gene, which may result in impaired folic acid metabolism and blunted activation in the anterior cingulate (see figure at right). Metabolism of folic acid and other B vitamins are required for normal neurotransmitter synthesis.

- Clinically, individuals with MTHFR variants have been associated with increased risk of depression, bipolar disorder, schizophrenia, and autism. Variations indicate an increased relative risk, but are not diagnostic of these disorders.

- Limited, but preliminarily positive, prospective data exists regarding methylfolic acid-based interventions in individuals with depression.

FIG. 7C

CYP2D6

Cytochrome P450 2D6

- This patient exhibits the Poor Metabolizer or Intermediate Metabolizer variant of the CYP2D6 gene. This variant may result in reduced hepatic degradation and higher plasma levels of drugs metabolized through this pathway, potential increased adverse drug effects, or interference with production of active moieties.

- Clinically, drug-drug interactions are more likely to occur with concomitant administration of drugs that are 2D6 substrates (see list below)

- Clinicians should use increased caution when prescribing these drugs in patients who are poor metabolizers and if clinical response and/or blood-levels warrant, a dose adjustment may be considered.

- Common psychotropic substrates of CYP2D6 include:

Fluoxetine          Paroxetine
Duloxetine          Risperidone
Codeine             Tramadol
Fluvoxamine         Venlafaxine
Aripiprazole        Atomoxetine
Methadone TCAs (amitriptyline, clomipramine, desipramine, doxepin, nortriptyline)
Phenothiazines (chlorpromazine, fluphenazine, perphenazine, thioridazine)

CYP2C19

Cytochrome P450 2C19

- This patient exhibits the Poor Metabolizer or Intermediate Metabolizer variant of the CYP2C19 gene. This variant may result in reduced hepatic degradation and higher plasma levels of drugs metabolized through this pathway, potential increased adverse drug effects, or interference with production of active moieties.

- Clinically, drug-drug interactions are more likley to occur with concomitent administration of drugs that are 2C19 substrates (see list below).

- Clinicians should use increased caution when prescribing these drugs in patients who are poor metabolizers and if clinical response and/or blood-levels warrant, a dose adjustment may be considered.

- Common psychotropic substrates of CYP2C19 include:

Citalopram
Escitalopram
Diazepam
TCAs (amitriptyline, clomipramine, desipramine, doxepin, nortriptyline)

FIG. 7D

CYP3A4/5

Cytochrome P450 3A4/5

- This patient exhibits the Poor Metabolizer variant of the CYP3A4/5 gene. This variant may result in reduced hepatic degradation and higher plasma levels of drugs metabolized through this pathway, and potential increased adverse drug effects.
- Clinically, drug-drug interactions are more likley to occur with concomitant administration of drugs that are 3A4/5 substrates (see list below).
- Clinicians should use increased caution when prescribing these drugs in patients who are poor metabolizers and if clinical response and/or blood-levels warrant, a dose adjustment may be considered..
- Common psychotropic substrates of CYP3A4 include:

| | |
|---|---|
| Alrazolam | Desvenlafaxine |
| Clonazepam | Ziprasidone |
| Modafinil | Carbamazepine |
| Aripiprazole | Haloperidol |
| Clozapine | Oxycodone |
| Quetiapine | Eszopiclone |
| Buspirone | Zolpidem |

TCAs (amitriptyline, clomipramine, desipramine, doxepin, nortriptyline)

Cytochrome P450 Inhibition and Induction

- Certain medications can alter the metabolic activity of these enzymes independent of a patient's genotype.
  - Inhibitors reduce metabolic activity of enzymes and may result in increased toxicity due to reduced metabolism of the substrate, decreased efficacy due to reduced production of active moieties and increased drug-drug interactions.
  - Inducers increase metabolic activity of enzymes and may result in decreased efficacy due to increased metabolism of the substrate and adverse events due to increased production of toxic metabolites.

(For a full list of cytochrome P450 inducers and inhibitors, see Appendix X)

FIG. 7E

Appendix X

(*) metabolized to an active moiety (bold) strong inhibitor/inducer

This table contains substrates, inhibitors, and inducers that have been involved in a drug interaction of clinical relevance based on published literature. This table is not comprehensive as new information is constantly being identified.

Aripiprazole
Atomoxetine
Codeine*
Duloxentine
Fluoxetine
Fluvoxamine
Methadone
Paroxetine
Phenothiazines (chlorpromazine, fluphenazine,
 perphenazine, thioridazine)
Risperidone *
TCAs (amitriptyline, clomipramine, desipramine,
 doxepin, nortriptyline)
Tramadol
Venlafaxine
Amiodarone
Bupropion
Celecoxib
Chlorpheniramine
Chlorpromazine
Cimetidine
Citalopram
Clomipramine
Cocaine
Desipramine
Diphenhydramine
Doxorubicin
Fluoxetine
Fluphenazine
Fluvoxamine
Halofantrine
Haloperidol
Hydroxychloroquine
Imatinib
Imipramine
Levomepromazine
Methadone
Metoclopramide
Mibefradil
Moclobemide
Nefazodone
Nelfinavir
Norfluoxetine
Paroxetine
Perphenazine
Pimozide
Quinidine
Ranitidine

Ritonavir
Sertraline
Terbinafine
Venlafaxine

Dexamethasone
Rifampin

Alprazolam
Aripiprazole
Buspirone
Carbamazepine
Desvenlafaxine
Eszopiclone
Clonazepam
Clozapine
Haloperidol
Modafinil
Oxycodone
Quetiapine
TCAs (amitriptyline, clomipramine, desipramine,
 doxepin, nortriptyline)
Ziprasidone
Zolpidem Acitretin
Amiodarone
Amprenavir
Aprepitant
Cimetidine
Cinacalcet
Ciprofloxacin
Clarithromycin
Cyclosporine
Danazol
Delavirdine
Diltiazem
Efavirenz
Erythromycin
Fluconazole
Fluoxetine
Fluvoxamine
Grapefruit
Imatinib
Indinavir
Isoniazid
Itraconazole

FIG. 7F

Ketoconazole
Metronidazole
Methylprednisolone
Miconazole
Mifepristone
Nefazodone
Nelfinavir
Norfloxacin
Norfluoxetine
Quinine
Ritonavir
Saquinavir
Sertraline
Synercid
Telithromycin
Verapamil
Voriconazole
Zafirlukast Aminoglutethimide
Aprepitant
Carbamazepine
Efavirenz
Garlic Supplements
Glucocorticoids
Griseofulvin
Modafinil
Nafcillin
Nevirapine
Oxcarbazepine
Phenobarbital
Phenytoin
Primidone
Rifabutin
Rifampin
Rifapentine
St John's Wort

Citalopram
Diazepam
Escitalopram
TCAs (amitriptyline, clomipramine, desipramine, doxepin, nortriptyline)

Armodafinil
Chloramphenicol
Delavirdine
Esomeprazole
Felbamate
Fluconazole
Fluoxetine
Fluvoxamine
Indomethacin
Isoniazid
Ketoconazole
Lansoprazole
Letrozole
Modafinil
Omeprazole
Oxcarbazepine
Paroxetine
Ticlopidine
Topiramate
tranylcypromine
Voriconazole
Carbamazepine
Norethindrone
Phenobarbital
Phenytoin
Prednisone
Rifampin
St John's Wort

FIG. 7G

Neuropsychiatric Assay Report                    DATE

Patient         C. Smith            Patient ID         PG-xxxx GM xxx-xxx

Ordering Clinician  John Smith, MD   Received Date
Sample Type         Saliva           Results Reviewed By

*How to read this report:*
*This information is based upon research data related to common genetic polymorphisms and their influence on behavior, psychiatric states and drug response. These results are not intended to diagnose or make specific treatment recommendations. All images are for illustrative purposes only and depict areas of the brain implicated in neuropsychiatric disturbances associated with a specific genetic variant. The medications and treatments within the report and are not intended to be comprehensive or prescriptive.*

Summary of Results

*Genes tested in the Assay include: SLC6A4, 5HT2C, CACNA1C, ANK3, DRD2, COMT, MTHFR and CYP 2D6, 2C19, 3A4/5.*

No Reportable Variation

- This patient does not exhibit any variants for the genes tested in this assay. However, this result does not exclude other variations in the genes tested, the adverse influence of other genes not tested, or other metabolic factors associated with psychiatric disorders.

SLC6A4
Serotonin Transporter
- No variant identified.

5HT2C
Serotonin Receptor
- No variant identified.

DRD2
Dopamine D2 Receptor
- No variant identified.

CACNA1C
Calcium Channel
- No variant identified.

ANK3
- No variant identified.

COMT
Catechol-O-Methyltransferase
- No variant identified.

MTHFR
Methylenetetrahydrofolate Reductase
- No variant identified.

CYP2D6
Cytochrome P450 2D6
- No variant identified.

CYP2C19
Cytochrome P450 2C19
- No variant identified.

CYP3A4/5
Cytochrome P450 3A4/5
- No variant identified.

Cytochrome P450 Inhibition and Induction
- No variant identified.

FIG. 8

Neuropsychiatric Assay Report

DATE

| | | | |
|---|---|---|---|
| Patient | B. Smith | Patient ID | PG-xxxx GM xxx-xxx |
| Ordering Clinician | John Smith, MD | Received Date | |
| Sample Type | Saliva | Results Reviewed By | |

*How to read this report:*

This information is based upon research data related to common genetic polymorphisms and their influence on behavior, psychiatric states and drug response. These results are not intended to diagnose or make specific treatment recommendations. All images are for illustrative purposes only and depict areas of the brain implicated in neuropsychiatric disturbances associated with a specific genetic variant. The medications and treatments within the report and are not intended to be comprehensive or prescriptive.

Summary of Results

*Genes tested in the Assay include: SLC6A4, 5HT2C, CACNA1C, ANK3, DRD2, COMT, MTHFR and CYP 2D6, 2C19, 3A4/5.*

*Clinically significant variations were detected in the following: COMT*

COMT

Catechol-O-Methyltransferase

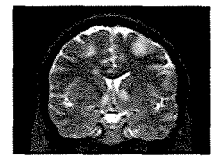

- This patient exhibits the Val/Val variant of the Catechol-O-Methyltransferase gene. This variant may result in higher dopamine degradation and lower activation in the prefrontal cortex (see figure at right).

- Clinically, this variant has been associated with reduced working memory and other measures of executive function associated with psychiatric disorders.

- fMRI results indicate that antidepressants with different mechanisms of action have different effects on brain function. Repetitive transcranial magnetic stimulation (rTMS) of the dorsolateral prefrontal cortex (DLPFC) likely contributes to its therapeutic effects via activation of the dorsolateral prefrontal cortex. However, the efficacy of this intervention has not been established in a genotype specific manner.

FIG. 9

NEUROPSYCHIATRIC TEST REPORTS

CROSS REFERENCE TO RELATED APPLICATIONS

This patent application is a continuation of U.S. patent application Ser. No. 13/371,227, filed Feb. 10, 2012 and titled NEUROPSYCHIATRIC TEST REPORTS," now Publication No. US-2012-0136680-A1 which claims priority as a continuation-in-part to U.S. patent application Ser. No. 13/290,603, filed Nov. 7, 2011 and titled "NEUROPSYCHIATRIC TEST REPORTS," now Publication No. US-2012-0115147-A1, which claims priority to U.S. Provisional Patent Application No. 61/410,523, filed Nov. 5, 2010, titled "TREATMENT RESISTANT DEPRESSION DIAGNOSTIC TEST REPORT." Each of these patent applications is herein incorporated by reference in their entirety.

U.S. patent application Ser. No. 13/371,227 also claims priority to U.S. Provisional Patent Application No. 61/528,583, filed Aug. 29, 2011 and titled "INTERPRETIVE BIOMARKER SCREENING REPORTS FOR DIAGNOSIS AND TREATMENT OF PSYCHIATRIC DISORDERS" which is herein incorporated by reference in its entirety.

This patent application may be related to any of the following: U.S. patent application Ser. No. 12/790,262, filed May 28, 2010 and titled "METHOD FOR ASSESSMENT AND TREATMENT OF DEPRESSION VIA UTILIZATION OF SINGLE NUCLEOTIDE POLYMORPHISMS ANALYSIS," now Publication No. US-2010-0304391-A1;

U.S. patent application Ser. No. 13/074,967, filed Mar. 29, 2011, titled "METHODS FOR ASSESSMENT AND TREATMENT OF MOOD DISORDERS VIA SINGLE NUCLEOTIDE POLYMORPHISMS ANALYSIS," now Publication No. US-2011-0237537-A1;

U.S. patent application Ser. No. 13/177,032, filed Jul. 6, 2011, titled "APOE4 AND APOJ BIOMARKER-BASED PREVENTION AND TREATMENT OF DEMENTIA," now Publication No. US-2012-0009125-A1; and U.S. patent application Ser. No. 13/210,808, filed Aug. 16, 2011, titled "MEDICAL FOODS FOR THE TREATMENT OF DEVELOPMENTALLY-BASED NEUROPSYCHIATRIC DISORDERS VIA MODULATION OF BRAIN GLYCINE AND GLUTATHIONE PATHWAYS," now Publication No. US-2012-0041066-A1. Each of these patent applications is herein incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

This patent application relates to personalized neuropsychiatric diagnostic reports and methods of generating such reports. In particular, this application describes integrated personalized diagnostic reports configured to provide streamlined, qualitative and quantitative information to guide a physician treating a psychiatric patient wherein the information presented is specific to the particular patient. These reports include biomarkers from each of three neurologically relevant axes. By examining at least one biomarker for each of these axes, the report may provide patient-specific information relevant to the use of one or more neurotherapeutic agents (e.g., drugs, medical foods, or the like that may be used to treat a neuropsychiatric disorder) in a biomarker based fashion to improve therapeutic outcomes.

BACKGROUND

In the last fifty years, a tremendous amount of research has begun to elucidate the causes, characteristics and treatments of many neuropsychiatric disorders. Unfortunately, this process has not efficiently translated into effective patient treatments. The term "treatment resistance" is more the norm than the exception in psychiatry. For instance, in the Catie trials, which looked at the effectiveness of medications in schizophrenia, more than 75% of patients discontinued medication within 18 months, and in the Star-D trials more than 50% of patients with depression did not achieve remission despite the use of two or more antidepressants or use of an augmenting agent. This "treatment resistance" may be due in part to the fact that neuropsychiatric disorders are notoriously difficult to diagnose because existing categories of disorders are imprecise; there is a great deal of overlap and comorbidity in these conditions. It is also relevant to note that in randomized clinical trials, a significant majority of patients (85%) would need to be excluded because of a comorbid psychiatric or medical condition. Thus, it is difficult to accurately categorize patients. In general, categorical tests for neuropsychiatric disorders have not proven effective in accurately diagnosing and treating patients, as there is a great deal of variation in patient outcomes between patients categorized with the same diagnosis. Most psychiatric classification systems, which are based upon categorical assessments, do not take into account that most mental disorders are dimensional with similar and overlapping symptoms in patients with discrete diagnostic categories. Even in research settings, the limitations of current categorical nosology of psychiatric disorders results in a disconnect between trial findings and application to real world settings. The problem of treatment resistance in psychiatry, the lack of biomarkers for diagnosis, the fact of similar symptoms in different categorical diagnoses, and the difficulty in drawing boundaries between disorders, all necessitates a paradigm shift from categorical to dimensional diagnostics. This dimensional approach, which is herein described, focuses on dimensional symptoms which are correlated with their biological underpinnings. This model incorporates subsets of psychiatric symptoms across cognitive, affective and subcortical regional locations, and which can thus be identified by objective biomarkers. These biomarkers, designed and described to identify neurobiological alterations in the domains of brain structure, physiology and neurochemistry, reflect diverse pathophysiological pathways from genome to phenome.

Virtually all brain disorders may cause psychiatric symptoms. The term "neuropsychiatric disorders" may refer to brain disease or dysfunction that causes psychiatric symptoms. Examples of neuropsychiatric disorders include depression (including treatment resistant depression, bipolar depression, etc. . . . ), schizophrenia, PTSD and other anxiety disorders, autism, ADHD, and the like.

Although various research and clinical studies have looked for diagnostic and therapeutic indicators in an almost overwhelming variety of genomic markers, gene expression markers and protein markers, this vast and growing body of data has proven difficult to interpret. Most physicians are unable to synthesize the tremendous amount of information on possible risk factors and indicators in order to apply this information clinically to diagnose and/or treat patients. Thus, there is an as yet unmet need for reports, panels and/or kits that would allow a medical professional to apply the most relevant genetic, epigenetic, transcriptomic, proteomic and functional imaging tests in a meaningful manner to their patients. It is also critical to provide tests that allow the medical profession to understand and interpret the results of such tests, as well as have a resource to call upon for clarification of their interpretations.

Described herein are systems and kits, including panels, assays and articles of manufacture, including reports and the use of expert-driven information help centers, which meet this need by providing interpretive and directed reports, particularly for the treatment of neuropsychiatric disorders such as depression. Because of the confusing and contradictory information available for even those genes established as implicated for treatment of depression and dementia, it would be beneficial to provide systems that (1) select the relevant genes, gene families, and/or pathways, epigenetic markers, and/or protein/expression markers; (2) provides information or links to the key information such as the relevance and meaning of each indicator or screen member; (3) suggests or provide relevant therapies based on the results of these tests; (4) provide an indication of the confidence/reliability of the interpretive information provided; (5) provide additional interactive information (e.g., a help center) that can answer questions as they relate specific test results to accurately apply the information to their patients. In particular, described herein are methods and articles of manufacture that may provide a concise reporting to a medical professional to help make diagnostic and/or therapeutic decisions.

The interpretive reports described herein may also be useful in developing and understanding new sites of action, association, and/or patient response to psychotropic drugs, as well as a previously undisclosed explanations on how genomic variation, such as single nucleotide polymorphisms (SNPs), small tandem repeats (STRs), variable tandem repeats (VNTRs), copy number variants (CNVs), insertion/deletions (indels), rare variants, chromosomal duplications/deletions, CpG islands and shores, allele specific methylation, and the like, throughout the genome, as well as in specific genes, gene families, and/or pathways visualized by brain imaging procedures, are related to subtypes of psychiatric disorders, and the relative response to different classes of therapeutic agents. There is a growing need to provide an interpretation of information provided by genetic testing (particularly multiple genetic tests) to the clinician, or learned intermediary, to aid in treatment and/or diagnosis. The articles of manufacture described herein may include interpretive logic configured to analyze the results of all of the assays and to provide interpretive comments, wherein the interpretive logic is encoded for processing on a processor or any other easily accessed and reviewable form. The interpretive comments may indicate the effect of any identified genomic variant on the regulation of neurotransmitter activity, ionic channel function and/or metabolism. Providing this information may allow a physician to properly understand the interpretation of a genomic variation, and may allow compliance with regulatory guidelines. Unfortunately, without providing a proper context, genomic test results can lead to confusion rather than clarification, particularly in a clinical setting. In subsequent paragraphs, particular language of interpretation for various genomic biomarker test results will be provided. Within these descriptions, clarification regarding both the potential benefits and limitations of biomarker analysis is provided, as well as recommended therapeutic interventions based upon the genome or other relevant biomarker of the patient.

Genes associated with neurotransmitters, ionic channels (calcium, sodium and potassium) and metabolic pathways (immune and inflammatory), have been found to be abnormal in patients with various neuropsychiatric disorders. For instance, genes which regulate serotonin pathways, including genes coding for receptors, metabolism and reuptake mechanisms, are associated with mood disturbances. Furthermore, other genetic-neurotransmitter pathways, including dopamine, norepinephrine and glutamate may be associated with depression or risk of dementia. Regarding ion channels, pathological states in the brain can result from changes in which alter membrane excitability. Phenomenologically, alterations in ion channels may be seen clinically as paroxysmal, recurrent, or intermittent disturbances. Genes related to cerebral metabolism, such as methylation and the like, also impart changes with neuropsychiatric implications. For example, genes related to oxidation, mitochondrial function, proteasomal degradation and insulin and its associated second messenger systems (gene pathways) may also have nuropsychiatirc implaications. Unfortunately, what is not well-understood is how to apply such genetic or expression-related information to patient treatment in a robust and useful manner, particularly for neuropsychiatric disorders. Genes which regulate immune processes are also relevant in clinical assessments as variants in glial cell activity have been associated with depression, schizophrenia, bipolar disease and dementia.

Unfortunately, the heterogeneous nature of gene findings in neuropsychiatric disorders suggests that neuropsychiatric disorders themselves, as mentioned above, are heterogeneous and require a dimensional, rather than categorical approach. By analyzing disorders using a spectrum of biomarkers, such as SNP-based gene analysis, subtypes of neuropsychiatric conditions can be differentiated and treated in a personalized manner. This analysis may allow a deeper understanding of a patient's health across a variety of neuropsychiatric categories. Further, the employment of such analysis will allow mental health professionals to treat individuals with more specific and targeted interventions. Therefore, the approach described herein may be used to reveal genomic influences on trait components of a variety of neuropsychiatric disorders (regardless of categorical classification) and may help identify subpopulations of patients that can benefit from more targeted pharmacotherapy. This approach has proven difficult, however, at least because it is difficult to know which collection of biomarkers are sufficient and useful for this purpose.

As an example, a genomic variation in one of the family of genes that regulates the dopamine pathway can be associated with reduced levels of this neurotransmitter, along with parallel changes in an individual's behavior. Patients with variation in the dopamine pathway differ not only in their symptoms, but also in their response to therapies as well. However, such patients may be otherwise hard to identify based solely on their behavior. By examining a variety of biomarkers, a deeper understanding of a patient's treatment needs may be achieved. For example, a mood complaint, such as depression, can be a consequence of genomic defects that affect the metabolism of the serotonin pathway, or can be a consequence of a genomic defect that regulates the dopamine pathway, the glutamate pathway, or some other pathway that affects neurotransmitter metabolism. As a similar example, depression can be etiologically associated with a genomic variation in the glutamate pathway in one individual, and with a genomic variation related to the dopamine or the norepinephrine pathway in another. Thus, it would be beneficial to provide a method and articles of manufacture (including systems, reports, kits and the like) that are capable of conveniently, effectively and efficiently informing a physician on a variety of relevant factors that will guide patient care.

The recognition of the distinction in the genomic heterogeneity related to the expression of subtypes of psychiatric disorders has important therapeutic implications. Frequently, an individual with a mood disturbance does not respond favorably to a specific first class of therapeutic agents, but may respond to a different second class of therapeutic agents. As an example, an individual who is experiencing depression due to a genomic variant in the dopamine pathway that causes a metabolic defect will not respond, or will respond less favorably, to a serotonin modulating agent. In clinical practice, this can happen when a psychiatrist treats a patient with depression who possesses genomic variation associated with a dopamine-related defect with a serotonin modulating drug, like sertraline or paroxetine, instead of a dopamine modulating drug such as buproprion. In these instances, the drug may produce a worsening of symptoms instead of improving them.

Conversely, an individual with genomic variation associated with the metabolism of the serotonin pathway will respond less favorably to a dopamine modulating agent. Frequently in such patients, depressive symptoms will not improve or may, in fact, worsen. Unfortunately, psychiatrists currently administer medications for depression solely on a trial and error basis. The lack of diagnostic specificity frequently leads to ineffective treatments or a delay in the proper treatment.

Thus, a common problem in the management of all psychiatric disorders is a lack of diagnostic specificity and/or treatments which are not coupled to the unique neurobiological mechanisms associated with psychopathology. Provided herein is a method of using the analysis of biomarkers as an aid to diagnosis and as a choice of therapeutic treatment.

It is further an object of this description to set forth a dimensional model based upon the specific functional axes related to neurochemical pathways and anatomical regions in the brain that are causally associated with various neuropsychiatric conditions. These axes each have associated genomic, epigenetic, transcriptomic, proteomic, metabolomic or brain imaging biomarkers which may be probed. The ability to accurately identify variations of functionally related biomarkers, as taught herein, represents an important advance in the field of mental health.

Lab diagnostics in central nervous system (CNS) disorders often lack specificity and sensitivity. A novel solution described herein is to recognize that an integrated approach to the diagnosis of these disorders, rather than a single lab modality, may be anticipated. Thus, while there may be limitations to diagnosing a disorder based upon the utilization of genomic-based technology exclusively, the application of an analysis of biomarker signals integrated under a broader diagnostic framework, which includes one or more of genomic analysis, epigenetic analysis, transcriptomic analysis, proteomic analysis, metabolomics analysis, and the like, will increase the confidence of the diagnostic signal and lead to previously unrealized treatment efficacy and specificity. These should also be recognized as part of the dimensional model herein described.

For example, it has long been suspected that a cluster of genes is likely to contribute to a gene dosing effect in schizophrenia. However, even when detecting these genes, it is unclear whether any of these genes are actually expressed. Thus, it is not sufficient to know that a patient has a genetic polymorphism linked to an increase in risk; there is a requirement in the field to develop a more holistic analysis which should also include, in addition to risk genes, the actual detection of altered gene expression. Gene expression, in addition to gene inheritance, may provide a more reliable use of biomarkers in neuropsychiatry to understand more fully the dimensional model herein described.

Expression may be based upon unique transcriptional analysis, including epigenetics, e.g., methylation of specific CpG islands and allele-specific methylation, and post translational modifications and/or protein expression and modification. Several examples will be set forth below related to specific disorders but the teaching can be more generally applied to other conditions not mentioned.

Thus, in some embodiments, the approach outlined is a teaching which requires an analysis at multiple levels of molecular biology: autosomal and sex-chromosomal variation, methylation and/or histone modifications, transcriptomics, proteomics, metabolomics and the like. Each of these signals can be incorporated to provide a more complete understanding to a specific patient Treatment resistance in psychiatry is an area where there is a particular pressing need to provide biomarker-based tests that collects relevant biomarkers and presents the results of these biomarkers to a physician in an interpreted manner. As a specific example, within a 15-month period after having been diagnosed with depression, sufferers are four times more likely to die as those who do not have depression. Almost 60% of suicides have their roots in major depression, and 15% of those admitted to a psychiatric hospital for depression eventually kill themselves. In the U.S. alone, the estimated economic costs for depression in 1990 exceeded $44 billion. The World Health Organization estimates that major depression is the fourth most important cause worldwide of loss in disability-adjusted life years, and will be the second most important cause by 2020.

A variety of pharmacologic agents are available for the treatment of depression. Significant success has been achieved through the use of serotonin reuptake inhibitors (SRIs), norepinephrine reuptake inhibitors (NERIs), combined serotonin-norepinephrine reuptake inhibitors (SNRIs), monoamine oxidase inhibitors (MAOIs), glutamate inhibitors and/or other compounds. However, even with these options available, many patients fail to respond, or respond only partially to treatment. Additionally, many of these agents show delayed onset of activity, so that patients are required to undergo treatment for weeks or months before receiving benefits.

Traditional therapies can also have significant side effects. For example, more than a third of patients taking SRIs experience sexual dysfunction. Other problematic side effects include gastrointestinal disturbances, often manifested as nausea and occasional vomiting, agitation, insomnia, weight gain, and/or the onset of diabetes.

Patients that fail to respond to these standard/traditional depression therapies may be classified as suffering from treatment resistant depression (TRD, also referred to as refractory depression or treatment refractory depression). TRD is often described as depression that does not respond to different antidepressant medications from more than at least two different classes, or different treatments.

In the clinic, 40-50% of depressed patients who are initially prescribed antidepressant therapy do not experience a timely remission of depression symptoms. This group typifies treatment-refractory depression, that is, a failure to demonstrate an "adequate" response to an "adequate" treatment trial (that is, sufficient intensity of treatment for sufficient duration)). Moreover, about 20-30% of depressed patients remain partially or totally resistant to pharmacological treatment.

There is increasing evidence implicating the role of neurotransmitters in depression, in particular the monoamines serotonin, noradrenaline, dopamine, as well as the excitatory amino acid glutamate. Many of the tricylic antidepressants (TCAs), selective serotonin reuptake inhibitors (SSRIs) and monoamine oxidase inhibitors (MAOIs) effective in the treatment of depression increase the availability of the catecholamines (noradrenaline and dopamine) and indolamines (serotonin) in the CNS. The clinical efficacy of these agents has given rise to the catecholamine-indolamine hypothesis of depression. This theory postulates that a certain level of amines and/or receptor sensitivity to catecholamines functions to generate a normal mood. Receptor insensitivity, a depletion of monoamines, or a decrease in their release, synthesis or storage has been postulated to lead to depression.

Personalized medicine is considered a young but rapidly advancing field of healthcare that is informed by each person's unique clinical, genomic, and environmental information. Because these factors are different for every person, the nature of diseases—including their onset, their course, and how they might respond to drugs or other interventions—is as individual as the people who have them.

The goal of personalized medicine is to customize or individualize treatments based on the particular environmental, genomic profile, and clinical information specific to a patient, thereby allowing accurate predictions to be made about a person's susceptibility of developing disease, the course of disease, and its response to treatment.

In order for personalized medicine to be used effectively by healthcare providers and their patients, these findings must be translated into precise diagnostic tests and targeted therapies. This has begun to happen in certain areas, such as testing patients genetically to determine their likelihood of having a serious adverse reaction to various cancer drugs. Recently, work has begun to extend this testing to drugs used in other fields, including psychopharmacology.

The complete sequencing of the human genome provided a first step towards understanding the biological workings behind countless medical conditions. Although the field of personalized medicine is advancing at a fast pace, as new disorders are linked to particular genetic predispositions and mutations, adoption of such personalized markers for disorders and treatments has been slowed by the overwhelming amount of information available.

Although personalized medicine offers patients and clinicians numerous advantages, there are also increasing risks arising from the narrow focus and resulting myopia when examining complex disorders in light of only a few genomic associations. Medical practitioners are often caught between having too little information or too much information. If a medical practitioner examines only some of the genes which may be implicated in a disorder, he or she may miss essential information. Alternatively, providing information about too many contributing variations may prevent a concise diagnosis, resulting in confusion.

These problems are particularly present in the area of personalized medicine for use in treating psychiatric disorders. This patent application describes the heterogeneous nature of psychiatric conditions, and in particular some of the genomic variants and phenotypes that they are correlated with.

In particular, when prescribing treatment for resistance in psychiatry, there is a strong need to provide a means for reducing the overwhelming amount of genetic data available into a reduced and simplified format to guide a medical practitioner in treating these disorders.

SUMMARY OF THE DISCLOSURE

Described herein are methods and systems, including articles of manufacture such as reports, for guiding therapeutic treatment of neuropsychiatric disorders based upon a novel biomarker diagnostic system. For example, described herein are systems, methods and articles of manufacture relevant to treatment-resistant psychiatric disorders including depression, bipolar, schizophrenia, anxiety disorders, psychotic disorders and the like.

In general, the systems described herein provide a dimensional, rather than categorical, assay, screen, test, and/or report relevant to treating neuropsychiatric disorders. The dimensional assays, and dimensional assay reports, described herein, typically use a collection or set of biomarkers that are relevant to one or more areas useful for understanding pathophysiological pathways of the brain underlying many classes of neuropsychiatric disorders. These areas may be defined or described based on the anatomical and/or functional biological relationships, which correlate with the dimensional symptom spectrum of a particular condition. Of particular interest are three areas, which are described in greater detail below: limbic based the autonomic arousal area (or axis) which includes the amygdala and hypothalamic-pituitary-adrenal (HPA) axis; the emotional valence and reward and the executive brain function area (axis), which includes the prefrontal cortex, anterior cingulate and nucleus accumbens; and the domain which mediates synaptic strength and abnormal brain circuitry, long-term potentiation and long-term depression axis.

The autonomic arousal area (or axis) functionally relates to stress and autonomic hyperactivity. The functional brain circuits involved typically include the amygdala and hypothalamus. Patients with disturbances in this axis may display recognizable clusters of symptoms including heightened arousal, panic, intractable anxiety, PTSD and the like. The principle neurotransmitter pathways implicated for this area include the serotonin/norepinephrine neurotransmitter and corticotrophin/angiotensin pathways. Dysregulation of these pathways may result in problems of autonomic arousal. By example, genes that are part of larger gene families and one or more pathways may include, but are not limited to: serotonin transporter (SLC6A4 or SERT or 5-HTT or 5-HTTLPR), FK506-binding protein 5 (FKBP5), serotonin 5-HT-1A receptor (HTR1A or 5-HT1A), angiotensin-converting-enzyme (ACE), Neuropeptide Y (NPY), catechol-O-methyltransferase (COMT), and the like. Abnormal biomarker detection would indicate dysfunction in this axis with clinically associated disturbances in emotional vigilance, anxiety, panic, PTSD and the like. Potential treatments for this endophenotype, based upon identification of these biomarkers, may involve noradrenergic modulators (such as NRIs), angiotensin receptor blockers (such as Candesartan and the like), lithium or other agents which reduce autonomic hyperactivity.

The emotional valence and reward/executive brain function area (axis) relates to the pain/pleasure response may involve the functional brain circuits of the prefrontal cortex, ventral striatum, and nucleus acumbens regions of the brain. Dimensionally, individuals with dysfunction in this axis may exhibit abnormalities in motivation, attention, cravings, addiction and the like. The principle neurotransmitter pathway implicated in this axis is dopamine (dopaminergic); dysregulation of dopamine neurotransmission in these regions may result in dysfunction of this axis. Representative gene markers that are part of larger gene families and one or more pathways may include, but are not limited to: dopamine receptor D2 (DRD2), dopamine transporter (SLC6A3 or DAT1), catechol-O-methyltransferase (COMT), and/or monoamine oxidase A (MAOA). Potential treatment for dopamine hypoexpression genes based on the biomarkers examined may include transcranial magnetic stimulation, stimulants, Buproprion, Seligiline, and/or COMT inhibitors. Over expression of this axis, for example in individuals with the COMT Met158Met genotype, leads to a different and unique cluster of symptoms characterized by dopamine over expression, owing to reduced dopamine degradation. These symptoms may include addiction proclivity, dopamine induced mania and the like. Potential treatment for dopamine hyperexpression based on the biomarkers examined may include antipsychotics or S-adenosyl methionine, a COMT agonist which may potentially lower dopamine by enhancing its degradation.

Cognition, memory, excitatory neurotransmission, and long-term potentiation are all related to the strength of synaptic pathways. This axis may include the functional brain circuits in the hippocampus as well as the neurotransmitter systems such as the glutamate neurotransmitter pathway, calcium channels, sodium channels, and the like. Dimensionally, individuals with dysfunction in this axis, herein referred to as LTP-LTD, may exhibit irritability, high recurrence rates, lower thresholds for exacerbations, cyclical mood or cognitive disturbances and the like. Examples of gene markers in this axis may include: alpha-1 subunit of a voltage-dependent calcium channel (CACNA1C or CACH2 or CACN2 or CaV1.2), alpha-1 subunit of a voltage-gated sodium channel (SCN1A or Nav1.1 or FEB3), glutamate transporter (SLC1A1), ankyrin 3 (ANK3 or ANKYRIN-G), and/or brain-derived neurotrophic factor (BDNF). This teaching is meant to point out representative examples of genes affecting the various axes referred to herein, but by no means is a comprehensive listing of all of the potential variation in and amongst these gene families or pathways. Potential treatments for genomic variation leading to excessive excitatory neurotransmission in this axis may include: lithium, Lamotrigine, Valproic Acid, Nimodipine and other calcium channel blockers, memantine, magnesium, Vitamin D or any agent which modulates ionic channels in the brain. Furthermore, the choice whether to use a calcium channel based mood stabilizer or sodium channel modulator may be further assisted by an analysis of these variants. Ankyrin, the gene encoded by ANK3, is enriched at the nodes of ranvier and mediates the aggregate activity of sodium channels in these axonal pathways. Therefore, variants of ANK3 may selectively respond to sodium channel inhibitors such as lamotrigine, riluzole, and other sodium channel modulators.

Information, and particularly biomarker information indicating dysfunction in any, or preferably all, of these axes may be helpful. Thus any of the systems (including the methods and reports) described herein may include at least one biomarker indicating dysfunction for a particular group, or multiple biomarkers for each group. A three-axis group may also include information on at least one biomarker for each of these pharmacodynamic areas just described.

In some variations a system, method, or article of manufacture may include a fourth axis related to metabolism. This axis may be a pharmacokinetic axis, relevant to metabolism (including drug metabolism). For example, a metabolism area (axis) may include one or more biomarkers for cytochrome P450 mediated hepatic degradation related to pharmacokinetics, methylation, neuroimmune function, blood brain barrier status, brain lipid signaling and insulin pathways. For example representative gene markers may include, but not limited to: cytochrome P450 (CYP2D6, CYP2C19, and CYP3A4), P-glycoprotein (ABCB1), serotonin receptor 2C (HTR2C or 5-HT2C), methylenetetrahydrofolate reductase (MTHFR), melanocortin 4 receptor (MC4R), and/or insulin-degrading enzyme (IDE). This teaching is meant to point out representative examples of genes affecting the various axes referred to herein, but by no means is a comprehensive listing of all of the potential variation in and amongst these gene families or pathways. For example, the list of gene variants described herein is not intended to be exhaustive, but is meant to include other variants that may be linked to the same genetic locus, or variants carrying similar information about the variants mentioned. Near-equivalent variants may be analyzed together to get the same information those mentioned herein.

Thus, in one variation a method, system or article of manufacture may feature at least one biomarker from each of these axes: the autonomic arousal axis, the emotional valence and reward and executive brain function axis, the LTP/LTD synaptic strength axis. In some variations the method, system or article of manufacture may also include one or more marker from the metabolism axis. The clusters of genetic biomarkers related to each (or all) of these axes can be used both for clinical and research purposes. In use, reports indicating the results of biomarkers from these axes can provide a significant amount of information to alert the clinician to a potential abnormality in a prominent neuroanatomical pathway. The pathways implicated in these axes mediate and form the biological basis of behavior, including assessment of external risk and fear (autonomic arousal axis, axis I), novelty seeking, motivation and evaluation of significance (emotional valence, addiction and reward and executive brain function axis, axis II), and synaptic processes/cortical circuits including memory and long term potentiation (axis III).

The systems devices and methods described herein can also be used to help treat the patient by providing patient-specific therapeutic information. This "theranostic" information may allow tailored treatment of neuropsychiatric disorders. Currently, the majority of agents used to treat neuropsychiatric disorders relate to the modulation of serotonin pathways, norepinephrine pathways, dopamine pathways and glutamate pathways; genetic biomarkers associated with these pathways can therefore be employed for treatment decision processes. It may be of particular use to include pharmacodynamic biomarkers along with pharmacokinetic biomarkers. In addition to specific genes related to the metabolism of drugs, the identification of genomic variants related to insulin or lipid metabolism and the like, may lead to the employment of novel therapeutic interventions which are not typically classified as being directly psychotropic. These may include, for example, the use of peroxisome proliferator-activated receptors (PPARs) agonists in bipolar disease, methylfolate for depression associated with variants in MTHFR-related genes, and the like, based on the results of the biomarker assay as interpreted by the systems and methods described herein.

Also included herein are compositions and for the identification and treatment of subjects such that a theranostic approach can be taken to determine the effectiveness of a therapeutic intervention (such as a pharmaceutical or non-pharmaceutical intervention). The methods and reports described herein may allow a reduction in the risk of developing adverse outcomes and may enhance the effectiveness of the intervention. Thus, in addition to diagnosing or confirming the predisposition for a neuropsychiatric illness, the methods and articles of manufacture described also provide a means of optimizing the treatment of a patient by guiding clinicians in choosing appropriate treatments for their patients in a genotypical (or other biomarker) specific fashion. For example, provided herein is a theranostic approach to treating and preventing neuropsychiatric disorders by integrating patient-specific diagnostics and therapeutics to improve treatment of a patient.

In some variations, the dimensional assay should include at least one marker from each of the three axes described (and in some instances, a fourth from metabolic axis). These markers do not, by themselves, indicate a particular diagnosis for a neuropsychiatric disorder (e.g., they are not traditional categorical, or categorical, or etic biomarkers associated with pathway disorders). These areas provide dimensional and phenomenological data about inherited predispositions and vulnerability to pathological states, and thus may provide clinical information useful to treat a variety of neuropsychiatric disorders.

As mentioned above, in some variations the methods, kits and reports described herein provide an integrated analysis of a set of biomarkers, such as genetic markers, epigenetic markers, transcription markers, protein markers, metabolism markers and/or functional brain imaging. The set of biomarkers may be specifically selected to optimize the therapeutic information provided, as described in greater detail herein. The application and incorporation of such a methodology will enhance diagnostic certainty where analysis of any of these markers separately and in isolation provides only limited insight.

One variation of a method of presenting patient-specific and dimensionally based information relevant to the treatment of a neuropsychiatric disorder includes a process for biomarker detection. Any appropriate method for biomarker detection may be used (e.g., gene detection such as SNP, CNV, indel, STR, VNTR, CpG, allelic methylation, etc. . . . ). Biomarker detection may be determined on one or more appropriate platforms. Various platforms may include, but are not limited to Affymetrix, Taqman, Sequenom or Illumina and the like. These platforms can be array-based, PCR-based, or any other single-base detection modalities or sequencing modalities. Development of these platforms can be further validated by robust multi-chip analysis algorithms and subjected to ontological analysis by a variety of different bioinformatics tools. Following detection, a report may be generated, including a description of the physiological significance of the results of the biomarker tests, and additional interpretive information.

The interpretive information provided may include a score or weighting index indicating a confidence level for the interpretive information. This score or index may indicate the number of studies supporting the interpretive comment, the size of the studies supporting the interpretive comment and/or the existence of any disputing or contradictory studies. Some variations, references or links to references may also be provided. Both the testing and the report may be configured to extract patient information most relevant to treatment.

In general, the interpretive analysis may indicate or describe a potential association with a disorder and/or dysfunction of brain activity. For example, if the biomarker for brain dysfunction indicates a genetic variant that is associated with higher rates of disorder or dysfunction (e.g., PTSD, stress disorders, anxiety disorders, etc.), metabolic disorder, etc., as described herein (including in the examples) for each of the various biomarkers indicated.

Several genome-wide association studies (GWAS) have suggested that the combination of several genes, analyzed in a specific cluster, may account for various psychiatric and neurological disorder phenotypes. The observations of such studies are likely incomplete, because they fail to take into account altered protein expression and epigenetic factors. For example, the serum proteome has high complexity with thousands of non-redundant proteins due to multiple post-translational modifications.

Thus, an additional step in the methods and systems for examining and reporting on clinically relevant biomarkers in neuropsychiatry may include an examination of RNA expression. RNA expression analysis may further refine diagnostic specificity as it relates to the actual encoding of DNA in regions of particular interest. Suitable modalities to include are expressed sequence tag analysis and the like.

Another step may include an analysis of the actual protein expression of an altered gene through proteomics. Therefore, one or more proteomic based technologies may be incorporated into the integrative platform described herein. For example, subtractive proteomics, which compares two or more proteomes to identify proteins that are specifically enriched or depleted, may be used as one peptide substrate mapping strategy. Isotope affinity tags are another suitable method of protein detection which may be used.

In some variations DNA methylation analysis may be incorporated into the systems, methods and reports described herein. The methylation status of CpG islands, histones, or allele specific methylation, may correlate with the activity of transcribed genes, which are generally unmethylated. Technologies to assess DNA methylation, including bisulfite reactions are typically hampered by variability, but may benefit from the combined and tiered approach described herein. PCR-based assays and other improvements to the state of the art may also be incorporated into the method, systems, kits and reports described below.

The human genome can be methylated in regions called CpG islands, which control gene transcription through the methylation of methyl-CpG binding domains. When methylated, gene inactivation occurs due to chromatin condensation. In some variations, this epigenetic indicator (e.g., methylation of one or more region of DNA) may be detected and interpreted. Methylation detection methods may determine methylation patterns in a particular genomic locus. Also, specific alleles, some of which are alleles that are part of a SNP, can be methylated. Histones can also be methylated which can impact how a gene is expressed. Various methods can be employed to detect methylation of these genes and their surroundings which is well known to those skilled in the art. For example, Bisulfite methylation tests, methyl-sensitive restriction enzymes, or oligonucleotide reiteration test may be used.

Because CpG motifs are potentially modifiable by environmental factors, they provide a plausible biomarker by which medical interventions may have effects on gene expression. Gene-specific methylation patterns may offer potential molecular signatures of drug responsiveness in psychiatric disorders and may serve as a viable approach for revealing epigenetic processes in a patient's physiology such as medication noncompliance, substance use, hormonal fluctuations, and differences in metabolism.

A number of methods are available for the analysis of CpG methylation levels. Levels of 5-methyl-cytosine (5-mC) can be quantified by enzymatic hydrolysis of the DNA, chromatographic separation of the nucleosides, and analysis by HPLC or MS. The Luminometric Methylation Assay (LUMA) targets all CCGG sequences in the genome by using methylation-sensitive restriction enzymes to discriminate methylated and unmethylated DNA followed by pyrosequencing. Repetitive element sequences, such as Alu, LINE-1 and Sat2, have also been analyzed in a number of studies, as a surrogate for genome-wide methylation levels; such analysis requires bisulfite conversion of cytosine to uracil followed by PCR. In the pyrosequencing analysis of repetitive elements, the PCR step amplifies a given region using primers outside the target sequence containing CpG sites so that both methylated and unmethylated sequences are amplified. This is followed by pyrosequencing of the region of interest. For methylation specific assays such as MethyLight, a Taqman quantitative real-time PCR assay is performed, using primers and probes that are methylation specific and require all CpG sites in the region to be methylated for amplification to occur.

The "methylation density" model suggests that the proportion of methylated cytosines across a region, rather than at any specific position, controls chromatin conformation and thus the transcriptional potential of a given gene. Consistency of DNA methylation patterns is surprisingly strong across many somatic tissues, including brain and lymphocytes. For example, in an examination that included lymphocytes, inter-tissue correlation of 0.95, and suggesting substantial validity for peripheral measurement of DNA methylation as a surrogate for brain methylation status.

Examples of methylation analysis as a "post intervention" biomarker are provided below. These include analysis of the methylation status of the serotonin transporter, COMT, MTHFR and other clusters of functional genes represented in our Axis model. The methylation level of the 5-HTT promoter region can cause effects of 5-HTTLPR on 5-HTT mRNA production. However, this effect is modest and thus, other cis- and trans-acting elements have been proposed to be involved in the regulation of the 5-HTT gene expression, such as the CpG island. Methylation of the promoter region of 5HTT decreases gene expression leading those individuals with long alleles to look more like those with short alleles and carriers of this allele might be particularly likely to show behavioral effects in response to down-regulation resulting from promoter methylation. The weighted average of loci for CpG residues from CpG1 (bp 25586514) to CpG71 (bp 25587180) can be used as index for methylation density in this region. MTHFR T/T genotypes for rs1801133 or hypomethylation of the CpG islands of the MTHFR gene may participate in the control of intracellular Ca(2+) by altering expression in inositol 1,4,5-triphosphate receptor, and S100 calcium binding protein, suggesting that hypomethylation of MTHFR may involve disruption of intracellular calcium. The increased influx of calcium in neurons has been associated as a pathophysiological event in bipolar disease and in particular in individuals with genetic variants of the calcium channel. COMT promoter CpG islands have been detected to be hypomethylated in DNA derived from the saliva in SCZ and BD compared to the control subjects and the observation that S-adenosyl methionine is effective in ameliorating aggressive symptomatology in schizophrenic patients with low catechol-o-methyltransferase (COMT Met158Met variants) supports this notion. CpG-island microarrays have found psychosis-associated DNA-methylation differences in numerous loci, including two hypomethylated glutamate-receptor genes— one near WDR18, located ~10 kb upstream of the NMDA-receptor-subunit gene NR3B and another in the promoter of the AMPA-receptor-subunit gene GRIA2. Other examples of methylation detection of specific CpG promoter regions associated with the amygdala-HPA axis, the cortical-subcortical dopamine axis, and the ion channel based LTP-LTD channel are also anticipated. Analysis of these critical regions to determine methylation or demethylation of CpG binding domains can be used to determine if a therapeutic intervention has led to a desired effect on gene activation or inactivation.

Methylation detection may be a useful tool as a neuropsychiatric biomarker in the systems, reports and methods described herein for: (1) predicting drug response by measuring gene inactivation in responders versus non-responders in a region of interest; and (2) analyzing markers in disease detection. For example, methylation detection has proven helpful for treatment of lupus patients by observing hypomethylation of DNA in the circulation of these patients. Similarly, the methylation status of GSTP1 is being explored as a marker for prostate or colorectal cancer. Methylation is also being explored as an indicator of drug response. For example, in breast cancer, low methylation of PITX2 in lymph nodes may predict recurrence after Tamoxifen treatment, and in glioblastoma, MGMT methylation may predict response to alkylating agents. In psychiatry and neurology, examples of methylation of particular genes and pathways may also be important, including analysis of BDNF, serotonin transporters and the like. As mentioned above, the combination of an epigenetic indicator, such as methylation, in conjunction with genetic markers in the locus identified herein and/or protein expression makers may prove substantially more powerful and reliable. Thus, an integrative biomarker assay could include specific analysis of gene methylation patterns in critical brain pathways such as those described herein.

In some variation it may be beneficial to examine protein levels and/or expression for one or more biomarkers. For instance, in some the methods and/or articles of manufacture may be configured to examine one or more proteins associated with the inflammatory pathway. Inflammation may be particularly relevant when examining the second axis, which concerns limbic effects (emotional valence, attention, etc.), as inflammation may indicate extensive activation of limbic structures. Biomarkers indicating inflammation or disruption of the blood-brain barrier that may affect the limbic axis may include anti-NMDAr antibodies, S100Beta, MMP-9, anti-nuclear antibodies (ANA), etc. These biomarkers may be particularly helpful in treating psychotic states, particularly in the acute phase, when the markers may be up-regulated. In any of the variations described herein a biomarker may include a protein that is examined as described. For example, brain imaging modalities which can provide relevant clinical data regarding neuropsychiatric symptomatology across the axis described above may include: fMRI, DTI, and MRS (magnetic resonance spectroscopy). For instance, diffusion tensor imaging demonstrated decreased white matter integrity, indicated by lower fractional anisotropy and longitudinal diffusivity, in the ANK3 rs10994336 risk genotype in the anterior limb of the internal capsule. Further examples include association of the val(158) allele with lower blood oxygen level-dependent ("BOLD") response in ventromedial and dorsomedial prefrontal cortex compared to val(158) non-carriers, whereas met(158) homozygotes showed lower BOLD response in the posterior cingulate and precuneus compared to val(158) carriers compatible with a hypothesis on the role of COMT val(158) met genotype in tonic and phasic dopamine levels in brain. Further examples are reported herein.

In some variations, the biomarkers may be examined for a particular patient over time. For example, biomarkers in any or all of the axes examined may be analyzed before, during or after a treatment. Thus, the methods and articles of manufacture may be used to monitor treatment and/or progression of a neuropsychiatric disorder.

In general, any of the genes described herein may be used as biomarkers by testing for polymorphisms, mutations, insertions, deletions, translocations, methylation, histone methylation and/or deacetylation, etc. The proteins expressed by any of these genes may also be tested for expression level, localization, folding (or miss-folding), and the like.

The methylation status, including hypo- and hyper-methylation of certain genes may be a marker of neuropsychiatric disorder. In general, epigenetic modulations may play an important role in fine-tuning of gene expression in response to environmental factors. For instance, using quantitative methylation specific PCR, MB-COMT promoter has been seen to be hypo-methylated in DNA derived from the saliva in schizophrenia compared to control subjects, suggesting that DNA methylation analysis of MB-COMT promoter in saliva can potentially be used as an epigenetic biomarker for disease state. Further, the CpG at T102C of the HTR2A polymorphic site and neighboring CpGs were approximately 70% methylated both in the patients and controls. qMSP analysis revealed that the cytosine of the T102C polymorphic site was significantly hypo-methylated in SCZ compared to the controls. Thus, for example, Cytosine methylation of HTR2A at T102C polymorphic site in DNA derived from the saliva can potentially be used as a diagnostic, prognostic, and/or therapeutic biomarker in psychiatric conditions associated with psychotic symptoms.

As another example, the methylation status of retinoic acid-related orphan receptor alpha (RORA) has been implicated in Autism. Methylation of RORA was confirmed by bisulfite sequencing and methylation-specific PCR; this data has revealed decreased expression of RORA proteins in the autistic brain.

Methylation may also be used as a biomarker for heightened stress, intractable anxiety and other clusters of symptoms related to the amygdala-HPA axis. For example, SLC6A4 methylation levels appear to modify the effect of the number of traumatic events on PTSD after controlling for SLC6A4 genotype. Persons with more traumatic events were at increased risk for PTSD, but only at lower methylation levels. At higher methylation levels, individuals with more traumatic events were protected from this disorder. Depressive symptoms were more common among those with elevated buccal cell 5HTT methylation who carried 5-HT-TLPR short-allele. Thus hypomethylation of SLC6A4 may be used as a marker of depression and/or PTSD.

Protein expression may also be used as a biomarker. The examination of protein expression, including proteomics, may use an analytic method such as mass spectrometry, nanostring, and the like. Protein expression may also be examined by immunological methods (e.g., immunocytochemical detection). An abnormal protein may correspond to an abnormal biological state, whereas a gene abnormality is more trait dependent. Proteins that are found to be more prevalent in diseased patient samples compared to normal patient samples may be an important potential disease biomarker for disorders like dementia, schizophrenia, autism, bipolar, anxiety, depression and the like. However, a search for any particular biomarkers in disease-free or asymptomatic individuals is neither cost effective nor efficient. Therefore, it may be significantly more effective to combine an assessment of genetic risk and/or epigenetic risk with a proteomic analysis.

It should be noted that there currently exist commercial assays which are used for psychiatric diagnosis. A clear distinction between the systems, reports and methods described herein and these other tests includes the difference between analyzing pharmacodynamic (PD) genes and pharmacokinetic (PK) genes. In the latter example, PK genes provide information related to drug metabolism but do not provide any insight into trait dependent and specific neurochemical factors related to neuropsychiatric conditions. These trait-dependent factors, which are components of the current disclosure, include assessment of stress resilience, risk of impairments in reward mediated behaviors, risk of psychiatric decompensation or cyclical mood disturbances, subendophenotypes of depression, and the like. The systems described herein may examine biomarkers indicative of pharmacodynamic (PD) traits. These biomarkers test for the activity or interactions of one or more members of a biological pathway, including those pathways involved in neurotransmission. For example, the methods described herein may examine genes related to neurochemical imbalances. Such tests may be broadly applied to the genes involved in at least the following pathways: Serotonin, dopamine, norepinephrine, glutamate and the hypothalamic pituitary adrenal axis. Additional gene analysis also relates to calcium channels, sodium channels, potassium channels which are also relevant to neuropsychiatric disorders and response to particular interventions. Other genes of importance relate to metabolism. These genes include brain glucose utilization, methylation, inflammation and the like.

Specific genes within these areas are described in the paragraphs herein but are not limited to this disclosure. Thus, while the present invention describes polymorphisms in a specific serotonin gene, it is recognized that other polymorphisms in the serotonin pathway are contemplated as within the scope of this disclosure. Similarly, biomarkers in the glutamate pathway, dopamine pathway, norepinephrine pathway, and HPA axis may be examined as well. Gene detection such as SNPs, CNVs, indels, STRs, VNTRs and the like on various platforms known to those skilled in the art, such as the Affymetrix, Taqman, Sequenom or Illumina, can be utilized.

There are many variations of target nucleic acid amplification, including, for example, polymerase chain reaction (PCR), which has been disclosed in numerous publications. The most commonly used target amplification method is the polymerase chain reaction (PCR), which consists of repeated cycles of DNA polymerase-generated primer extension reactions. Each reaction cycle includes heat denaturation of the target nucleic acid; hybridization to the target nucleic acid of two oligonucleotide primers, which bracket the target sequence on opposite strands of the target that is to be amplified; and extension of the oligonucleotide primers by a nucleotide polymerase to produce multiple, double-stranded copies of the target sequence. The discovery of thermostable nucleic acid modifying enzymes has contributed to rapid advances in nucleic acid amplification technology.

The exemplary systems, screens and methods described herein may include assays for determining genetic indicators (including genetic polymorphisms), epigenetic markers (such as methylation status), and protein expression. Such assays may include known tests, assays or methods, which may be integrated or combined in known or novel ways. For example, diagnostic kits using "gene chip" technology may be used to determine genetic and/or epigenetic information about particular genes of interest, and may be integrated with protein indicators including immunoassays or the like.

For example, in some variations a neuropsychiatric—specific oriented kit may be provided. This kit (which may include an array) may be built to provide a practical and clinically relevant tool in practice in neuropsychiatry because it is able to translate GWAS-level research findings into a clinically practical framework. In this fashion, the benefit of focusing on a narrow and pre-selected group of SNPs, CNVs, repeats or indels relates to the application and context of the results in an integrative clinical setting.

As a specific example of the methods of diagnosing and/or treating a neuropsychiatric diagnosis described above, the inventor has applied one variation to identify psychiatric disorders based upon epistasis between 2 or more genes. For example, the inventor has discovered that individuals with a COMT Val/Val polymorphism in epistasis with the MTHFR T/T variant may display a phenotype characterized by a subcortical-type of mood disorder. These individuals commonly are abulic, dysthymic, and anergic. This phenotype may be expressed secondary to reduced prefrontal dopamine as a consequence of these genes being in epistasis, resulting in excess dopamine degradation. Thus, a system, report or method may examine the combination of COMT and MTHFR and/or dopamine neurotransmitter pathway genes. One or more genetic markers, epigenetic markers and/or protein expression may be examined to determine if a patient has or is at risk for the correlated abulic, dysthymic, and anergic phenotype.

In another example, the combination of serotonin short alleles and CACNA1C variants has also been linked by the inventor to a particular phenotype which may be specifically amenable to treatment, either to enhance treatment or to select between available treatments that would otherwise be seemly equivalent based only on the phenotype presented to the physician. For example, SSRI-induced mania may be higher in these patients.

For example, described herein are methods of presenting patient-specific dimensional PD information relevant to the treatment of a neuropsychiatric disorder. These methods may be used to improve psychiatric diagnosis, including depression, bipolar, schizophrenia, dementia, PTSD, anxiety and the like. In general, any of the methods, systems, and articles of manufacture described herein may use a specified cluster of biomarkers. As described herein, these clusters of biomarkers may include, for example, a representative set of biomarkers having particular relevance across a cross-section of neurotransmitter pathways, neurofunctional pathways, and/or neuroanatomical pathways. These biomarkers may be derived from the compacting and compression method described herein. For example, the biomarkers may include one or more biomarkers from each of the patient's autonomic arousal system, the patient's emotional valence, attention, reward and executive brain functions, and the patient's cognition and memory systems. Biomarkers examined may include SNPs, CNVs, indels, STRs, VNTRs, methylation, protein expression, functional brain MRI and the like. The selection of biomarkers, particularly those described in greater detail below, may indicate that status or functionality of neurotransmitter pathways, the patient's neuroimmune system and/or neuroendocrine system. The methods described herein may provide an integrative framework applied to these biomarkers in which component elements are interpreted in a holistic neural net framework, rather than reductionist fashion.

Further, any of the methods described herein may incorporate specific brain imaging modalities, including magnetic resonance spectroscopy (functional, tensor, etc.) and the like. The incorporation of these biomarkers and their interpretation in clinical practice is also described. In particular, the devices, systems and methods described herein allow interpretation of key subsets of biomarkers which address the translation of research findings into clinically meaningful data. For example, the systems, methods and reports described herein provide both raw biomarker test results for a specific and meaningful group of biomarkers, as well as interpretive data including clinical and research findings specific to the patient's biomarker test results. In some variations this interpretive data is ranked, weighted or indexed to provide a confidence level to the physician or medical professional. Thus, the methods, devices and systems described herein may provide clinical support which includes specific educational material for patients and/or clinicians.

Further, the methods, devices and systems described herein may provide analytical methods to enhance the signal to noise ratio related to the use of biomarkers in psychiatry.

In some variations, the methods of presenting patient-specific PD information relevant to the treatment of a neuropsychiatric disorder include the steps of: providing a patient identifier; presenting a description of a biomarker test result specific to the patient; presenting an interpretive analysis of the neurophysiological significance of the biomarker test result for the patient, wherein the interpretive analysis comprises pharmacodynamics information; and presenting a weighted index of confidence level for the interpretive analysis.

These methods may be used in order to improve treatment, and in some variations, may also be used to help identify and/or diagnose patients. In some variations, the methods may be used to help delineate specific treatment interventions based upon the results of the biomarkers.

The step of providing a patient identifier may include generating a report including any patient identifying mark, code, name, symbol, or the like. For example, the patient identifier may include a patient number or patient name. The patient name may be kept confidential in some variations. In variations in which the method includes providing a copy of the results, the results copy may include a written patient identifier as part of the copy of the results.

The step of presenting a description of a biomarker test result specific to the patient may include a listing or output of the raw result of the biomarker test and/or an amended form of the results. For example, when SNPs are used, the presence or absence of the derived allele on each chromosome may be provided. In some variations, the raw biomarker test result is not provided, but only a summary of the result is included (e.g., "the patient tested positive for . . . " a particular biomarker). In some variations, the test results may indicate a polymorphism, deletion, duplication, insertion, methylation level, methylated allele, expression level, expression localization, activity, or metabolites of one or more gene, protein, or neurotransmitter.

In general, any of the steps of presenting information (e.g., presenting a description, presenting an interpretive analysis, presenting a weighted index, etc.) may include generating a report including the presented information, or including the presented information on a single report. As discussed herein, the report may be a single page or multiple pages, both in written or digital formats.

The step of presenting an interpretive analysis of the neurophysiological significance of the biomarker test result for the patient, wherein the interpretive analysis comprises PD information, may include providing any appropriate type of interpretive analysis and comments. Appropriate interpretive analysis typically includes a description of the physiological significance of the biomarker test result. For example, the interpretive analysis may indicate associations with neuropsychological disorders, drug response, patient behaviors, treatment outcomes, or the like in patients with the same biomarker test results. The interpretive analysis may also include a description of the gene and/or protein, and/or biological pathway associated with the particular biomarker. In some variations the interpretive analysis may also include association studies, such as gene response association studies, describing or summarizing research and/or clinical studies on the biomarker and any associations based on the presence and/or absence of the biomarker.

In some variations the interpretive analysis may also include a visual representation of a region of the patient's brain affected by the underlying biomarker (e.g., the gene and/or protein being tested by the biomarker test). The visual representation may be generic (e.g., not taken from the actual patient's brain). Multiple visual representations (including alternative views, color views, animations, etc.) may be provided. The interpretive analysis may also include possible drug responses.

The results may be provided in hard copy (e.g., written form) or they may be electronic, including delivered as a web page, PDF, or other "virtual" document.

The step of presenting a weighted index of confidence level for the interpretive analysis may include indicating for all or some of the interpretive analysis an approximation of the confidence level for that particular portion of the interpretive analysis. For example, an index may include a "score" based on the reproducibility (or lack of reproducibility), the number of patients/subject's examined in the academic or clinical literature or references, the length of time studied, or the like. In general, these confidence level scores may be summarized in the report in a key, or they may be self-qualifying (e.g., the index may indicate "high," "medium" or "low" confidence values). In some variations the weighted index of confidence level may include alphanumerically indexing all or a portion of the interpretive analysis with a score indicating the type and/or number of studies supporting the interpretive analysis.

Any neuropsychiatric disorder may be addressed by the methods, devices and articles of manufacture described herein, particularly for treatment resistance. For example, the neuropsychiatric disorder examined may be selected from the group including: treatment resistant depression, bipolar depression, anxiety disorders, PTSD, schizophrenia, dementia, autism, and ADHD. In some variations the patient may not be diagnosed with a particular neuropsychiatric disorder; in some variations the methods, systems and reports described herein may be used as an aid in treating the patient.

Although the general method of presenting patient-specific PD information relevant to the treatment of a neuropsychiatric disorder includes only a single biomarker test result, it is of particular interest to examine and present patient-specific information about a set of biomarkers. In particular a set of biomarkers that include one or more markers from a subset of "axes" such as the patient's autonomic arousal system, the patient's emotional valence, attention, reward and executive brain functions, and the patient's cognition and memory systems. Each of these axes describes PD biomarkers; in some variations it may also be helpful to include one or more markers of PK biomarkers. Examples of specific markers are provided herein. In particular, depression (and treatment-resistant depression especially) may include one or more markers from each of patient's autonomic arousal system, the patient's emotional valence, attention, reward and executive brain functions, and the patient's cognition and memory systems. When examining other neuropsychiatric disorders, only one or two of these axes may be used, or entirely other axes may be chosen.

As mentioned, in some variations the biomarker provides information about the autonomic arousal system of the patient's brain. For example, the biomarker may be a marker of a gene, or a protein encoded or modulated by gene selected from the group consisting of: SERT, SLC6A4 (SERT), HTR1A, ACE, NPY, FKBP5, and other genes associated with heightened amygdala function. In some variations a biomarker provides information about the emotional valence, attention, reward and executive brain functions of the patient. For example, the biomarker may be a marker of a gene, or a protein encoded or modulated by gene selected from the group consisting of: COMT, sigma receptors, SNAP25, MAOA, SLC6A3, and DRD2. In some variations, the biomarker provides information about the strength of synaptic pathways (LTP). For example, the biomarker may be a marker of a gene, or a protein encoded or modulated by gene selected from the group consisting of: CACNA1C, SLC1A1, ANK3, and BDNF.

Also described are methods of presenting patient-specific PD information relevant to the treatment of a neuropsychiatric disorder including the steps of: presenting a description of a biomarker test result specific to a patient for at least one biomarker related to each of: the patient's autonomic arousal system, the patient's emotional valence, attention, reward and executive brain functions, and the patient's cognition and memory; and presenting an interpretive analysis of the neurophysiological significance of each biomarker test result for the patient, wherein the interpretive analysis comprises PD information. All of the variations and additional steps described above may also be applied to these methods.

Also described herein are methods of presenting patient-specific pharmacodynamics information relevant to the treatment of a neuropsychiatric disorder, the method comprising: providing a patient identifier; presenting a description of a plurality of biomarker test results specific to the patient; presenting an interpretive analysis of the neurophysiological significance of each of the biomarker test result for the patient, wherein the interpretive analysis comprises pharmacodynamics information; and presenting a visual representation of a brain region affected by each biomarker.

Articles of manufacture for assisting in the treatment of neuropsychiatric disorders are also described herein. For example, described herein are articles of manufacture comprising an interpretive neuropsychiatric report of patient-specific pharmacodynamics information relevant to the treatment of a neuropsychiatric disorder, the article of manufacture comprising: a report including a patient identifier; a description of a biomarker test result specific to the patient; an interpretive analysis of the neurophysiological significance of the biomarker test result for the patient, wherein the interpretive analysis comprises pharmacodynamics information; and a weighted index of confidence level for the interpretive analysis. The report is generally written, and the tangible medium of the report may be hardcopy (e.g., paper) or electronic (e.g., a digital file describing the written results). Thus, in any of the articles of manufacture described, the patient identifier and descriptions of the biomarker test results and interpretive analysis may be non-transiently formed on the report. The report may also be stored in any appropriate electronic medium (e.g., digital medium).

In some variations, the article of manufacture includes a plurality of descriptions of biomarker test results specific to the patient for a plurality of biomarkers, and may also include interpretive analyses of the neurophysiological significance of each of the biomarker test results for the patient.

As mentioned above, the interpretive analysis may further comprise a description of the physiological significance of the biomarker test result for the patient, a description of published studies describing similar biomarker test results, an indicator of possible drug responses, and/or a visual representation of a brain region affected by the biomarker.

In addition to the pharmacodynamics biomarker(s), the article of manufacture may also include a description of a biomarker test results for a pharmacokinetic biomarker.

The weighted index of confidence level may include an alphanumerical index of all or a portion of the interpretive analysis with a score indicating the type and/or number of studies supporting the interpretive analysis. The article of manufacture may also include a list of references specific to the patient's biomarker test result (the references may be part of the interpretive analysis).

As mentioned above, the biomarker test result may indicate a polymorphism, deletion, repetition, insertion, methylation, expression level, expression localization, activity, or metabolites of one or more gene, protein, or neurotransmitter. For example, an article of manufacture may include a test result and interpretive comments for a biomarker related to the autonomic arousal system of the patient's brain, such as a gene, or a protein encoded or modulated by gene selected from the group consisting of: SLC6A4 (SERT), HTR1A, ACE, NPY, and FKBP5. An article of manufacture may include a test result and interpretive comments for a biomarker related to the emotional valence, attention, reward and executive brain functions of the patient, such as a gene, or a protein encoded or modulated by gene selected from the group consisting of: COMT, MAOA, SNAP25, SLC6A3, and DRD2. An article of manufacture may include a test result and interpretive comments for a biomarker related to the patient's cognition and memory, such as a gene, or a protein encoded or modulated by gene selected from the group consisting of: CACNA1C, SLC1A1, ANK3, and BDNF.

In some variations of the articles of manufacture described herein, the article of manufacture may include an interpretive neuropsychiatric report of patient-specific pharmacodynamics information relevant to the treatment of depression, the article of manufacture comprising: a report including a description of a biomarker test result specific to a patient for at least one biomarker related to each of: the patient's autonomic arousal system, the patient's emotional valence, attention, reward and executive brain functions, and the LTP-LTD axis; and an interpretive analysis of the neurophysiological significance of each biomarker test result for the patient, wherein the interpretive analysis comprises pharmacodynamics information. The article of manufacture may also include a weighted index of confidence level for all or part of each interpretive analysis.

In some variations of the articles of manufacture described herein, the articles include an interpretive neuropsychiatric report of patient-specific pharmacodynamics information relevant to the treatment of a neuropsychiatric disorder, the article of manufacture comprising a report including: a patient identifier; a description of a plurality of biomarker test results specific to the patient; an interpretive analysis of the neurophysiological significance of each of the biomarker test result for the patient, wherein the interpretive analysis comprises pharmacodynamics information; and a visual representation of a brain region affected by each biomarker.

Also described herein are methods of diagnosing a neuropsychiatric disorder based on patient-specific dimensional information. For example, the methods may include the steps of: sampling a patient; testing the sample for at least one biomarker related to each of: the patient's autonomic arousal system, the patient's emotional valence, attention, reward and executive brain functions, and the patient's LTP-LTD axis; providing a report including the results of the biomarker test, an interpretive analysis of the neurophysiological significance of each biomarker test result, and a weighted index of confidence level for the interpretive analysis.

Systems for performing the methods described herein are also included, as are systems for generating the articles of manufacture (e.g., reports) mentioned above. For example, a system for generating a patient-specific pharmacodynamics report relevant to the treatment of a neuropsychiatric disorder may include: an input module configured to receive at least one biomarker test result specific to a patient for each of: the patient's autonomic arousal system, the patient's emotional valence, attention, reward and executive brain functions, and the patient's cognition and memory; an analysis module coupled to the input module and configured to generate an interpretive report from the plurality of biomarker test results, wherein the analysis module generates interpretive comment for each biomarker based on the test result.

Also described herein are systems for diagnosing or guiding a therapeutic treatment of a neuropsychiatric disorder comprising: an assay for determining the status of at least one biomarker related to each of: the patient's autonomic arousal system, the patient's emotional valence, attention, reward and executive brain functions, and the patient's LTP-LTD axis; and a report including the status of the biomarkers determined, an interpretive analysis of the neurophysiological significance of each biomarker's status, and a weighted index of confidence level for the interpretive analysis.

Also described herein are methods for simplifying and presenting patient-specific treatment information for the treatment of a psychiatric disorder, as well as customized reports presenting information to guide treatment of psychiatric disorders. In particular, described herein are reports and methods for presenting information on the treatment of treatment resistant psychiatric disorders based on patient-specific information.

In general, the methods of presenting information and the presentations (e.g., reports) described herein include the presentation of patient-specific data from a core set of genetic loci which the inventors have found to be critical to guiding the treatment of resistant forms of psychiatric disorders. Thus, the presentation provides epistatic information related to the core areas, axes, or loci discussed above. The axes (loci) may be referred to functionally (e.g., cognition and memory, etc.), neuroanatomically (e.g., hippocampal, limbic, etc.) or based on their principle neurotransmitter pathway (dopaminergic, glutamatergic, etc.).

For example, described herein is a method of presenting patient-specific treatment information for treatment resistant depression may include: presenting the patient-specific information for each of the core genetic loci in an epistatic group, and presenting interpretive comments for each the results. As just mentioned, the genetic loci forming a core epistatic group typically relate to genes/proteins having a functional relationship for a particular neurotransmitter pathway, and/or neuroanatomical location, and/or neurological function.

The methods and reports described herein may present the biomarker results for a patient (e.g., a patient genotype) in a single report including biomarker information from each or the four axes identified (or a subset of them), and also present interpretive comments based on the results. The interpretive comments may describe a likely drug response based on the outcome of the biomarker results. For example, a report may provide the genotypes for biomarkers of a particular epistatic locus, and may describe putative or definite links between the results of one or more biomarker and an expected clinical significance. The interpretive comments may describe the function of a particular gene generally, and may specifically describe the significance of the genetic result of the biomarker test for that gene (or all relevant outcomes/genotypes). For example, in relation to the SERT biomarker analysis: "patients with the S/S genotype do not respond as well to SSRI antidepressants and may experience more side effects," and/or "In SSRI non-responders who exhibit the S/S allele, consideration should be given to use of a non-SSRI."

In some variations, the systems and methods may provide a summary of the results.

Also described herein are articles of manufacture based on the concepts taught herein. One particular article of manufacture contemplated herein is a written or displayed report describing a relevant set of biomarkers, the results of the biomarker tests, and interpretive comments including in some variations genetic information that is patient-specific and relevant to treatment of a neuropsychiatric disorder. In some variations the report includes a section providing the patient's genotype. The report may also include interpretive comments for each of the axes tested. Finally, the report may include a weighting index that provides a confidence level for all or some of the interpretive comments.

In some variation the report is an electronic report. In other variations the report is a written report. The report may be coded to indicate the presence of a genetic polymorphism in each member of the core epistatic group. The report may also include a summary (e.g., a table, chart, etc.) that lists and summarizes the genotype test results; this summary may be on the first page or the top/front of the report.

The interpretive comments may be included for each biomarker examined after a description of the genotype result for that member. In general, interpretive comments may include treatment recommendations, references to scientific literature, and any other statement describing the significance of one or more genotype. Interpretive comments may provide interpretation of the significance of each of the genotypes. Interpretive comments may also provide interpretation of the significance of combinations of genotypes for different biomarkers tested, particularly those within the different axes. Interpretive comments may also provide information on the significance of particular patient phenotypes in combination with specific (including patient-specific) genotypes.

In some variations, the interpretive comments include a visual representation of the effected brain region, including a representational image of the neuroanatomical region affected by a polymorphism identified by a biomarker, for example.

Interpretive comments may be tailored to correspond to the biomarker result for an individual; in some variations, the interpretive comments are generically provided regardless of the biomarker result. In variations in which all of the possible interpretive comments are provided regardless of the biomarker results, interpretive comments that are relevant to the identified biomarker result may be highlighted.

In general, the report may highlight or separate out the biomarker results, particularly when the biomarker indicates the presence of a polymorphism or risk factor having therapeutic consequences. For example, in some variations results indicating polymorphisms may be highlighted. Highlighting may include presenting the text in a different font, color, point, or the like, including (but not limited to) boxing the text, indenting the text, boding the text, italicizing the text, underlining the text, or the like.

In one variation of the methods of presenting patient-specific and dimensionally based information relevant to the treatment of a neuropsychiatric disorder described herein, the method may include the steps of: presenting written biomarker test results specific to a patient for at least one biomarker for dysfunction in each of the following axes: (1) a patient's autonomic arousal system; (2) the patient's emotional valence, attention, reward and executive brain functions; and (3) the patient's long-term potentiation and long-term depression (LTP-LTD) function; and presenting an interpretive analysis of the neurophysiological significance of each biomarker test result for the patient, wherein the interpretive analysis comprises patient-specific information on response to a neurotherapeutic agent based on the biomarker test results.

In some variations, this method is directed specifically to methods of presenting patient-specific and dimensionally based information relevant to the treatment of depression or treatment-resistant depression.

In some variations, the step of presenting the interpretive analysis comprises presenting an association with a neuropsychiatric condition based on the biomarker test results. In general the methods and articles of manufacture described herein are useful for providing relevant and helpful treatment information that is not necessarily linked to a particular or specific diagnosis, and the methods described herein do not necessarily provide a diagnosis or a categorical diagnosis. Thus, there may be overlap or comorbid presentation of symptoms. In some variations, the methods and articles of manufacture may be used in conjunction with a traditional categorical diagnosis. For example, these methods and articles of manufacture may be used to aid in the treatment of patients suspected or identified as having a neuropsychiatric disorders selected from the group including: treatment resistance associated with depressive disorders, bipolar disorder, anxiety disorders, PTSD, schizophrenia, autism, and ADHD.

In any of the methods and articles of manufacture described herein, the step of presenting the interpretive analysis may further comprise presenting a description of a neurophysiological correlation with the biomarker test results. In particular, the method or article of manufacture may include a description (including a picture or visual representation) of a region of the brain affected by particular status of the biomarker. In some variations the methods and articles of manufacture include a visual representation of a brain region relevant to each biomarker (e.g., highlighting the neuroanatomical regions of pathways affected by variations or disruptions in the genes informed by the biomarker). For example, if a biomarker indicates a potential dysfunction in one of the three neuropsychiatric axes identified (e.g., the autonomic arousal axis, the emotional valence, attention, reward and executive brain function axis, and/or the long-term potentiation and long-term depression axis), the interpretive analysis may provide correlated clinical findings relevant to that potential dysfunction. The interpretive analysis may also specifically address treatment regimes, including any relevant therapeutic (e.g., drug, medical foods, etc.) interactions or suggestions. The interpretive analysis may indicate if one or more therapeutics is indicated or contraindicated given the biomarker result(s).

Any of the variations of methods and articles of manufacture may also provide a referral to a call center to receive additional interpretive information. Thus, in some variations, the methods may include a phone number, web address, or other contact information, and/or instructions for contacting a call center to receive additional information on the results of the biomarker testing. The call center may be staffed or automated, and generally provides additional expert advice and information on the biomarker results.

In general the step of presenting may include presenting written biomarker test results specific to a patient for a pharmacokinetic biomarker. The written results may be electronic ("virtual") or paper ("real") and may be delivered or accessible to a medical physician. The results may be secured so that they can be accessed only by a physician and/or in some variations the patient.

As mentioned, in some variations it may be helpful to include additional biomarkers outside of the three neuropsychiatric axes mentioned. In particular, it may be helpful to include biomarkers for pharmacokinetic (e.g., drug metabolism) pathways, such as cytochrome P450.

In general, the biomarker test results may indicate polymorphism, deletion, repetition, insertion, methylation level, allele specific methylation, expression level, expression localization, activity, or metabolites of one or more gene, gene family, pathway, transcript, protein, or neurotransmitter.

A biomarker for dysfunction in the patient's autonomic arousal system axis may be a marker of a gene, or a protein encoded or modulated by gene, selected from the group consisting of: SLC6A4 (SERT), ACE, NPY, FKBP5, and HTR1A. Similarly, a biomarker for dysfunction in the patient's emotional valence, attention, reward and executive brain functions axis may be a marker of a gene, or a protein encoded or modulated by gene, selected from the group consisting of: COMT, SLC6A3, and DRD2. A biomarker for dysfunction in the patient's long-term potentiation and long-term depression (LTP-LTD) function axis may be a marker of a gene, or a protein encoded or modulated by gene, selected from the group consisting of: CACNA1C, SLC1A1, ANK3, BDNF, and APOE.

Presentation of a biomarker for disruption of each of the autonomic arousal axis, the emotional valence, attention, reward and executive brain function axis, and the long-term potentiation and long-term depression axis provides a surprisingly compete picture for treating neuropsychiatric disorders. It may be important to include all three of these axes in the methods and articles of manufacture described herein because the combination of these three axes allows an accurate approximation of the majority of therapeutic interactions for neuropsychiatric treatments; although additional axes and/or biomarkers within these axes could be included, including at least one biomarker from each of these three axes allows the methods and articles of manufacture described herein to provide interpretive information relevant to the majority of therapeutic treatments, independent of the categorical classification of the diagnosis or suspected diagnosis.

For example, the step of presenting the interpretive analysis may include predicting the patient's response to a neurotherapeutic agent selected from the group consisting of: Lithium, norepinephrine modulators, angiotensin receptor blockers, dopamine augmenting agents, monoamine oxidase inhibitors, COMT inhibitors, S-adenosyl methionine, mood stabilizers, calcium channel agents, Racetam agents, Tianeptine or Transcranial magnetic stimulation. Thus the interpretive analaysis may specifically describe a patient's likely response/outcome for one or more (or all) of these therapeutic agents based on the results of the biomarkers described.

In some variations the methods and articles of manufacture include a survey or patient response questionnaire to be completed by the patient or the patient's physician addressing patient history and/or behavior. In some variations this information may help inform the analysis of the biomarkers, or it may be used to track the effect of a therapy. For example, a questionnaire may assess mood problems, memory difficulty, anxiety issues and health related issues in psychiatric patients, particularly those with two or more medication failures. One example of a questionnaire is provided below (see, e.g., FIG. 6). Thus, in some variations of the method described herein, the method may also include the step of requesting patient treatment history information.

In one variation a method of presenting patient-specific and dimensionally based information relevant to the treatment of a neuropsychiatric disorder includes the steps of: presenting in a report a description of a biomarker test result specific to a patient for at least one biomarker related to the patient's autonomic arousal system axis, wherein the biomarker is related to a gene or a protein encoded or modulated by a gene selected from the group consisting of: SLC6A4 (SERT), ACE, NPY, FKBP5, and HTR1A; presenting in the report a description of a biomarker test result specific to the patient for at least one biomarker related to the patient's emotional valence, attention, reward and executive brain function axis, the biomarker related to a gene or a protein encoded or modulated by a gene selected from the group consisting of: COMT, SLC6A3, and DRD2; presenting in the report a description of a biomarker test result specific to the patient for at least one biomarker related to the patient's long-term potentiation and depression (LTP-LTD) function axis, the biomarker related to a gene or a protein encoded or modulated by a gene selected from the group consisting of: CACNA1C, SLC1A1, ANK3, BDNF, and APOE; presenting in the report an interpretive analysis of the neurophysiological significance of the patient's autonomic arousal system axis biomarker test result, the patient's emotional valence, attention, reward and executive brain function axis test result, and the patient's long-term potentiation and long-term depression function axis, wherein the interpretive analysis comprises patient-specific information on response to a neurotherapeutic agent based on the biomarker test results; providing a visual representation of a brain region relevant to each biomarker; and providing a referral to a call center to receive additional interpretive information.

In one variation a method of presenting patient-specific and dimensionally based information relevant to the treatment of a neuropsychiatric disorder includes the steps of: presenting in a report a description of a biomarker test result specific to a patient for a SLC6A4 (SERT) biomarker related to the patient's autonomic arousal system axis, wherein the biomarker is related to a gene or a protein encoded or modulated by the SLC6A4 (SERT) gene; presenting in the report a description of a biomarker test result specific to the patient for each of the COMT, SLC6A3, and DRD2 biomarkers related to the patient's emotional valence, attention, reward and executive brain function axis, wherein the biomarker is related to the COMT, SLC6A3, and DRD2 gene or a protein encoded or modulated by these genes; presenting in the report a description of biomarker test results specific to the patient for at least the CACNA1C and ANK3 biomarker related to the patient's long-term potentiation and depression (LTP-LTD) function axis, the biomarker related to the CACNA1C and ANK3 gene or a protein encoded or modulated by the CACNA1C and ANK3 genes; presenting in the report an interpretive analysis of the neurophysiological significance of the patient's autonomic arousal system axis biomarker test result, the patient's emotional valence, attention, reward and executive brain function axis test result, and the patient's long-term potentiation and long-term depression function axis, wherein the interpretive analysis comprises patient-specific information on response to a neurotherapeutic agent based on the biomarker test results; providing a visual representation of a brain region relevant to each biomarker; and providing a referral to a call center to receive additional interpretive information.

In any of these methods and articles of manufacture described herein, the method or article may also provide a description of biomarker test results for biomarkers indicating dysfunction of metabolic (e.g., drug metabolism) including all of some of the following genes: 5HT2C, MTHFR, CYP2D6, CYP2C19 and CYP3A5.

Also described herein are articles of manufacture comprising an interpretive neuropsychiatric report of patient-specific and dimensional information relevant to the treatment of a neuropsychiatric disorder, the article of manufacture comprising: a written description of a biomarker test result specific to a patient for at least one biomarker for dysfunction in each of the following axes: (1) the patient's limbic based autonomic arousal system; (2) the patient's pre frontal-subcortical emotional valence, attention, reward and executive brain functions; and (3) the patient's synaptic mediated long-term potentiation and long-term depression (LTP-LTD) function; and an interpretive analysis of the neurophysiological significance of each biomarker test results for the patient, wherein the interpretive analysis comprises patient-specific information on response to a neurotherapeutic agent based on the biomarker test results. As mentioned, the interpretive analysis may include a prediction of the patient's response to a neurotherapeutic agent, and particular a neurotherapeutic agent selected from the group consisting of: Lithium, norepinephrine modulators, angiotensin receptor blockers, dopamine augmenting agents, monoamine oxidase inhibitors, COMT inhibitors, S-adenosyl methionine, mood stabilizers, calcium channel agents, Racetam agents, Tianeptine or Transcranial magnetic stimulation.

The article of manufacture may also include a written description of a biomarker test results for a pharmacokinetic biomarker (e.g., cytochrome P450, etc.).

As mentioned, any of the methods and articles of manufacture described herein may include a referral to a call center for receiving additional interpretive information. The article of manufacture may be electronic or printed. In general, the article of manufacture may indicate polymorphism, deletion, repetition, insertion, methylation level, allele specific methylation, expression level, expression localization, activity, or metabolites of one or more gene, gene family, pathway, transcript, protein, or neurotransmitter.

For example, the biomarker for dysfunction in the patient's autonomic arousal system axis may be a marker of a gene, or a protein encoded or modulated by gene, selected from the group consisting of: SERT, SLC6A4 (SERT), 5HT1a, ACE, NPY, FKBP5, and HTR1A.

The biomarker of the article of manufacture for dysfunction in the patient's emotional valence, attention, reward and executive brain functions axis may be a marker of a gene, or a protein encoded or modulated by gene, selected from the group consisting of: COMT, SLC6A3, and DRD2. The biomarker for dysfunction in the patient's long-term potentiation and long-term depression (LTP-LTD) function axis may be a marker of a gene, or a protein encoded or modulated by gene, selected from the group consisting of: CACNA1C, SCN1A, ANK3, and BDNF.

Also described herein are articles of manufacture comprising an interpretive neuropsychiatric report of patient-specific and dimensional information relevant to the treatment of a neuropsychiatric disorder, the article of manufacture comprising: a written description of a biomarker test result specific to the patient for at least one biomarker related to the patient's autonomic arousal system axis, the biomarker related to a gene or a protein encoded or modulated by a gene selected from the group consisting of: SLC6A4 (SERT), ACE, NPY, FKBP5, and HTR1A; a written description of a biomarker test result specific to the patient for at least one biomarker related to the patient's emotional valence, attention, reward and executive brain function axis, the biomarker related to a gene or a protein encoded or modulated by a gene selected from the group consisting of: COMT, SLC6A3, and DRD2; a written description of a biomarker test result specific to the patient for at least one biomarker related to the patient's long-term potentiation and long-term depression (LTP-LTD) function axis, the biomarker related to a gene or a protein encoded or modulated by a gene selected from the group consisting of CACNA1C, SLC1A1, ANK3, BDNF, and APOE; and an interpretive analysis of the neurophysiological significance of the patient's autonomic arousal system biomarker test results, the patient's emotional valence, attention, reward and executive brain function test results, and the patient's LTP-LTD axis, wherein the interpretive analysis addresses patient treatment, wherein the interpretive analysis comprises patient-specific information on response to a neurotherapeutic agent based on the biomarker test results; wherein the written description of the biomarker test results includes a visual representation of a brain region relevant to the biomarker; and a referral to a call center to receive additional interpretive information.

In one variation of an article of manufacture, the article is an interpretive neuropsychiatric report of patient-specific and dimensional information relevant to the treatment of a neuropsychiatric disorder, the article of manufacture comprising: a written description of a biomarker test result for a SLC6A4 (SERT) biomarker of the patient's autonomic arousal system axis, wherein the biomarker is related to a gene or a protein encoded or modulated by the SLC6A4 (SERT) gene; a written description of a biomarker test result specific to the patient for each of a COMT, SLC6A3, and DRD2 biomarker, related to the patient's emotional valence, attention, reward and executive brain function axis, wherein the biomarker is related to the COMT, SLC6A3, and DRD2 gene or a protein encoded or modulated by these genes; a written description of biomarker test results specific to the patient for at least the CACNA1C and ANK3 biomarkers, related to the patient's long-term potentiation and depression (LTP-LTD) function axis, the biomarker related to the CACNA1C and ANK3 gene or a protein encoded or modulated by the CACNA1C and ANK3 genes; an interpretive analysis of the neurophysiological significance of the patient's autonomic arousal system biomarker test results, the patient's emotional valence, attention, reward and executive brain function test results, and the patient's LTP-LTD axis, wherein the interpretive analysis addresses patient treatment, wherein the interpretive analysis comprises patient-specific information on response to a neurotherapeutic agent based on the biomarker test results; wherein the written description of the biomarker test results includes a visual representation of a brain region relevant to the biomarker; and a referral to a call center to receive additional interpretive information.

In some articles of the articles of manufacture described herein, the article may include a description of biomarker test results for biomarkers indicating dysfunction of metablic (e.g., drug metabolism) including all of some of the following genes: 5HT2C, MTHFR, CYP2D6, CYP2C19 and CYP3A5.

BRIEF DESCRIPTION OF THE DRAWINGS

FIGS. 1A-1D show pages 1-4 of a first exemplary report.
FIGS. 2A-2D show pages 1-4 of a second exemplary report.
FIGS. 3A-3J illustrate another example of an exemplary report as described.
FIG. 4 shows one example of a visual portion of an exemplary report.
FIGS. 5A-5M show another example of an exemplary report.
FIGS. 7A-7G show pages 1-7 of one variation of an exemplary report.
FIG. 8 shows another variation of an exemplary report similar to the report of FIGS. 7A-7G.

FIG. 9 shows another variation of an exemplary report similar to the report of FIGS. 7A-7G.

DETAILED DESCRIPTION

Figure 6:
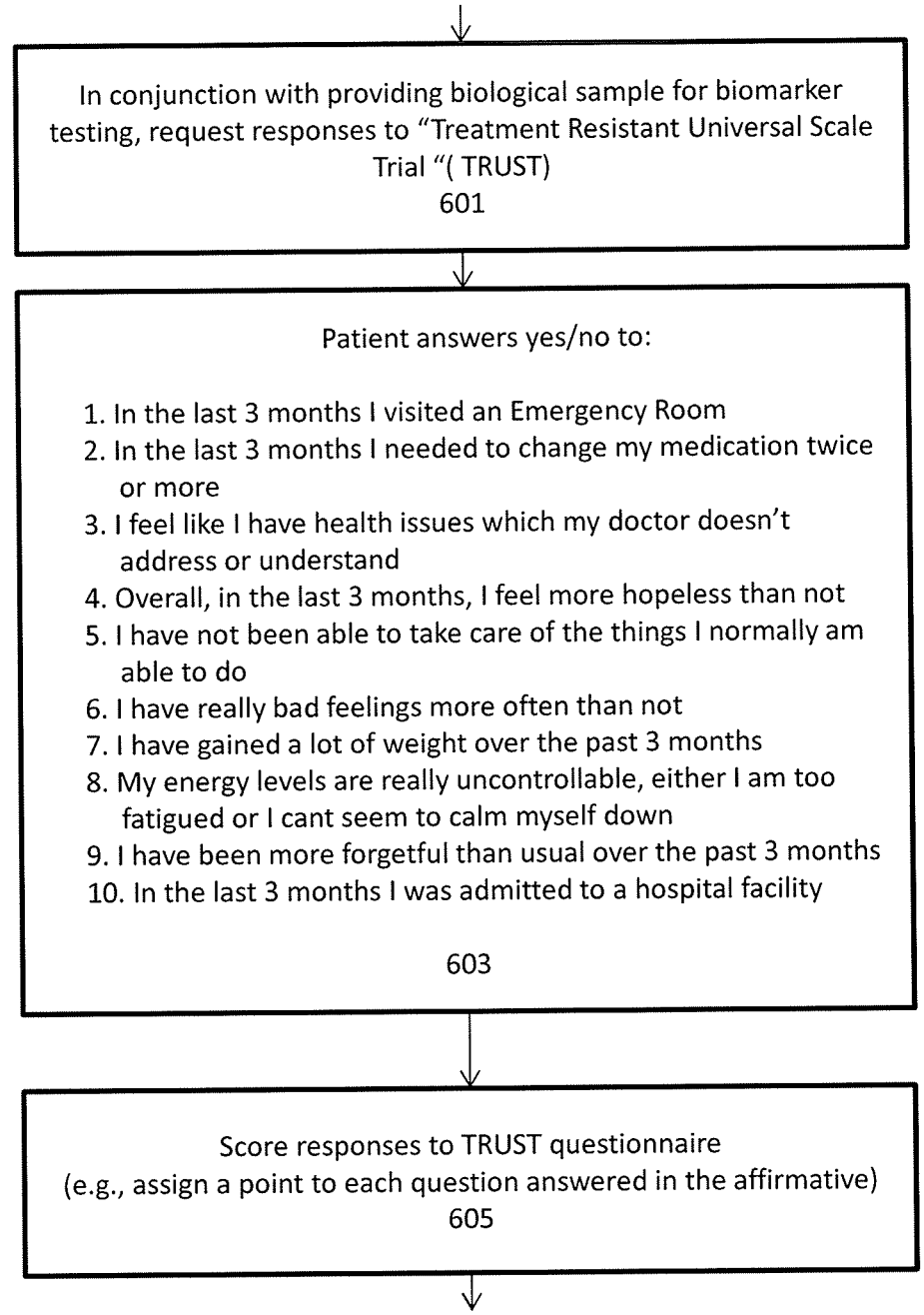
FIG. 6 illustrates the use of a patient questionnaire as part of the methods and/or articles of manufacture described herein.

In general, the methods and reports described herein provide a clear effective means for presenting neuropsychiatric information that is patient-specific and relevant to treatment of neuropsychiatric disorders, particularly but not necessarily exclusive of treatment resistant conditions. By identifying and presenting a specific subset of information that is substantially relevant to the effective understanding and thus treatment of the neuropsychiatric disorder, the systems, methods and articles of manufacture described herein may enhance patient care and simplify treatment. These systems, methods and articles of manufacture may serve as tools to aid the medical professional in predicting patient response to therapies and may also be used to help guide a patient treatment regime.

Generically, the articles of manufacture described may include a report specific to a particular patient, that includes at least one (and preferably more than one) biomarker test result, and interpretive comments describing the physiological significance of the biomarker result. The report may also indicate some index or weighting of the interpretive comments. A scale or metric may be provided to understand the index or weighting. This index or weighting may reflect the confidence of the scientific data supporting the interpretive comments. For example, the index may indicate the number of studies supporting the interpretive comment, the size of the study or studies, and/or the existence of any conflicting data. The interpretive comments may also include one or more visual images representing a brain region effected or implicated by the biomarker being tested or the result of the biomarker tested.

The assays described herein may be referred to as dimensional assays, because they present dimensional, rather than categorical, information. Each dimension of the dimensional assay may describe a particular functional, anatomical and/or neurotransmitter pathway or area. These various areas may be referred to as axes. A dimensional assay may therefore include one or more (and preferably three or four axes). For example, in some variations there are three pharmacodynamic areas or axes of the dimensional assay for assessment of neuropsychiatric disorders: autonomic arousal; executive brain function and emotional valence; and LTP-LTD pathway. These may have parallel critical brain regions and their corresponding neurotransmitter pathways. For example, the executive brain function and emotional valence axis includes the executive region, including the frontal lobes, which are primarily regulated by dopamine, and more specifically by D1 dopamine receptors. The emotional valence region consists primarily of subcortical pathways such as the ventral striatum and the nucleus accumbens, which are also regulated by another subset of dopamine receptors (e.g., D2 receptors) and is involved in emotional valence and reward.

The autonomic arousal axis typically relates to the anterior cingulate cortex with the frontal and subcortical limbic circuitry including the amygdala, which is densely innervated by 5HT1A serotonin receptors and the norepinephrine pathway. In addition, corticotrophin releasing factor, NPY and angiotensin, all play a role in mediating the function of these pathways. The function of this pathway is primarily to modulate and act as an intermediary between internal emotional states, particularly the assessment of threat and their cognitive interpretation.

The LTP pathway involves memory and cognition and relates primarily to the hippocampus. It is involved in cognition, memory, excitatory neurotransmission, and long-term potentiation (LTP). This region of the brain is subserved by glutamate and its relationship to NMDA, kainite and AMPA receptors and their corresponding ionic (sodium, calcium and potassium) channels.

In addition to these three axes, a fourth, pharmacokinetic axis may also be included. The pharmacokinetic axis typically describes various types of metabolic (metabolism) pathways, including the cytochrome P450 mediated hepatic degradation related to pharmacokinetics, methylation, neuroimmune function, blood brain barrier, brain lipid signaling and insulin pathways.

A dimensional assay may include at least one marker from each of these four axes. These biomarkers do not, by themselves, typically indicate a particular diagnosis for a neuropsychiatric disorder (e.g., they are not categorical or "diagnostic" markers), but may cut across different categories of neuropsychiatric disorders. As mentioned, these areas provide dimensional and phenomenological data about inherited predispositions and vulnerability to pathological states, and may thus provide clinical information useful to treat a variety of neuropsychiatric disorders.

Autonomic Arousal Axis

The autonomic hyperarousal axis (or autonomic arousal axis) may include the primarily serotonin neurotransmitter pathways of the anterior cingulate cortex, frontal and subcortical limbic regions (including the amygdala). Recent understandings of the biological bases of depression vulnerability have revealed that both the short allele of the serotonin transporter-linked polymorphic region (5-HTTLPR) and activity in the amygdala are associated with depression. Other studies have reported amygdala hyperactivity associated with the 5-HTTLPR short allele, linking the genetic and neuroimaging lines of research and suggesting a mechanism whereby the short allele confers depression risk. Thus, biomarkers implicated in autonomic hyperarousal and biomarkers implicated in modulation of the noradrenergic (fight/flight) response are included in this axis. For example, any of the following genes may be used as biomarkers for this axis: SERT (biomarkers may include, for example, SNPs or epigenetic regulation of SERT via methylation, protein expression), NPY, and FKBP5. Other biomarkers for the autonomic hyperarousal axis may include HPA axis assessment, such as levels of cortisol, and protein biomarkers that may include norepinephrine metabolites. Angiotensin polymorphisms may also be used as biomarkers. Any of these biomarkers may indicate either an autonomic hyperarousal state; some variations may indicate a hypoarousal state.

In general, any of the genes referred to herein may be referred to by alternative, though established, names, and should be interchangeable, unless otherwise indicated. For example, the SERT gene is also referred to herein as SLC6A4, 5-HTT, 5-HTTLPR, 5HTT, HTT, OCD1, SERT, and hSERT. For simplicity we will herein refer to this gene primarily as the SLC6A4 gene.

Examples of biomarkers for the autonomic hyperarousal axis include the serotonin transporter related genes. Serotonin neurotransmitter transporters are the targets of various therapeutic agents used in the treatment of depression and anxiety. The SSRI mechanism of action in depression is mediated by these agents acting as selective antagonists of the serotonin neurotransmitter transporter. Antagonists block uptake and prolong and/or enhance the action of serotonin.

SSRI agents, drugs most widely used in depression, selectively block the reuptake of serotonin and result in increased serotonin in the synapse.

a. SLC6A4

The serotonin transporter (5-HTT) is a high affinity carrier protein, localized to the plasma membrane of the presynaptic neuron. The role of 5-HTT is to remove serotonin (5-HT) from the synaptic cleft, resulting in serotonin reuptake into the presynaptic terminus. Elevated synaptic serotonin levels are associated with improved mood; thus the effectiveness of many antidepressant drugs (namely selective serotonin reuptake inhibitors, SSRIs) is thought to be due to their inhibition of the serotonin transporter, thereby reducing serotonin reuptake into the presynaptic terminus, and increasing serotonin availability in the synaptic cleft.

The short (S) allele results in less expression of the active transporter protein compared to the long (L) form. As these genetic differences in the 5-HTT affect both baseline serotonin levels and the availability of the transporter as a target for antidepressant therapy, they can affect the efficacy of antidepressant therapy, the likelihood of side effects, and the nature and extent of depressive symptoms experienced. Studies have shown that compared to L/L patients, those homozygous for the short allele (S/S) are more likely to: (a) respond to antidepressant therapy more slowly, (b) experience adverse drug reactions (ADRs) during antidepressant therapy, and (c) develop major depression following adversity due to a poorer stress response.

In general, L/L individuals report a better and faster response to SSRI therapy than S/S patients. While these L/L individuals may demonstrate appropriate response to SSRI therapy in 2 to 4 weeks, individuals with the short allele (L/S or S/S) may respond to SSRI therapy much more slowly or may benefit from non-selective antidepressants.

In addition to serotonin transporters being targets for anti depressant therapy, it is also recognized that assessment of serotonin transporter activity may be a useful biomarker in psychiatry. Various studies have demonstrated that patients with serotonin transporter short alleles are less likely to respond to SSRI therapy and are also more likely to experience treatment emergent side effects. The specific gene which is tested for, referred to as either the 5-HTTLPR or SLC6A4, regulates the rate of serotonin metabolism. This gene controls a receptor located in the synaptic cleft. The receptor binds to serotonin and shuttles it back to the presynaptic neuron, terminating its activity at the post synaptic junction. The binding affinity of this receptor (referred to as SERT) is regulated by hereditary factors related to the length of an allele. Short alleles have reduced binding affinity effects on the serotonin transporter. Conversely, long alleles have better affinity, resulting in a more efficient reuptake process. Thus, the inherited short allele of the serotonin transporter results in more synaptic serotonin and the inherited long allele leads to reduced serotonin in the synapse.

Example of interpretive language in the report for individuals who express short alleles of the serotonin receptor may include: "properties of the short or 'S' allele have been associated with decreased transcription of the serotonin transporter and increased vulnerability to major depression and PTSD in the presence of stressors. Subjects homozygous for the s-allele with a significant history of stressful life events exhibit elevated cortisol secretions in response to stress show greater activation in stress-related brain regions such as the hypothalamus and amygdala and may be at higher risk of stress related disorders such as PTSD. Medical interventions which address heightened physiological arousal in association with serotonin transporter variants should be considered. Noradrenergic agents which demonstrate both an anti anxiety and anti depressive effect may be considered for these individuals. Potential agents which can be regarded may include Mirtazepine, Angiotensin receptor blockers, Lithium, Venlafaxine and Tianeptine."

b. FKBP5

FKBP5 regulates the cortisol-binding affinity and nuclear translocation of the glucocorticoid receptor. FKBP5 is a glucocorticoid receptor-regulating co-chaperone of hsp-90 and plays a role in the regulation of the hypothalamic-pituitary-adrenal system and the pathophysiology of depression.

FK506 regulates glucocorticoid receptor (GR) sensitivity. When it is bound to the FKBP5 receptor complex, cortisol binds with lower affinity and nuclear translocation of the receptor is less efficient. FKBP5 expression is induced by glucocorticoid receptor activation, which provides an ultra-short feedback loop for GR-sensitivity.

Changes in the hypothalamic pituitary adrenal (HPA) system are characteristic of depression. Because the effects of glucocorticoids are mediated by the glucocorticoid receptor (GR), and GR function is impaired in major depression, due to reduced GR-mediated negative feedback on the HPA axis. Antidepressants have direct effects on the GR, leading to enhanced GR function and increased GR expression.

Polymorphisms the gene encoding this co-chaperone have been shown to associate with differential up-regulation of FKBP5 following GR activation and differences in GR sensitivity and stress hormone system regulation. Alleles associated with enhanced expression of FKBP5 following GR activation, lead to an increased GR resistance and decreased efficiency of the negative feedback of the stress hormone axis. This results in a prolongation of stress hormone system activation following exposure to stress. This dysregulated stress response might be a risk factor for stress-related psychiatric disorders.

Various studies have identified single nucleotide polymorphisms (SNPs) in the FKBP5 gene associated with response to antidepressants, and one study found an association with diagnosis of depression. Polymorphisms at the FKBP5 locus have also been associated with increased recurrence risk of depressive episodes.

In fact, the same alleles are over-represented in individuals with major depression, bipolar disorder and post-traumatic stress disorder.

Individuals homozygous for the T/T genotype at one of the markers (rs1360780) reported more depressive episodes and responded better to antidepressant treatment.

For example, Lithium may be a preferred genotype based intervention for individuals with phenomenological evidence of autonomic dysfunction who express clinically relevant variants in the serotonin transporter or FKBP5 gene c. 5HT1A Quantitative genetic studies have found considerable variability in the activity of the hypothalamus pituitary adrenal (HPA) axis in response to stress. The HPA axis is regulated by a neuronal network including the amygdala, which is influenced by the effects of the −1019 G/C polymorphism in the 5HT1A (HTR1A) gene. Reduction in postsynaptic 5-HT1A receptor binding in the amygdala is correlated with untreated panic disorder. Several single nucleotide polymorphisms have been described for 5-HT1A receptor gene. The HTR1A C(−1019)G polymorphism is located in a transcriptional regulatory region and G allele and/or G/G of HTR1A C(−1019)G polymorphism genotype was found to be associated with major depression, anxiety and suicide risk.

d. NPY

Anxiety is integrated in the amygdaloid nuclei and involves the interplay of the amygdala and various other areas of the brain. Neuropeptides play a critical role in regulating this process. Neuropeptide Y (NPY), a 36 amino acid peptide, is highly expressed in the amygdala. It exerts potent anxiolytic effects through cognate postsynaptic Y1 receptors, but augments anxiety through presynaptic Y2 receptors.

The activity of NPY is likely mediated by the presynaptic inhibition of GABA and/or NPY release from interneurons and/or efferent projection neurons of the basolateral and central amygdala. A less active NPY rs16147-399C allele conferred slow response after 2 weeks and failure to achieve remission after four weeks of treatment. The rs16147 C allele was further associated with stronger bilateral amygdala activation in response to threatening faces in an allele-dose fashion.

Emotional Valence, Attention, Reward and Executive Brain Axis

The executive brain function and the emotional valence and reward systems are combined into a single axis, though in some variations they may be separated out into two axes. This axis is generally concerned with regulation of cortical/frontal lobe and limbic and subcortical (e.g. ventral striatal and nucleus accumbens) dopamine systems. Biomarkers may include: COMT (e.g. SNPs); sigma receptor (e.g. polymorphisms), Dopamine transporter genes (e.g. SLC6A3), and methylation genes (e.g. MTHFR). The methylation genes appear to be in epistasis with COMT in such a fashion that low methylation states may reduce dopamine by disinhibiting COMT degradation of catecholamines. These biomarkers may be thought of as markers for working memory, executive brain function and attentional processes.

DNA methylation is associated with gene silencing, stress, and memory. The catechol-O-methyltransferase (COMT) Val (158) allele in rs4680 (G allele) is associated with differential enzyme activity, stress responsivity, and prefrontal activity during working memory (WM). Methylation of the Val(158) allele measured from peripheral tissue is associated negatively with lifetime stress; it interacts with stress to modulate prefrontal activity during WM, such that greater stress and lower methylation are related to reduced cortical efficiency, suggests that stress-related methylation is associated with silencing of the gene, which partially compensates the physiological role of the high-activity Val allele in prefrontal cognition and activity.

Limbic and/or subcortical dopamine regulation is also included in this axis, and biomarkers for this activity may include: DRD2/ANKK1 (e.g., TaqI A polymorphism (rs1799732), which has been suggested to be involved in reward-related psychiatric disorders). Mesolimbic dopaminergic pathways are modulated by the kinase domain containing 1 (ANKK1) gene (e.g., a biomarker may include the DRD2 Taq Ia/ANKK1 SNPs) which regulate novelty seeking and harm avoidance through dopaminergic mesolimbic pathways. These pathways are is associated with a relatively low D(2) receptor density in the striatum. Additional biomarkers implicated in regulation of limbic and/or subcortical dopamine may include DRD2 genes and the like.

a. COMT

COMT is an enzyme involved in the degradation of dopamine, predominantly in the frontal cortex. Several polymorphisms in the COMT gene have been associated with poor cognition, diminished working memory, and increased anxiety as a consequence of altered dopamine catabolism. Suitable COMT gene polymorphisms include the functional common polymorphism (Val(158)Met; rs4680) that affects prefrontal function and working memory capacity and has also been associated with anxiety and emotional dysregulation.

The COMT rs4680 G/G genotype (Val/Val homozygous genotype) confers a significant risk of worse response after 4-6 weeks of antidepressant treatment in patients with major depression. There is a negative influence of the higher activity COMT rs4680rs4680 G/G genotype on antidepressant treatment response during the first 6 weeks of pharmacological treatment in major depression, possibly conferred by decreased dopamine availability. This finding suggests a potentially beneficial effect of interventions such as transcranial magnetic stimulation, which has been shown to increase metabolic activity in the dorsolateral prefrontal cortex in a genotype specific manner. Conversely, COMT Met/Met variants may have an opposite phenotype and cluster of symptoms including increased vulnerability to addiction. Treatments which could potentially address these variants include S-adenosyl methionine (a COMT agonist which may lower prefrontal dopamine) or a dopamine antagonist.

Suggested language of results of COMT variants may include the following:

"The functional Val158Met polymorphism in the gene coding for the catechol-O-methyltransferase (COMT), the major enzyme degrading the neurotransmitters dopamine and norepinephrine, has been associated with differential reactivity in the limbic and prefrontal brain regions and may contribute to individual differences in reward-seeking behavior and in predisposition to neuropsychiatric disorders."

"Individual differences in dopamine mediated ventral striatal activity may relate to disruptions in hedonic state and motivation seen in some forms of depression related to lower dopamine signaling in these individuals."

"Medical interventions, such as Transcranial magnetic stimulation, which address reduced dorsolateral prefrontal cortex activity may be considered in individuals with COMT polymorphisms b. DRD2

Several lines of evidence suggest that antipsychotic drug efficacy is mediated by dopamine type 2 (D(2)) receptor blockade. Six studies reported results for the −141C Ins/Del polymorphism (rs1799732) which indicated that the Del allele carrier is significantly associated with poorer antipsychotic drug response relative to the Ins/Ins genotype. These findings suggest that variation in the D(2) receptor gene can, in part, explain variation in the timing of clinical response to antipsychotics and higher risk of weight gain in deletion allele subtypes of the DRD2 gene.

Suggested language in an interpretive report may include the following:

"Abnormalities in the binding potential of the dopamine D(2) receptor have been associated with psychiatric disorders including schizophrenia, autism and OCD. DRD2 receptors are expressed in the orbital cortex and caudate nucleus, regions of the brain associated with perseverative cognitive and emotional responses in depression studies have demonstrated lower density of dopamine D2 receptor (DRD2) in subjects without the Del alleles of the −141C Ins/Del polymorphism in DRD2 gene promoter region than in those with one or two of the Del alleles. Patients without the Del allele demonstrate a higher percentage of improvement in anxiety-depression symptoms than those with the Del allele after treatment with dopamine antagonists, but prospective clinical trials are required to firmly establish this relationship."

"Medical interventions which address imbalances of dopamine binding to the DRD2 receptor in the caudate and orbital cortex should be considered in individuals with DRD2 variants."

"This patient exhibits a variant of the dopamine D2 receptor gene associated with reduced D2 receptor binding and inhibitory capacity. Clinically, individuals with this variant have been associated with reduced anti-psychotic efficacy and higher rates of antipsychotic-induced metabolic syndrome."

Synaptic Mediated LTP-LTD Axis

Disruptions in long term potentiation leading to over-facilitation of abnormal synaptic pathways may indicate proneness to paroxysmal disturbances, irritability, instability, neurodegenerative vulnerability and the like. This axis may be probed with biomarkers to the glutamatergic pathway (e.g., NMDA and AMPA receptors) as well as calcium, potassium and sodium ion channels. For example, CACNA1C is thought to be important in modifying the effects of: synaptic activity on cell survival, synaptic plasticity, MAPK pathway activation and critical pathways involved in learning and memory. Intracellular calcium levels are regulated specifically by CACNA1C which play a role in learning and memory via mediating the downstream effects of glutamate neurotransmission. CACNA1C mRNA levels increase following repeated amphetamine administration, and CACNA1C may be elevated in postmortem brains from BP patients.

Preclinical and clinical studies support a role for CACNA1C in mood disorder pathophysiology, treatment resistance, autism and schizophrenia. Biomarkers implicated in regulation of glutamate may include calcium channel SNPs (e.g., rs2370419, rs1006736). The presence of these biomarkers may suggest that treatment with a calcium channel antagonist may be therapeutic in such patients. Other biomarkers may include sodium channel SNPs, whose presence may suggest treatment with sodium channel antagonist may be indicated. Other genes that may be tested as biomarkers include: ANK3 (rs10994336), and BDNF (Val66Met).

Examples of biomarkers and interpretive text in the LTP axis include:

a. CACNA1C

The calcium ion is one of the most versatile, ancient, and universal of biological signaling molecules, known to regulate physiological systems at every level from membrane potential and ion transporters to kinases and transcription factors. Disruptions of intracellular calcium homeostasis underlie a host of emerging diseases, the calciumopathies. Cytosolic calcium signals originate either as extracellular calcium enters through plasma membrane ion channels or from the release of an intracellular store in the endoplasmic reticulum (ER) via inositol triphosphate receptor and ryanodine receptor channels. Therefore, to a large extent, calciumopathies represent a subset of the channelopathies, but include regulatory pathways and the mitochondria, the major intracellular calcium repository that dynamically participates with the ER stores in calcium signaling, thereby integrating cellular energy metabolism into these pathways, a process of emerging importance in the analysis of the neurodegenerative and neuropsychiatric diseases.

Molecular genetic analysis offers opportunities to advance our understanding of the nosological relationship between psychiatric diagnostic categories in general and the mood and psychotic disorders in particular. The CACNA1C gene encodes one subunit of a calcium channel. Results suggest that ion channelopathies may be involved in the pathogenesis of bipolar disorder, schizophrenia and autism with an overlap in their pathogenesis based upon disturbances in brain calcium channels.

CACNA1C encodes for the voltage-dependent calcium channel L-type, alpha 1c subunit. Gene variants in CACNA1 (e.g. rs1006737) are associated with altered calcium gating and excessive neuronal depolarization. CACNA1 polymorphisms have been associated with increased risk of bipolar disease and schizophrenia.

Psychiatric disease phenotypes, such as schizophrenia, bipolar disease, recurrent depression and autism, produce a constitutionally hyperexcitable neuronal state that is susceptible to periodic decompensations. The gene families and genetic lesions underlying these disorders may converge on CACNA1C, which encodes the voltage gated calcium channel.

These findings suggest some degree of overlap in the biological underpinnings of susceptibility to mental illness across the clinical spectrum of mood and psychotic disorders, and show that at least some loci can have a relatively general effect on susceptibility to diagnostic categories based upon alterations in calcium signaling. Abnormalities in synaptic pathways can also be probed by specific brain imaging modalities which probe the integrity of axons and white matter. For instance, diffusion tensor imaging demonstrated decreased white matter integrity, indicated by lower fractional anisotropy and longitudinal diffusivity, in the ANK3 rs10994336 risk genotype in the anterior limb of the internal capsule and carriers of the A allele of the CACNA1C gene showed significantly increased gray matter volume and reduced functional connectivity within a corticolimbic frontotemporal regions, supporting the effects of the rs1006737 on frontotemporal networks, This suggests that influence of CACNA1C variation on corticolimbic functional connectivity.

Medical interventions which address heightened neuronal depolarization in the hippocampus in association with calcium channel variants should be considered.

Agents which modulate or exert effects on calcium channels may be preferred agents to use in patients with psychiatric disorders in patients who exhibit these variants, as will be further described in subsequent paragraphs. Such agents may include specific L-type voltage-gated calcium channel inhibitors such as Nimodipine, Flunarizine and the like. They may also include other mood stabilizers, such as Lithium or Valproic acid.

b. ANK3

Another biomarker includes the ANK3 gene (e.g. rs10994336). Genetic variants in ankyrin 3 (ANK3) have recently been shown to be associated with bipolar disorder and schizophrenia. The gene ANK3 encodes ankyrin-G, a large protein whose neural-specific isoforms, localized at the axonal initial segment and nodes of Ranvier, may help maintain ion channels and cell adhesion molecules. ANK3 is essential for both normal clustering of voltage-gated sodium channels at axon initial segments. Personalized treatments for individuals with this variant may include sodium channel modulating agents, such as Lamotrigine.

In patients with sodium channel gene variants, there may be altered expression of depolarization across the axon which is effecting normal neural conduction. This may provide a model of how the oscillation between long term depression and potentiation becomes abnormal (e.g., an imbalance between LTP and LTD). The sodium channels may then dis-regulate the sodium channels. This bipolar model is represents dis-regulation between LTP and LTD, and may result from the sodium channel variation. In patients with oscillatory affective states secondary to normal axonal propagation, sodium channel blockers may be recommended. Lamotrigine (or other sodium channel blocking drugs) may be used if there is a polymorphism in the ANK3 gene.

c. BDNF

Brain-derived neurotrophic factor is a member of the nerve growth factor family. It is induced by cortical neurons and is necessary neurogenesis and neuronal plasticity. BDNF has been shown to mediate the effects of repeated stress exposure and long term antidepressant treatment on neurogenesis and neuronal survival within the hippocampus. The BDNF Val66Met variant is associated with hippocampal dysfunction, anxiety, and depressive traits. Previous genetic work has identified a potential association between a Val66Met polymorphism in the BDNF gene and bipolar disorder. Meta-analysis based on all original published association studies between the Val66Met polymorphism and bipolar disorder up to May 2007 shows modest but statistically significant evidence for the association between the Val66Met polymorphism and bipolar disorder from 14 studies consisting of 4248 cases, 7080 control subjects and 858 nuclear families.

The BDNF gene may play a role in the regulation of stress response and in the biology of depression and the expression of brain-derived neurotrophic factor (BDNF) may be a downstream target of various antidepressants.

Exposure to stress causes dysfunctions in circuits connecting hippocampus and prefrontal cortex. BDNF is down-regulated after stress. Acute treatment with the antidepressant tianeptine reverses stress-induced down-regulation of BDNF. Tianeptine increases the phosphorylation of Ser831-GluA1. Psychological stress down-regulates a putative BDNF signaling cascade in the frontal cortex in a manner that is reversible by the antidepressant tianeptine. Thus agents which promote BDNF are novel mechanisms to treat stress induced alterations in the limbic system Activation of AMPA receptors by agonists is thought to lead to a conformational change in the receptor causing rapid opening of the ion channel, which stimulates the phosphorylation of CAMK11/PKC sites and subsequently enhance BDNF expression.

A structural class of AMPA receptor positive modulators derived from aniracetam are called Ampakines. Aniracetam and Nefiracetam are neurological agents called 'racetams' that are analogs of piracetam. They are regarded as AMPA receptor potentiators and CaMKII agonists.

Small molecules that potentiate AMPA receptor show promise in the treatment of depression, a mechanism which also appears to be mediated by promoting BDNF via CaMKII pathways. Depression is associated with abnormal neuronal plasticity. AMPA receptors mediate transmission and plasticity at excitatory synapses in a manner which is positively regulated by phosphorylation at Ser831-GluR1, a CaMKII/PKC site.

Aniracetam [1-(4-methoxybenzoyl)-2-pyrrolidinone] is an AMPA receptor potentiator that preferentially slows AMPA receptor deactivation. AMPA receptor potentiators (ARPs), including aniracetam, exhibit antidepressant-like activity in preclinical tests. Unlike most currently used antidepressants, interactions of aniracetam with proteins implicated in AMPA receptor trafficking and with scaffolding proteins appear to account for the enhanced membrane expression of AMPA receptors in the hippocampus after antidepressant treatment. The signal transduction and molecular mechanisms underlying alpha-amino-3-hydroxy-5-methyl-4-isoxazole propionate (AMPA)-mediated neuroprotection evokes an accumulation of BDNF and enhance TrkB-tyrosine phosphorylation following the release of BDNF. AMPA also activate the downstream target of the phosphatidylinositol 3-kinase (PI3-K) pathway, Akt. The increase in BDNF gene expression appeared to be the downstream target of the PI3-K-dependent by AMPA agonists and Tianeptine (described below). Thus, AMPA receptors protect neurons through a mechanism involving BDNF release, TrkB receptor activation, and up-regulation of CaMKII which increase BDNF expression.

Olfactory bulbectomized (OBX) mice exhibit depressive-like behaviors. Chronic administration (1 mg/kg/day) of nefiracetam, a prototype cognitive enhancer, significantly improves depressive-like behaviors. Decreased calcium/calmoculin-dependent protein kinase II mediates the impairment of hippocampal long-term potentiation in the olfactory bulbectomized mice. Nefiracetam treatment (1 mg/kg/day) significantly elevated CaMKII in the amygdala, prefrontal cortex and hippocampal CA1 regions. Thus, CaMKII, activation mediated by nefiracetam treatment elicits an anti-depressive and cognition-enhancing outcome.

d. SCN1A

A polymorphism within SCN1A (encoding the 1 subunit of the type I voltage-gated sodium channel) has been replicated in three independent populations of 1699 individuals. Functional magnetic resonance imaging during working memory task detected SCN1A allele-dependent activation differences in brain regions typically involved in working memory processes. These results suggest an important role for SCN1A in human short-term memory.

Voltage-gated sodium channels have an important role in the generation and propagation of the action potential and consist of an alpha subunit, which forms the ion conduction pore, and two auxiliary beta subunits. The alpha subunit has four homologous domains and different genes (SCN1A through SCN11A) encode different alpha subunits named Nav1.1 through Nav1.9 The SCN1A is expressed in brain regions critical for memory formation, regulates excitability of neuronal membranes and several SCN1A mutations are known to cause a variety of neurological diseases such as familial hemiplegic migraine. Some antiepileptic drugs, such as phenyloin and carbamazepine, bind to voltage-gated sodium channels and genetic variability within SCN1A may predict the response to carbamazepine and phenyloin in patients diagnosed with epilepsy.

Lamotrigine, another antiepileptic drug that binds to voltage-gated sodium channels, is an effective maintenance treatment for bipolar disorder, particularly for prophylaxis of depression, a mental disorder with commonly observed working memory deficits. A recent fMRI study reports that lamotrigine treatment in depressed patients results in increased activation of brain regions typically involved in working memory processes.

Heterozygous individuals of the SCN1A gene (rs10930201) showed significantly increased brain activations compared with homozygous A allele carriers in the right superior frontal gyrus/sulcus, indicating a potential biomarker for Lamotrigine in these individuals with mood disorder.

Drug Metabolism

Biomarkers implicated in drug metabolism may include: CYP2D6, CYP2C19, CYP3A4, ABCB1, MTHFR and 5HT2C. For example, methylation related genes may be biomarkers in this axis.

a. MTHFR

The 5,10-methylenetetrahydrofolate reductase (MTHFR) is a key enzyme for intracellular folate homeostasis and metabolism. Methylfolic acid, synthesized from folate by the enzyme MTHFR, is required for multiple biochemical effects in the brain. A primary role involves the synthesis of dopamine in the brain. Folic acid deficiency results in fatigue, reduced energy and depression. Low folate blood levels are correlated with depression and polymorphisms of the MTHFR gene (e.g. rs1801133) are closely associated with risk of depression.

MTHFR irreversibly reduces 5-Methyltetrahydrofolate which is used to convert homocysteine to methionine by the enzyme methione synthetase. The C677T SNP of MTHFR (rs1801133) has been associated with increased vulnerability to several conditions and symptoms including depression.

The nucleotide 677 polymorphism in the MTHFR gene has two possibilities on each copy of chromosome 1: C or T. 677C (leading to an alanine at amino acid 222); 677T (leading to a valine substitution at amino acid 222) encodes a thermolabile enzyme with reduced activity. The degree of enzyme thermolability (assessed as residual activity after heat inactivation) is much greater in T/T individuals (18-22%) compared with C/T (56%) and C/C (66-67%).

MTHFR gene polymorphisms include polymorphisms in the 5,10-methylenetetrahydrofolate reductase (MTHFR) gene, including MTHFR C677T and its association with common psychiatric symptoms including fatigue and depressed mood. These symptoms are proposed to be due to hypomethylation of enzymes which breakdown dopamine through the COMT pathway. In this model, COMT is disinhibited due to low methylation status, resulting in increased dopamine breakdown.

For unipolar depression, the MTHFR C677T polymorphism has been well described and validated.

A recommendation to prescribe various folic acid modulating agents, particularly in individuals with MTHFR polymorphisms, may be part of the interpretive language of our report. Other markers of metabolism, including an analysis of gene polymorphisms associated with hepatic metabolism of psychotropic drugs, have previously been disclosed.

In some variations, the methods and articles of manufacture described herein may be used to diagnose (using the dimensional based assay) a patient by incorporating specific axes of brain dysfunction, including those which are associated with genes of metabolism. For example, developmentally-based neuropsychiatric disorders such as autism and schizophrenia may be difficult to diagnose early and difficult to treat. However, there is a strong motivation to diagnose early, at preclinical or prodromal stages, since early intervention may blunt, reduce or even prevent the full expression of these disorders. The dimensional nature of the neuropsychological methods and articles of manufacture described herein may allow for early (e.g., prodromal) detection of such disorders.

The absence of operational hallmarks of clinical validity has slowed the development of a treatment research evidence base that could benefit these impaired, symptomatic, at-risk patients and their families. Prodromal diagnosis can be refined based upon the method described herein. For example, several studies have suggested alterations in the activities of antioxidant enzymes such as glutathione peroxidase in neurodevelopmentally-associated disorders, such as autism and schizophrenia. Polymorphisms of genes involved in glutathione metabolism, e.g. GSTP1 and GSTM1 are reportedly associated with autistic disorder. GPX1 GCG repeat, genes which mediate endogenous anti-oxidant pathways, have been reported in autism. Genetic studies have shown an association between schizophrenia and a GAG trinucleotide repeat (TNR) polymorphism in the catalytic subunit (GCLC) of the glutamate cysteine ligase (GCL), the key enzyme for glutathione (GSH) synthesis.

The glutathione deficit associated with these polymorphisms may modulate dopamine receptor function, from enhanced responses in control neurons (likely via D1-type receptors) to decreased responses in low-glutathione neurons (via D2-type receptors). This represents a mechanism by which dopaminergic systems could be dysfunctional under conditions of impaired glutathione synthesis as in schizophrenia and autism.

Many genes associated with schizophrenia and autism code for proteins associated with neurodevelopmentally related processes. These include NRG1 as perturbations in neuregulin-1 (NRG1)/ErbB4 function have been associated with schizophrenia. Recent evidence also suggests that NRG1 may play a role in inflammation and immune system response in the brain. Schizophrenia-associated miss-sense mutations within the transmembrane region of NRG1 may be linked to immune dysregulation as In vivo, increased levels of autoimmune markers as well as elevated levels of cytokines have been significantly associated with the NRG1 mutation.

The methods and articles of manufacture described herein may also be used to provide customized guidance for non-traditional therapeutics such as medical foods and herbal remedies. Alternative and non-conventional practices of medicine may include the use of such therapies (particularly in psychiatry), and it would be beneficial to include interpretive information on such non-traditional therapeutics. For example, many clinicians and patients use botanicals to address mental health concerns, and many of these herbs influence cytochrome p450 enzyme activity. For instance, St Johns wort, used as a natural antidepressant increases the risk of herb-drug interactions. St Johns wort inhibits 2D6 and 3A4, which may alter the PK of certain drugs also metabolized by these pathways. Clinically, as many drugs have narrow therapeutic indices, gene analysis becomes imperative to avoid dangerous interactions. Thus, the use of the algorithms and methods described herein to include herb-drug and herb-gene interactions is particularly relevant to the field of neuropsychiatry and represents a previously unrealized clinical need.

Imaging Biomarkers

As mentioned above, biomarkers may not be limited to genetic markers, but may include methylation, protein expression, imaging biomarkers, and the like. For example, Diffusion Tensor Imaging (DTI) is a magnetic resonance (MR) imaging technique applied to evaluate water diffusion in axons (e.g., fractional anistropy or FA) in the brain as a measure of white matter integrity and tract directionality. Decreases in FA have been observed in association with axonal injury. DTI can be used to support the dimensional axis approach taught herein in a manner similar to the functional consequences of abnormal gene expression. For instance, the autonomic arousal axis may be examined using DTI as a biomarker.

Disruption of fronto-temporal connections involving the arcuate fasciculus (AF), a limbic associated white matter pathway which may underlie language processing anomalies and psychotic features such as auditory hallucinations in schizophrenia. Large deformation diffeomorphic metric mapping and Fiber Assignment Continuous Tracking can be employed in patients with schizophrenia with expected higher left FA in the temporal segment of AF, positive psychotic symptoms such as delusions and hallucinations in patients with schizophrenia, suggesting aberrant fronto-temporal connectivity in schizophrenia and other psychotic states. This example supports the dimensional axis model this patent puts forward, such that objective biomarkers used to assess heightened or abnormal limbic activity can be used clinically. Thus, thee limbic axis (the autonomic arousal system) may be assessed as mentioned above, the subcortical axis or other regionally associated functional brain circuitry may also be examined.

For example the LTP-LTD axis may also be examined using DTI. In depressive disorders and bipolar states, in which the LTP-LTD balance is disrupted, the expected changes in FA are more likely to be detected in subcortical brain regions, such as the internal capsule the internal capsule is commonly reported to have significantly reduced fractional anisotropy, especially both in depression and after closed head injury, which agrees with deep brain stimulation studies and may suggest a useful biomarker particularly to use or monitor techniques such as TMS, VNS or DBS.

Additional applications for FA assessments could be used to monitor the neuroprotective actions of a drug for a condition such as Alzheimers. For instance, FA decline is preserved in the posterior body of the corpus callosum in Alzheimers patients treated with Galanthamine compared to placebo.

Thus, in some variations, a multivariate source-based morphometry (SBM) method for processing fractional anisotropy (FA) data which utilizes independent component analysis (ICA) and decomposes an FA image into spatial maps and loading coefficients may be used to provide additional biomarkers in one or more of the axes described herein.

Example 1

Treatment Resistant Disorders (TRD)

In some variations, the articles of manufacture described herein are generally reports including information of patient-specific biomarkers that is relevant to pharmacologic intervention and treatment of treatment resistant disorders (TRD) in neuropsychiatry, regardless of a particular categorical diagnosis. The inventor has identified a small sub-set of biomarkers that may be important for understanding the best way to treat psychiatric treatment resistance. This subset of biomarkers may be selected from the four axes discussed above (including the three pharmacodynamic axes and the pharmacokinetic axis), and may represent a subset of biomarkers representing these axes. A patient's genotype for all, or a major subset, of these six members of this TRD epistatic group (e.g., five of the six, four of the six, three of the six) may provide sufficient information to a medical practitioner to accurately guide treatment. Although information about other genetic loci may be helpful, these six members may be of enhanced importance because they (alone and in combination) offer insight into the patient's specific drug response to TRD. By identifying the specific subset of genes related to the neurochemical imbalance involved in treatment resistance, the treatment choice may be intelligently applied based on the genotype of these genes.

In the reports and methods described herein, the six core members of the TRD include the six genetic loci (forming a core epistatic group) from across the different axes described above: variants of SLC6A4 (variants of a single-nucleotide polymorphism of Serotonin Transporter); MTHFR (variants in methylenetetrahydrofolate reductase); COMT (variants in Catechol-O-Methyl Transferase); DRD2 (variants of Dopamine receptor D2); CACNA1C (variants of L-type voltage-gated calcium channel); ANK3 (variants of ankyrin 3), HTR2C (5-hydroxytryptamine (serotonin) receptor 2C), CYP2D6, CYP2C19, CYP3A4 (variants of cytochrome P450). In this example, members of this core group are relevant in part because they indicate a possible therapeutic decision. Genes present on the report are those that are relevant to patient treatment outcome, including the avoidance of side effects, increasing effectiveness of drug therapies, or the like. Drugs such as psychotropic agents are of particular interest, and the accompanying interpretive comments (if included) may be related to the influence of one or more of the core epistatic group on such drugs.

As mentioned above, the application Ser. No. 12/790,262 previously incorporated by reference illustrates how single nucleotide polymorphisms (SNPs) in certain genes may be related to subtypes of depression. In this model, certain antidepressants and other psychotropic agents may mediate their effects via inhibition of CaMKII. Such agents may reduce cortical excitability. The decision to employ this class of agents can be assisted by an analysis of gene polymorphisms which are thought to be associated with up-regulation of CaMKII.

The multiple functional and neuroanatomical model described above (including the autonomic arousal axis, the emotional valence and reward and executive brain function axis, and the memory and cognition axis and/or the metabolic axis) may be simplified into a excitatory/inhibitory model of CaMKII. Neuropsychiatric disorders may be characterized by an imbalance between excitatory and inhibitory systems at the level of neuronal cellular activity. In this manner, focal brain dysfunctionality may be related to either the hypo- or hyper-functionality secondary to excessive inhibitory or excitatory mechanisms. Some neuropsychiatric disorders may arise because of these discrete excitatory/inhibitory imbalances. For example, frontal lobe effects of a COMT Val/Val polymorphism, discussed above, may result in hyperfunctional activity resulting in reduced working memory. Changes in the excitatory and inhibitory modulation may be viewed through the filter of the CaMKII activity model previously described. Thus, patients with neuropsychiatric disorders may be characterized by an imbalance between excitatory and inhibitory neurotransmission mediated by CaMKII. In one subtype, the target of a therapeutic requires activation, not inhibition, of CaMKII. The identification of these individuals can be determined by an analysis of a second, distinct subset of genes which results in reduced CaMKII activity. Subsequently, psychotropic agents which activate CaMKII are preferentially indicated. Thus, described therein are methods, devices and systems (e.g., assays) for determining if a patient has one or more genomic variations effecting the expression of genes that either reduce, or increase, the activity or expression of genes that ultimately modulate the activity of CaMKII. Further, also described in the application Ser. No. 12/790,262 are methods, devices and systems for providing treatment guidance based on the identification of one or more of these variants.

As mentioned, CaMKII is markedly enriched at synapses, where it is involved in the control of synaptic transmission, transmitter release and synaptic plasticity. Alterations of the activity of CaMKII may form the basis of gene, environment and drug related effects on behavioral states.

Communication between cell surface proteins and the nucleus may be integral to many cellular adaptations. In the case of ion channels in excitable cells, the dynamics of signaling to the nucleus are particularly important because the natural stimulus, surface membrane depolarization, is rapidly pulsatile. CaMKII acting near the ion channel couples local calcium ions which then gives rise to signal transduction, encodes the frequency of calcium ion channel openings, and amplifies molecular signals in the brain.

Calcineurin is a calmodulin (CaM) dependent protein phosphatase recently found to be altered in the brains of patients suffering from schizophrenia and by patients exposed to repeated antipsychotic treatment. Repeated treatment with haloperidol, clozapine or risperidone decreases CaMKIIalpha, whereas increases in this protein were observed in an amphetamine model of the positive symptoms of schizophrenia.

Lithium is widely used in the treatment of bipolar disorder, although its mechanism of action is not fully clear. Lithium down-regulates CaMKIV (enzymatic activity, phospho-Thr196 and protein expression level) in the hippocampus, indicating the involvement of CaMKIV in the mechanism of action of lithium.

Intracellular calcium influx through NMDA receptors triggers a cascade of deleterious signaling events which lead to neuronal death. Inhibitors of calcium ions and/or calmodulin-dependent protein kinase II (CaMKII) prevent the occurrence of apoptosis, suggesting a role for CaMKII in NMDA mediated cell death. These examples are meant to provide instruction on a genetic basis of analysis whether excitatory or inhibitory brain pathways need to be targeted by select psychopharmacological interventions.

This observation thus discloses a new putative site of action and classification of psychotropic drugs, as well as a previously undisclosed explanation on how SNPs, indels, CNVs, STRs, VNTRs, etc. . . . and other variants in various genes are related to subtypes of depression. In this model, certain antidepressants and other psychotropic agents mediate their effects via inhibition of CaMKII. These agents reduce cortical excitability. The decision to employ this class of agents can be assisted by an analysis of gene polymorphisms which are associated with up-regulation of CaMKII.

However, a separate and phenotypically distinct group of patients with neuropsychiatric disorders are characterized by an imbalance in inhibitory neurotransmission. In this subtype, the target of a therapeutic requires activation, not inhibition, of CaMKII. The identification of these individuals can be determined by an analysis of a second, distinct subset of genes which results in reduced CaMKII activity. Subsequently, psychotropic agents which activate CaMKII are preferentially indicated.

Specific interventions based upon these gene clusters are also claimed. These treatments promote inhibitory mechanisms in the CNS based upon their specific effects on the abnormal expression of these genes. These agents may include CaMKIV antagonists.

For example, described in the application Ser. No. 12/790,262 are panel assays to determine the presence of SNPs that up-regulate or inhibit CaMKII activity.

The panel assay may also include an interpretive comment indicating the effect of any identified SNPs on the regulation of CaMKII activity. In some variations, the panel assay includes an interpretive comment suggesting a treatment based on identified SNPs.

In general, a SNP indicator indicates the presence or absence of a SNP within a specific tissue sample. The SNP indicator may be based as a screening test, such as a genetic screen (e.g., using a PCR-based test) to determine if the SNP is present within the DNA of a particular patient's tissue sample being examined. Any appropriate test for the individual SNP, or a pooled test for multiple SNPs, may be used as part of the methods, kits, assays and systems. As mentioned, the SNP indicators may comprise one or more PCR-based assays. A SNP indicator may be included a report (e.g., visual, oral, printed, electronic, or the like), and may indicate the presence or absence of the particular SNP. The SNP indicator may indicate if the SNP is homozygous or heterozygous.

For example, in some variations, the SNP indicator indicates a SNP that alters the function or expression of genes involved in the stress response, particularly the threshold of activation of the amygdala and hypothalamus. In some variations, the SNP indicator indicates a SNP that alters the function or expression of genes related to autonomic activation pathways. In some variations, the SNP indicator indicates a SNP that alters the function or expression of the glutamate metabolism pathway(s), which relates to cognition and long term potentiation. In some variations, the SNP indicator indicates a SNP that alters the function or expression of genes associated with executive brain function which includes attentional and motivational behavioral states.

The reports described herein may simplify the potentially complex and confusing application of personalized medicine for the treatment of resistance by providing a simplified and concise personalized diagnostic report that selects and organizes the relevant genotypic and phenotypic information in a manner that emphasizes only those aspects which are relevant; the report may also emphasize relevant (core) epistatic members, while omitting or separating out non-core genotype/phenotype information. The reports may also provide interpretive comments relevant to the drug response based on these core epistatic members. As described in greater detail below, these reports, and particularly the interpretive portion of the reports, may include an indexing or weighting system that provides a confidence level for the provided interpretive comments.

Thus, the dimensional assays described herein are best served by interpretive reports which include not just the results of the biomarker testing, but also give patient-specific guidance in treating the patient. There are multiple ways in which these interpretive reports provide substantial advantages and benefits; the examples included below illustrate the way in which patient care and treatment has benefitted from these tests.

FIGS. 1A-1D and 2A-2D illustrate two examples, respectively, of reports including genetic information that is patient-specific and relevant to treatment of treatment resistant disorders. For example in FIGS. 1A-1D, the report is divided up into four sections: serotonin neurotransmission (serotonin transporter and SNP functional variant of a single-nucleotide polymorphism (rs25531) in SLC6A4); dopamine/norepinephrine neurotransmission (MTHFR, COMT, and DRD2); glutamate neurotransmission (CACNA1C, and the like such as glutamate transporter genes); and pharmacokinetic analysis (CYP2D6, CYP2C19, CYP3A4 and the like). In these examples, generic interpretive comments describe the function of the genes tested, and the significance of the resulting genotypes. Finally each section indicates the patient-specific genotype result in a box following the interpretive results.

The report shown in FIGS. 1A-1D also includes a glossary of key terms, and may include references, a description of the genetic testing (including testing limitations) and contact information for further descriptions of the testing and/or results.

FIGS. 2A-2D illustrate another variation, in which a slightly different set of genetic loci form the core epistatic group displayed. In this variation the report includes a summary table (FIG. 2A) listing the gene tested (by class in each of three key classes: serotonin, dopamine and glutamate/ionic) and the patient genotype. This summary is followed by a "report guide" section describing the intent and use of the report. A description of the pharmacokinetic information (e.g., the CYP2D6 genetic locus) is described in FIG. 2B. This figure also shows the beginning of the section broken down by pharmacodynamic information. In this section the phenotype may be compared with the genotype to provide a suggested treatment. These treatment recommendations may be scored as indicated in FIG. 2C to determine a "certitude" of treatment recommendation. Finally, descriptive information for the various genotypes is provided in FIG. 2C. FIG. 2D includes a glossary of key terms and a description of the testing limitations. In another embodiment; the report is designed to provide analysis of biomarkers which are dimensionally associated with amygdala-HPA axis, cortical-subcortical axis, and LTP-LTD axis, as described above.

As mentioned above, the reports described herein, in addition to displaying and highlighting the genotype information for all or a subset of the core epistatic group may include one or more interpretive results.

For example, interpretive results that may be included for the serotonin neurotransmission locus (e.g., the SNP functional variant of a single-nucleotide polymorphism (rs25531) in 5-HTTLPR (serotonin-transporter-linked promoter region of the serotonin transporter gene)) may include descriptions of the gene or region of the gene examined by the genetic test ("the gene SLC6A4 encodes the 5-HTT, a membrane protein that transports serotonin from synaptic spaces into presynaptic neurons"), as well as information specifically relevant to the drug response/treatment response ("pharmacodynamic studies of the serotonin transporter gene suggest that patients with the S/S genotype do not respond as well to SSRI antidepressants and may experience more side effects," "in SSRI non responders who exhibit the S/S allele, consideration should be given to use of a non-SSRI," etc.). References may also be provided.

Interpretive comments that may be provided relevant to the dopamine/norepinephrine neurotransmission locus (e.g. the MTHFR-COMT) locus may include, for example: a description of the genetic locus and its relevance ("polymorphisms in the MTHFR-COMT result in genetic variations within the frontal cortex dopamine system. Functional variants of COMT may either increase or decrease dopamine degrading enzyme activity and impacts the efficiency of prefrontal dopamine. Prefrontal dopamine plays a critical role in cognition, executive function, working memory and attention. Significant epistasis (gene-gene interactions) has been demonstrated in MTHFR/COMT genotypes.") Genomic information, as well as information specifically relevant to the drug response/treatment response ("the MTHFR 677T/T and COMT 158Val/Val exacerbate prefrontal dopamine deficiency." "MTHFR/COMT genotypes should be obtained in patients with cognitive symptoms associated with a mood disorder and in patients who are being considered for methylfolate treatment." "variants of COMT in patients who are being considered for methylfolate treatment," "patients with either or both MTHFR/COMT Val/Val have higher COMT mediated dopamine degradation and may require augmentation with a methylation agent such as methylfolate." References may also be provided.

Interpretive comments that may be provided relevant to the DRD2 (the Dopamine receptor D2) of the dopamine/norepinephrine neurotransmission locus may include, for example: a description of the genetic locus and its relevance ("This gene encodes the D2 receptor, as well as information specifically relevant to the drug response/treatment ("Insertion/deletions of the promoter strongly influence striatal dopamine binding and may influence anti psychotic drug response," "Individuals who demonstrate a deletion allele demonstrate poorer antipsychotic response compared to insertion genotype," "Individuals with the deletion allele are at higher risk of atypical neuroleptic-induced weight gain," "DRD2 gene variants should be obtained in patients who are prescribed atypical neuroleptics.").

Interpretive comments that may be provided relevant to the Glutamate neurotransmission locus (CACNA1C) may include, for example: a description of the genetic locus and its relevance ("the CACNA1C gene in humans encodes a protein that is a voltage-dependent, L-type, alpha 1C subunit (also known as Cav1.2) of a calcium channel,"), as well as information specifically relevant to the drug response/treatment response ("This gene encodes the L-type voltage gated calcium channel which mediates intracellular calcium homeostasis and neuronal depolarization. CACNA1C polymorphisms have been associated as a risk factor gene for bipolar disease, schizophrenia and recurrent major depression. Risk allele carriers with polymorphisms in rs1086737 exhibit reduced activation of the anterior cingulate cortex, a region associated with mood regulation and stress related responses," "CACNA1C gene polymorphisms should be obtained in patients with a family history of bipolar disorder, SSRI-induced mania or suicidal ideation, and in cases of depression associated with psychotic features," "Patients with rs1086737 and the like have increased risk of SSRI treatment emergent suicidality and a mood stabilizer may be considered in these patients,"). References may also be provided.

Interpretive comments that may be provided relevant to the specific pharmacokinetic locus (2D6) may include, for example: a description of the genetic locus and its relevance ("2D6, or Cytochrome P450 2D6 (CYP2D6), is a member of the cytochrome P450 mixed-function oxidase system, and is involved in the metabolism of xenobiotics"), as well as information specifically relevant to the drug response/treatment response ("Polymorphisms in P450 enzymes account for significant variations in drug metabolism and the majority of psychotropic agents are metabolized by these pathways. Variance in the activity of cytochrome P450 can lead to abnormal drug metabolism and are associated with potential drug-drug interactions and treatment emergent side effects." "Aripiprazole (e.g., 'Abilify'), Atomoxetine ('Strattera'), Mirtazapine ('Remeron'), Venlafaxine ('Effexor'), Paroxetine ('Paxil'), fluoxetine ('Prozac') and Duloxetine ('Cymbalta') are examples of drugs primarily metabolized by the 2D6 enzyme, Poor metabolizers of 2D6 (2D6 PM) are at risk of Aripiprazole-induced akathesia and dosage reductions of approximately 30-40% are recommended." "Poor metabolizers taking Atomoxetine are at risk of Atomoxetine-induced side effects and an alternate agent is recommended," "Poor metabolizers taking Duloxetine should be cautioned or avoid using with concurrent 2D6 metabolized drugs such as Metoprolol," "Ultrametabolizers of 2D6 may have decreased drug concentrations and efficacy of Venlafaxine, Morphine and Tramadol. Obtaining serum levels should be considered in incomplete or non-responders using these agents,"). References may also be provided.

In general, the reports described herein highlight key genetic loci forming a previously unrecognized epistatic group that is relevant to treatment resistance for psychiatric disorders. By presenting a patient's genotype for the key genetic loci, as well as providing information specific the possible outcomes, the methods and reports described herein may enhance patient care.

The reports described herein may be referred to as articles of manufacture. The reports may be presented as a paper printout, or they may be digital. In digital formats, the reports may include links (e.g., hyperlinks) to references or additional sources. In variations including associated studies or current research findings as part of the interpretive comments and/or indexing/weighting of the information, links or references may be provided.

Example 2

Indexing/Weighting

As mentioned above, any of the interpretive reports described herein may include indexing or weighting of the interpretive comments. The various types of interpretive comments that may be included in the report include: physiological significance, association studies, current research findings, pharmacological implications, and the like. The information provided by the interpretive comments may be based on medical and scientific research, including both published and unpublished data.

All or a subset of the interpretive comments may be indexed with an indicator (which may also be referred to as an "index") providing a confidence level for the interpretive comment. For example, in some variations the interpretive comments may include a description or mention of the results of one or more association studies relevant to the patient's biomarker test results. An index may provide weighting context by indicating the appropriateness of the association study to support the interpretive comment. Thus, the report may indicate after the study mentioned a "grade" applied to the study (or to other interpretive comments) indicating the nature of the study (e.g., multiple studies reporting or supporting the provided association with the biomarker, a meta-analysis of multiple or single genome-wide studies supporting the association, multiple studies supporting the association, and a single study supporting the association). A letter, number, symbol, color, or other grade may be used. In some variations the indexing may rank the confidence level (e.g., having grades A through D, 1-4, etc.), with the strongest support being ranked "highest."

A key to the indexing or weighting may be provided as part of the report.

The indexing or weighting may be directly associated with the interpretive comment in the report. For example, the index may be provided as a subscript, superscript, parenthetical, or other text or visual indicator at the beginning or end of the interpretive comment. The index may also be represented in the display of all or a part of the interpretive comment (e.g., changing the color of the interpretive comment, the font, the size, etc.).

Indexing values for all or a subset of the interpretive comments may be generated manually or otherwise. An indexing value may be assigned based on a formula that weighs the reproducibility of the association, the size of the study supporting the interpretive comment, the type of study supporting the interpretive comment, the publication status of the study (which may include the source, e.g., journal, etc., of the study), a metric of how accepted the association is to those of skill in the art, and the presence of contradictory findings.

Example 3

Assay Report

FIGS. 3A-3B illustrate one portion of another variation of an interpretive report. FIGS. 5A-5D and 5E-5M show an alternative variation. In FIGS. 3A-B, the report ("Assay Report") includes a patient identifier (patient name, and/or "patient ID"). The report also indicates the source of the biomarker test results, including the sample type, ordering clinician, receive date, etc. This exemplary assay report also includes information from each of the four axes illustrated above in seven representative biomarkers: SLC6A4, CACNA1C, DRD2, COMT, MTHFR, HTR2C, ANK3, CYP2D6, CYP3A4, and CYP2C19. FIGS. 3C-3J also illustrate additional pages of the interpretive report.

FIG. 3A is the first the interpretive report. In this example, the report ("Assay Report") includes a patient identifier (patient name, and/or "patient ID"), followed by an interpretive key ("How to read the report" section). The interpretive key section describes the index/weighing system used by the report to provide a confidence level to the interpretive comments.

A summary of the results section follows, briefly summarizing the results of each biomarker test as well as the associated interpretive information and confidence index. In this example, the information summarized for each biomarker includes: the biomarker tested (e.g., SLC6A4), a description of what the biomarker is ("Serotonin Transporter"), an indicator of the result ("S/S"), and a brief description of the physiological significance of the test results. An image of the brain region implicated by the biomarker test result may also be shown. In FIGS. 3A and 3B, some of the biomarkers (the psychodynamic biomarkers) include a pair of images (e.g., an exemplary sagittal section and an exemplary coronal section through a brain), illustrating potentially affected brain regions. This spatial mapping may be based on the putative target brain regions indicated earlier.

The example report shown in FIGS. 3A-3B indicates a polymorphism for each examined biomarker. In some variations, when a biomarker result is notable as having a clinically or therapeutically relevant result, the report may highlight the biomarker and test result in some manner. For example, the biomarker test result may be made bigger, may be bolded, may be colored, may be highlighted, may be boxed, etc. In some variations the interpretive results may include an executive summary section that indicates or directs the physician to a potentially relevant result.

In FIG. 3A, the first test result summarized is the SLC6A4 (Serotonin Transporter) gene. The results for this exemplary test report indicate that the hypothetical patient is "S/S" or homozygous for the short allele. The interpretive comments describe the physiological significance and gene response association studies supporting the interpretive comments. In this case, the interpretive comments are also indexed or weighted to indicate a confidence level, and references to supporting documents are provided. For example, the physiological significance of the S/S result for the SLC6A4 biomarker result is described as "the short or S allele has been associated with decreased transcription of the serotonin transporter. This polymorphism has been associated with reduced stress resilience and higher rates of stress mediated psychological dysfunction as well as amygdala hyperactivity." Further interpretive comments ("gene response association studies") are also provided, such as "based upon existing published data, homozygote short allele variants are less likely to achieve remission of depression when treated with a SSRI(1) [D], and are more likely to have a higher number of anti-depressant trials(2) [D], and in geriatric patients are more likely to discontinue treatment with a SSRI (but not mirtazapine) due to adverse effects(4) [D]." In this example, the "D" following each of three different statements is an indexing element indicating that only a single study reports the described association (a relatively low confidence rating). The numbers in parenthesis following each statement refer the physician to a reference for further information; the references are listed at the end of the long report (FIGS. 3C-3F).

A similar description for the CACNA1C (calcium channel) gene, DRD2 (dopamine D2 receptor) gene, COMT (Catechol-O-Methyltransferase) gene, MTHFR (Methylenetetrahydrofolate Reductase) gene, ANK3 (ankyrin 3) gene, HTR2C (serotonin receptor 2C) gene, CYP2D6 (Cytochrome P450 2D6) gene, CYP3A4 (Cytochrome P450 3A4), and CYP2C19 (Cytochrome P450 2C19) gene is also provided.

Following the two-page summary of the results and interpretive comments, additional pages may be provided to go into even greater detail for each biomarker, including additional interpretive comment and enhanced view of potentially affected brain regions.

As mentioned above, in some variations, the report may be digitally provided or available. For example, a patient physician may be provided with access to a secure website storing patient information and the results of the assay; software (or firmware, hardware, etc.) running analysis logic may generate an interpretive report such as the one illustrated in FIGS. 3A-3J. FIG. 4 illustrates an alternative format for the report discussed above. FIG. 4 corresponds to the detailed portion of the COMT biomarker described in FIGS. 3E and 3F. FIG. 4 is available as an online (digital) report. In this example, the report is hyperlinked (e.g., to references) and allows toggling between different exemplary views (e.g., coronal, sagittal, and transversal).

Example 4

Assay Report

FIGS. 5A-5M illustrate another variation of an article of manufacture comprising an interpretive neuropsychiatric report of patient-specific and dimensional information relevant to the treatment of a neuropsychiatric disorder, the article of manufacture. In this example, the report includes patient identification information as mentioned above. In addition, the report includes a summary or overview. In instances where the patient does not have any variations indicating dysfunction in the axes examined (e.g., the autonomic arousal axis, the emotional valence, attention, reward and executive brain axis, and the long-term potentiation and long-term depression axis), the report may indicate that there is no reportable variation. For example, the report may indicate that the patient does not exhibit any variants for the genes tested. The report may further indicate that this result does not exclude other variation in the genes tested, the adverse influence of other genes not tested, or other metabolic factors associated with psychiatric disorders.

In general, the report includes a written description of biomarker test results specific to a patient for at least one biomarker for dysfunction in each of: (1) the patient's autonomic arousal system; (2) the patient's emotional valence, attention, reward and executive brain functions; and (3) the patient's long-term potentiation and long-term depression (LTP-LTD) function. In the example shown, the report also includes biomarkers for the metabolic axis. In some variations of the report the axes are highlighted; alternatively, the axes may not be separately indicated, but the biomarkers may be described. One or more interpretive comments may be included to provide an interpretive analysis of the neurophysiological significance of each biomarker test results for the patient, wherein the interpretive analysis comprises patient-specific information on response to a neurotherapeutic agent based on the biomarker test results.

For example, as shown in FIGS. 5A to 5D (representing exemplary pages 1-4 of a report), the biomarker for the autonomic arousal system is SLC6A4. In FIGS. 5A-5M, the exemplary patient has a number of variants indicating dysfunction, so that exemplary interpretive comments can be provided for many of the biomarkers. For example, in FIG. 5A, the patient is presumed to have the short variant of the SLC6A4 gene (S/S) as shown in FIG. 5E.

FIGS. 5A-5D show summaries or shortened/condensed versions of the information that is expanded in the second half of the report beginning in FIG. 5E.

FIGS. 7A-7G illustrate another variation of an article of manufacture comprising a report as described herein. In this variation, the biomarkers tested included those indicating a variation or disruption in one of the following genes (which include genes from each of the axes discussed above): SLC6A4, 5HT2C, CACNA1C, ANK3, DRD2, COMT, MTHFR and CYP 2D6, 2C19, 3A4/5. For this exemplary subject, variations were detected by the biomarker assay result in each of these genes tested. The report provides information on a biomarker for dysfunction in each of the following neuropsychiatric axes: (1) a patient's limbic mediated autonomic arousal system; (2) the patient's prefrontal-subcortical mediated emotional valence, attention, reward and executive brain systems; and (3) the patient's synaptic mediated long-term potentiation and long-term depression (LTP-LTD) system. In addition, biomarkers to test for dysfunction in the drug metabolism were also reported and examined.

Thus, FIGS. 7A-7G illustrate the presentation of a patient-specific written neuropsychiatric report including an interpretive analysis of the neurophysiological significance of the result of any biomarker for dysfunction collected. The interpretive analysis comprises a description of an association with a disorder or a dysfunction of brain activity or a disorder and dysfunction of brain activity based on the biomarker test results.

In some variations, the interpretive analysis also includes a recommendation for the prescription of a specified agent. For example, the interpretive analysis may include a recommendation for an agent (a specific agent) that down regulates excessive limbic activity, for example lithium, when the biomarker for dysfunction in the patient's autonomic arousal system axis indicates that the patient has the short allelic form of 5-HTTLPR.

FIG. 8 illustrates one variation of a neuropsychiatric report similar to the one shown in FIGS. 7A-7G, but wherein the subject (patient) did not have any reportable variations for any of the genes tested. In this case, the written article of manufacture indicates that the patient did not exhibit any variants in the genes tested (and in some variations indicates the genes tested). Because a negative result in each or any of these biomarkers may also provide informative and useful information, in some variations the article of manufacture may provide interpretive analysis on the negative finding.

FIG. 9 is another variation of a neuropsychiatric assay report in which the patient had a biomarker indicating dysfunction/variation in one of the genes tested the COMT gene. In this case, the patient has the Val/Val variant, as compared to FIG. 7C, where the patient has the Met/Met variation. In FIG. 9, the interpretive analysis is therefore tailored to the Val/Val variant.

Example 5

Biomarkers

Systems and reports for treating (or in some cases, diagnosing) neuropsychiatric disorders may include tests, assays, screens, kits, panels, and the like. In particular, the systems and reports described herein may be used to diagnose or treat depression. In other variations the systems and reports described herein may be used to diagnose or treat other neuropsychiatric disorders. Such systems may examine biomarkers for a specific axis, neurotransmitter pathway, and/or neuroanatomical region. For example, a cluster of biomarkers addressing a particular neurotransmitter pathway (or portion of a pathway) may be examined including ion channels, neurotransmitter receptors, etc. . . . In addition to each dimensional biomarker, pharmacokinetic biomarkers may be included as well. For example, brain-immune pathways and cerebral metabolism may be probed using one or more biomarkers. Exemplary neurotransmitters, ion channels, or the like are described in Table 1 below, and in other portions of this disclosure. For any of these, the systems described herein may be examined to determine an indicator of the genetic markers (e.g., SNPs), epigenetic markers (e.g., methylation), or protein expression. In addition, also described herein are specific clusters or groups of such genes/encoded proteins that may be examined in combination to provide particular relevance.

TABLE 1 genes for analysis and screening in a neuropsychiatric patient

| Gene | Exemplary SNP/ALLELE |
|---|---|
| Axis I: genetic markers of neuropsychiatric symptoms associated with autonomic hyperarousal; symptoms in these individuals, regardless of diagnosis, may include panic attacks, insomnia, hypervigilance, fear, increased startle, insomnia | |
| SERT (SLC6A4) | Ins/del, rs25531 |
| 5HT1A (HTR1A) | −1019 C > G, rs6295 |
| FKBP5 | rs3800373, rs1360780 |
| NPY | rs16147 |
| Axis II: genetic markers associated with dopamine dysregulation; symptoms may include attentional difficulty, poor focus, reduced ability to plan, impulsivity, motivational issues, cravings for reinforcing agents | |
| COMT | 472 G > A (Val158Met), rs4680 |
| SLC6A3 | VNTR 9/10 repeat |
| DRD2 | −141C insertion/deletion, rs1799732 |
| Axis III: genetic markers associated with disturbances in excitatory neurotransmission due to glutamate dysregulation, symptoms may include heightened irritability, cyclical and recurrent mood disturbances, paroxysmal complaints | |
| CACNA1C | G > A, rs1006737 |
| ANK3 | rs10994336 |
| BDNF | G > A (Val166Met), rs6265 |

In some variations of the systems, reports and methods described herein, therapeutic or treatment guidance may be provided based either specifically on the results or score for a particular patient, or more generally presented so that the medical health provider may apply the results of the various screen or panel to a set of guidelines.

For example, Table 3, below provides suggested therapeutic(s) based on the presence of one or more of the genetic, epigenetic or protein assays described herein for the various markers tested.

TABLE 2 exemplary therapeutic/interpretive guidance

| Axis I, generally | Norepinephrine reuptake inhibitors (Mirtazepine and the like), Atomoxetine, NRI, SNRIs, Agents which are primarily anxiolytic, reduce elevated stress related pathways (angiotensin receptor blockers) or Lithium. It is worthy to note that lithium may increase |

TABLE 2-continued exemplary therapeutic/interpretive guidance

| | transcription of the serotonin transporter protein, making it a particularly suitable agent for individuals with serotonin short allele variants. |
|---|---|
| Axis II, generally | Agents which increase activity of the prefrontal cortex such as transcranial magnetic stimulation |
| Axis III, generally | Mood stabilizers, such as Lithium, Lamotrigine, Memantine, Nimodipine, Vitamin D, Valproic acid, N-acetylcysteine, magnesium and the like; Racetam based agents (Aniracetam and the like), Tianeptine |

Additional examples may illustrate the application of the systems, reports and methods described herein for the application of this integrative technology to other neuropsychiatric disorders.

The reports, systems and method described herein may specifically include, discuss, and describe genes having epistatic effects. Epistasis refers to the phenomenon where the effects of one gene are modified by one or several other genes, which are sometimes called modifier genes. The gene whose phenotype is expressed is said to be epistatic. Such relationships may be previously unrecognized, and may aid in the diagnosis and treatment of neuropsychiatric disorders. For example, the inventor has discovered that individuals with COMT Val/Val in epistasis with MTHFR T/T may display a phenotype characterized by a subcortical type of mood disorder. These individuals commonly are abulic, dysthymic, and anergic. This phenotype may be expressed secondary to reduced prefrontal dopamine as a consequence of these genes in epistasis, resulting in excess dopamine degradation. Thus, a system, report or method may examine the combination of COMT and MTHFR and/or dopamine neurotransmitter pathway genes; one or more of genetic markers, epigenetic markers and/or protein expression may be examined to determine if a patient has or is at risk for the correlated abulic, dysthymic, and anergic phenotype.

In another example, the combination of the SLC6A4 short allele and CACNA1C variants has also been linked by the inventor to a particular phenotype which may be specifically amenable to treatment, either to enhance treatment or to select between available treatments that would otherwise be seemly equivalent based only on the phenotype presented to the physician. For example, SSRI induced mania may be higher in these patients.

We herein further postulate herein that neuropsychiatric subtypes may be based upon imbalances between excitatory and inhibitory mechanisms in the brain. Certain subtypes of depression or dementia are associated with predominant excitatory pathways (such as excess glutamate) which involve abnormal expression of genes and neurotransmitters leading to specific phenomenological behavioral states. In other subtypes of disorders, inhibitory pathways predominate, with abnormal expression of a separate and distinct set of genes and neurotransmitters. Thus, a clinician may be able to ascertain specific subtypes by analyzing both the behavioral and genetic patterns of individuals with neuropsychiatric disorders.

Another example includes looking at mood disorders differentiated by heightened or reduced activity of the amygdala and hypothalamic fight or flight response. In certain individuals, such as those with the SLC6A4 short allele, demonstrate heightened fear response as a result of amygdala excitation. Other genes are likely to evoke similar reductions in the threshold of excitatory pathways, such as FKBP5 and the like. Phenotypically, these patients often demonstrate an imbalance of excess excitation-panic, anxiety, frequent decompensations, and reduced stress resilience. This is in stark comparison to genotypes where there is reduced CNS activity, such as anhedonic states of depression where an activating agent, such as a stimulant, would be more indicated.

In addition to the COMT/MTHFR epistatic relationship, other epistatic sets of genes may also be included, described and discussed in any of the kits, systems, reports and methods.

Example 6

Patient Results

The systems, methods and reports described herein have been successfully used during a preliminary testing phase for the neuropsychological assay described above in Example 4. Neuropsychological patients were tested and the results provided to their treating physician. The physician, using the provided test results and interpretive comments treated the patients as suggested by the interpretive comments. Five examples of patients, the results of their neuropsychiatric assay and the resulting physician treatment following receipt of the interpretive assay results are described herein. In general the tests have been surprisingly effective in aiding in patient care, proving (1) biomarker test results that are specific to depression (in these examples), and (2) interpretive comments based on the biomarker results that is useful to guide treatment.

For example, a 16 year-old girl was tested (via an in-office saliva collection); the saliva sample was examined as discussed above, and results were provided to generate an interpretive report as described above. In this case, the patient had a history of excessive anxiety starting from the age of three. She was raped at age 14, and shortly after that had begun cutting herself and often had trouble sleeping. The patient was described as hyper vigilant, and worried about worst case scenarios. She had been prescribed SSRIs, which made her symptoms significantly worse. The results of the neuropsychiatric assay described in here found that her SLC6A4 biomarker indicated that she was homozygous for the short allele ("S/S") and within normal parameters for the other biomarkers. Based on these results, the clinician elected to provide a noradrenergic agent, as predicted by the interpretive comments. Treatment with the noradrenergic agent resulted in specific and attenuated reduction in her symptoms.

In a second example, a 56 year-old man, who has been a very successful businessman, sought the help of a psychiatrist complaining of chronic dysthymia (e.g., low grade persistent depression, also described as "melancholic depression" because of significant vegetative behavior), low libido, excessive fatigue and low motivation. An assay such as the one described in FIGS. 3A-3J was performed using a patient saliva test. The patient's biomarker results (e.g., genotype) were most remarkable for a COMT Val/Val polymorphism. Because of these results, the clinician elected to prescribe psychostimulants (targeted as dopamine agonist). The patient reported significant benefits in overall mood, energy and focus following the use of this agent.

In a third example, the patient was a 44 year-old woman with a history of migraines and cyclical depression, with her depression worsening prior to the start of her menstrual cycle. Her treating psychiatrist prescribed an SSRI for depression. The SSRI therapy made her symptoms worse, and was self-discontinued. Following administering of the assay, the test results were passed on to a system/device that generates the customized (patient-specific) interpretive assay report.

The interpretive assay indicated that, though the patient was within normal tolerances for the other biomarker test results, she has a polymorphism in her CACNA1C gene. Based on this previously unsuspected result the treating physician elected to treat her with mood stabilizer (Valproic acid). This therapy resulted in a dramatic improvement in the patient's migraines and mood.

In a fourth example, a 50 year-old female patient sought treatment from a psychiatrist complaining of severe depression, precipitated by a divorce request. The patient had a history of depression but had not been medicated for many years. After developing depression she was prescribed a multitude of medications, including SSRI, Abilify, Ativan, etc. . . . . . Although the drugs did improve her symptoms, she complained that the medications made her feel excessively sedated, and also lead her to gain a significant amount of weight. The dimensional assay was provided as discussed herein, and the results of the biomarker testing used to provide an interpretive report. The most remarkable result of the neuropsychiatric assay was the indication that the patient has an MTHFR variant and normal folic acid levels. Based on this result and the interpretive report, the clinician elected to give high doses of methyl folic acid. Within 2 weeks the patient reported significant improvements in mood and in weight loss. This case is of particular interest because MTHFR variants such as hers have been associated with obesity and methyl folic acid response.

Another example, illustrates the multiaxial nature of the test, showing the assays and reports may successfully be used to interpret polygenic testing via the assays described. For example, a 34 year-old woman with bipolar depression, characterized by rapid cycling disorder, and also diagnosed with PTSD, panic attacks and sleep disorder, sought help from her psychiatrist. In the past, she has exhibited an incomplete and unsatisfactory response to prior SSRI trials, including Prozac, Zoloft, and Cymbalta, and while on them experienced mania and agitation. She was subsequently prescribed Abilify (aripiprazole), and saw an initial improvement of her symptoms; however, once the drug dosage was raised to 5 mg, the patient developed significant akathesia resulting in discontinuation of the drug. The neuropsychiatric assay was performed, and her physician was informed of the results, which indicated primarily that she was heterozygous for the short allele of the serotonin transporter (SLC6A4), and also has a DRD2 deletion allele, and a calcium channel variant (CACN1C). Based on these results, she was prescribed lithium, and within a short amount of time experiences a profound improvement.

As discussed above, the prescription of mood stabilizers would be expected to have adverse side effects to antipsychotics because of a deletion allele, and was an incomplete responder to SSRIs because of the DRD2 deletion. Further, the presence of a calcium channel snp predicts that the patient would be at a heighted vulnerability to bipolar disorders. On this basis alone, the decision to prescribe a mood stabilizer is in keeping with the interpretive comments.

In all of the case histories described briefly above, the interpretive results suggested a course of action which was strongly and surprisingly effective in treating neuropsychiatric disorders.

While the reports, methods of forming them, systems, and methods for using them, have been described in some detail here by way of illustration and example, such illustration and example is for purposes of clarity of understanding only. It will be readily apparent to those of ordinary skill in the art in light of the teachings herein that certain changes and modifications may be made thereto without departing from the spirit and scope of the invention.

What is claimed is:

1. In a computer processor, a method of generating a neuropsychiatric report presenting patient-specific information relevant to the treatment of a patient's neuropsychiatric disorder, the method comprising:

collecting, by the processor, results of biomarker tests specific to the patient for at least one biomarker for each of: (1) the patient's limbic mediated autonomic arousal system, wherein the biomarker is related to a gene consisting of solute carrier family 6 member 4 (SLC6A4); (2) the patient's prefrontal-subcortical mediated emotional valence, attention, reward and executive brain systems, the biomarker related to a gene selected from the group consisting of: catechol-O-methyltransferase (COMT), and dopamine receptor D2 (DRD2); and (3) the patient's synaptic mediated long-term potentiation and long-term depression (LTP-LTD) system the biomarker related to a gene selected from the group consisting of: calcium channel, voltage-dependent, L type, alpha 1C subunit (CACNA1C), and ankyrn 3 (ANK3);

selecting, by the processor, an interpretive comment based on the results of the biomarker tests;

organizing, by the processor, the results of the biomarker tests and one or more interpretive comments in a patient-specific neuropsychiatric report; and presenting the patient-specific neuropsychiatric report, wherein the report comprises an interpretive analysis of the neuropsychological significance of the result of any biomarker test collected, the report further comprising the one or more interpretive comments, the interpretive comments including a description of an association with a disorder or a dysfunction of brain activity or a disorder and dysfunction of brain activity based on the biomarker test results.

2. The method of claim 1, wherein selecting comprises selecting a recommendation for the prescription of a specified agent which downregulates excessive limbic activity, when the biomarker in the patient's autonomic arousal system axis indicates that the patient has the short allelic form of solute carrier family 6 member 4 (SLC6A4).

3. The method of claim 1, wherein selecting comprises selecting a recommendation for other calcium, sodium or calcium and sodium channel modulators of the Central nervous system, when the biomarker in the patient's synaptic mediated long-term potentiation and depression (LTP-LTD) function axis indicates that the patient has a polymorphism of the calcium channel, voltage-dependent, L type, alpha 1C subunit (CACNA1C) calcium channel gene or sodium channel gene.

4. The method of claim 1, wherein selecting comprises selecting a recommendation for S-adenosyl methionine when the biomarker in the patient's prefrontal-subcortical emotional valence, attention, reward and executive brain function axis indicates that the patient has a met/met polymorphism of the catechol-O-methyltransferase (COMT) gene.

5. The method of claim 1, wherein selecting comprises selecting a recommendation for stimulation of the dorsal lateral prefrontal cortex when the biomarker in the patient's prefrontal-subcortical emotional valence, attention, reward and executive brain function axis indicates that the patient has a val/val polymorphism of the catechol-O-methyltransferase (COMT) gene.

6. The method of claim 1, wherein selecting comprises selecting a recommendation for a folic acid when a biomarker indicates that the patient has a polymorphism of the methylenetetrahydrofolate reductase (MTHFR) gene.

7. The method of claim 1, wherein the neuropsychiatric disorder is selected from the group including: depressive disorders, bipolar disorder, anxiety disorders, PTSD, schizophrenia, autism, ADHD, and treatment resistant forms of these disorders.

8. The method of claim 1, further comprising providing a referral to a call center to receive additional interpretive analysis, clinical decision support, psychiatric focused genetic counseling, and/or neuroradiologists for imaging interpretation and analysis.

9. The method of claim 1, wherein collecting comprises collecting biomarker test results specific to the patient for a pharmacokinetic biomarker.

10. The method of claim 9, wherein the pharmacokinetic biomarker comprises gene families and pathways known to be involved in the absorption, distribution, metabolism or elimination of drugs.

11. The method of claim 1, further wherein presenting the patient-specific neuropsychiatric report comprises presenting a visual representation of a brain region associated with any biomarker for dysfunction collected.

12. The method of claim 1, wherein the biomarker test results indicate polymorphism, deletion, repetition, insertion, methylation level, allele specific methylation, expression level, expression localization, activity, or metabolites of one or more gene, gene family, pathway, transcript, protein, neurotransmitter or result acquired from brain imaging.

13. The method of claim 1, wherein collecting comprises collecting an additional biomarker in the patient's limbic autonomic arousal system axis where the biomarker is a marker of a variant of a gene, or a selected from the group consisting of: angiotensin I converting enzyme 1 (ACE), neuropeptide Y (NPY), FK506-binding protein 5 (FKBP5), and serotonin 5-HT-1A receptor (HTR1A).

14. The method of claim 1, wherein collecting comprises collecting an additional biomarker in the patient's prefrontal-subcortical emotional valence, attention, reward and executive brain functions axis where the biomarker is a marker of a variant of a gene consisting of solute carrier family 6 member 31 (SLC6A3).

15. The method of claim 1, wherein collecting comprises collecting an additional biomarker in the patient's synaptic mediated long-term potentiation and long-term depression (LTP-LTD) function axis where the biomarker is a marker of a variant of a gene selected from the group consisting of: solute carrier family 1 member 1 (SLC1A1), brain-derived neurotrophic factor (BDNF), and apolipoprotein E (APOE).

16. The method of claim 1, wherein selecting comprises selecting a an interpretive comment indicating, based on the patient's biomarker results, the patient's potential heightened response to a neurotherapeutic agent selected from the group consisting of: norepinephrine modulators, angiotensin receptor blockers, dopamine augmenting agents, monoamine oxidase inhibitors, catechol-O-methyltransferase (COMT) inhibitors, COMT upregulators, mood stabilizers, calcium channel agents, AMPA-receptro potentiators, Tianeptine or dorsal lateral prefrontal cortex stimulation.

17. The method of claim 1, wherein presenting comprises digitally presenting the patient-specific neuropsychiatric report.

18. In a computer processor, a method of generating a neuropsychiatric report presenting patient-specific information relevant to the treatment of a patient's neuropsychiatric disorder, the method comprising:

collecting, by the processor, results of biomarker tests specific to the patient for at least one biomarker in each of:
   (1) the patient's limbic based autonomic arousal system axis, wherein the biomarker is related to a protein encoded or modulated by a gene selected from the group consisting of: solute carrier family 6 member 4 (SLC6A4), angiotensin I converting enzyme 1 (ACE), neuropeptide Y (NPY), FK506-binding protein 5 (FKBP5), and serotonin 5-HT-1A receptor (HTR1A);
   (2) the patient's prefrontal-subcortical emotional valence, attention, reward and executive brain function axis, the biomarker related to a protein encoded or modulated by a gene selected from the group consisting of: catechol-O-methyltransferase (COMT), solute carrier family 6 member 31 (SLC6A3), and dopamine receptor D2 (DRD2); and
   (3) the patient's synaptic mediated long-term potentiation and depression (LTP-LTD) function axis, the biomarker related to a protein encoded or modulated by a gene selected from the group consisting of: calcium channel, voltage-dependent, L type, alpha 1C subunit (CACNA1C), solute carrier family 1 member 1 (SLC1A1), ankyrn 3 (ANK3), brain-derived neurotrophic factor (BDNF), and apolipoprotein E (APOE);

selecting, by the processor, an interpretive comment based on the results of the biomarker tests;

organizing, by the processor, the results of the biomarker tests and one or more interpretive comments in a patient-specific neuropsychiatric report; and presenting the patient-specific neuropsychiatric report, wherein the report comprises an interpretive analysis of the neuropsychological significance of the result of any biomarker test collected, the report further comprising the one or more interpretive comments, the interpretive comments including a description of an association with a disorder or a dysfunction of brain activity or a disorder and dysfunction of brain activity based on the biomarker test results.

* * * * *

UNITED STATES PATENT AND TRADEMARK OFFICE
CERTIFICATE OF CORRECTION

PATENT NO. : 8,706,526 B2
APPLICATION NO. : 13/739970
DATED : April 22, 2014
INVENTOR(S) : Jay L. Lombard Page 1 of 1

It is certified that error appears in the above-identified patent and that said Letters Patent is hereby corrected as shown below:

In the Claims

Claim 13, column 56, line 34; after "gene" and before "selected" delete ", or a".

Claim 16, column 56, line 59; after "AMPA-" and before "potentiators," delete "receptro" and insert --receptor--.

Signed and Sealed this
Twenty-ninth Day of September, 2015

Michelle K. Lee
*Director of the United States Patent and Trademark Office*